US012006500B2

(12) United States Patent
Tang et al.

(10) Patent No.: US 12,006,500 B2
(45) Date of Patent: Jun. 11, 2024

(54) COMPOSITION AND METHODS OF RNAI PROPHYLACTICS AND THERAPEUTICS FOR TREATMENT OF SEVERE ACUTE RESPIRATORY INFECTION CAUSED BY 2019 NOVEL CORONAVIRUS (2019-NCOV)

(71) Applicant: Sirnaomics, Inc., Gaithersburg, MD (US)

(72) Inventors: Danny Tang, Guangdong (CN);
Xueping Chen, Guangdong (CN);
Patrick Y. Lu, Potomac, MD (US);
Vera Simonenko, Gaithersburg, MD (US); David Evans, Gaithersburg, MD (US); John Xu, Gaithersburg, MD (US); Deling Wang, Jiangsu (CN);
Alan Lu, Gaithersburg, MD (US)

(73) Assignee: Sirnaomics, Inc., Germantown, MD (US)

( * ) Notice: Subject to any disclaimer, the term of this patent is extended or adjusted under 35 U.S.C. 154(b) by 155 days.

(21) Appl. No.: 17/157,920

(22) Filed: Jan. 25, 2021

(65) Prior Publication Data
US 2021/0246448 A1 Aug. 12, 2021

Related U.S. Application Data

(60) Provisional application No. 62/965,063, filed on Jan. 23, 2020.

(51) Int. Cl.
| | | |
|---|---|---|
| *C12N 15/113* | (2010.01) | |
| *A61K 9/51* | (2006.01) | |
| *A61K 31/713* | (2006.01) | |
| *A61K 47/28* | (2006.01) | |
| *A61K 47/69* | (2017.01) | |
| *A61P 31/14* | (2006.01) | |

(52) U.S. Cl.
CPC ............ *C12N 15/113* (2013.01); *A61K 9/513* (2013.01); *A61K 31/713* (2013.01); *A61K 47/28* (2013.01); *A61K 47/6931* (2017.08); *A61P 31/14* (2018.01)

(58) Field of Classification Search
CPC .............. C12N 15/113; C12N 2310/14; A61K 47/6931; A61K 31/713
See application file for complete search history.

(56) References Cited

U.S. PATENT DOCUMENTS

| | | | | |
|---|---|---|---|---|
| 7,297,786 B2 * | 11/2007 | McCray | ............ | C12N 15/1137 424/494 |
| 2005/0100885 A1 * | 5/2005 | Crooke | ............ | C12N 15/1137 435/5 |
| 2006/0257852 A1 | 11/2006 | Rappuoli et al. | | |
| 2008/0171025 A1 | 7/2008 | Mixson | | |
| 2019/0030187 A1 | 1/2019 | Lu et al. | | |
| 2021/0317457 A1 * | 10/2021 | Beigelman | ............ | A61K 45/06 |
| 2021/0348167 A1 * | 11/2021 | Vieira Araujo Soares Da Silva | ............. | C12N 15/1131 |
| 2022/0127615 A1 * | 4/2022 | Akinc | ............... | C12N 15/1131 |

FOREIGN PATENT DOCUMENTS

| | | | |
|---|---|---|---|
| WO | 2005/076999 A2 | 8/2005 | |
| WO | 2012/016139 A2 | 2/2012 | |
| WO | 2014/011512 A1 | 1/2014 | |
| WO | WO-2017044507 A2 * | 3/2017 | ............. A61K 47/28 |
| WO | 2022/072950 A1 | 4/2022 | |

OTHER PUBLICATIONS

Wu, F., et al., "A new coronavirus associated with human respiratory disease in China", Nature, vol. 579, 2020, pp. 265-269.
International Search Report and the Written Opinion in PCT/US2021/014962, dated Aug. 5, 2021, 12 pages.
Extended European Search Report in corresponding EP Application No. 21744210.2, Sep. 15, 2023, 18 pages.
Li, Bao-jian et al., "Using siRNA in prophylactic and therapeutic regimens against SARS coronavirus in Rhesus macaque", Nature Medicine, vol. 11(9), Aug. 2005, pp. 944-951.
Hasan, Anayet et al., "Design of potential RNAI (miRNA and siRNA) molecules for Middle East respiratory syndrome coronavirus (MERS-CoV) gene silencing by computational method", Program and Abstracts of the 25th International Conference on Antiviral Research (ICAR), May 11, 2015, p. 128, Abstract 179.
Liu, Peng-fei et al., "Prospect on the application of RNA interference technique to prevent and treat coronavirus disease 2019", Journal of Tongji University (Medical Science), vol. 41(2), Apr. 2020, pp. 141-146.
Chowdhury, Umar Faruq et al., "A Computational Approach to Design Potential siRNA Molecules as a Prospective Tool for Silencing Nucleocapsid Phosphoprotein and Surface Glycoprotein Gene of SARS-CoV-2", bioRxiv, Apr. 2020, pp. 1-12.
Gu, Se Hun et al., "A Small interfering RNA lead targeting RNA-dependent RNA-polymerase effectively inhibit the SARS-CoV-2 infection in Golden Syrian hamster and Rhesus macaque", bioRxiv, Jul. 2020, pp. 1-25.
Medeiros, Inácio Gomes et al., "A small interfering RNA (siRNA) database for SARS-CoV-2", bioRxiv, Oct. 2020, pp. 1-16.
Lakshmi, N. J. et al., "Design of Potential RNAi Molecules for Targeting COVID-19", International Journal of Biology, Pharmacy and Allied Sciences, vol. 9(11), Nov. 2020, pp. 2951-2964.

(Continued)

*Primary Examiner* — Brian Whiteman
(74) *Attorney, Agent, or Firm* — Edell, Shapiro & Finnan, LLC

(57) ABSTRACT

Compositions and methods for development of potent siRNA therapeutics for prevention and treatment of Corona Virus (2019-nCoV; COVID-19) infections are provided. The compositions include a pharmaceutical composition comprising siRNA cocktails that target critical viral genes and pharmaceutically acceptable polymeric nanoparticle carriers and liposomal nanoparticle carriers. Administration methods for prevention and treatment are provided, including airway instillation, subcutaneous injections and nebulizer aerosolization.

16 Claims, 30 Drawing Sheets

Specification includes a Sequence Listing.

(56) References Cited

OTHER PUBLICATIONS

Aneja, Kawalpreet K. et al., "Can RNAi be used as a weapon against COVID-19/SARS CoV-2?" Microbiology Discovery, vol. 8(1), Dec. 2020, pp. 1-12.
Chen, Q-R. et al., "Co-polymer of histidine and lysine markedly enhances transfection efficiency of liposomes", Gene Therapy, vol. 7(19), Oct. 2000, pp. 1698-1705.
Chou, S-T. et al., "Selective modification of HK peptides enhances siRNA silencing of tumor targets in vivo", Cancer Gene Therapy, vol. 18(10), Aug. 2011, pp. 707-716.
Kudsiova, Laila et al., "Delivery of siRNA using ternary complexes containing branched cationic peptides: the role of peptide sequence, branching and targeting", Molecular BioSystems, vol. 12(3), 2016, pp. 934-951.
Leng, Q. et al., "Systemic delivery of HK Raf-1 siRNA polyplexes inhibits MDA-MB-435 xenografts", Cancer Gene Therapy, vol. 15(8), May 2008, pp. 485-495.
Chou, Szu-Ting et al., "Surface-Modified HK:siRNA Nanoplexes with Enhanced Pharmacokinetics and Tumor Growth Inhibition", Biomacromolecules, vol. 14(3), Feb. 2013, pp. 752-760.
Leng, Q. et al., "Advances in Systemic siRNA Delivery", Drugs of the Future, vol. 34(9), Sep. 2009, pp. 721-737.

\* cited by examiner

Figure 14

| siRNA name | Gene targeted | Knockdown efficiency of target genes (%) | | EC50 | |
|---|---|---|---|---|---|
| | | 293T | A549 | 293T | A549 |
| guangzhou5 | S | ~75% | ~80% | | |
| guangzhou12 | | ~70% | ~85% | | |
| guangzhou13 | | ~76% | ~82% | | |
| guangzhou16 | | ~83% | ~80% | ~20.4 | |
| guangzhou21 | | ~81% | ~91% | | |
| guangzhou22 | | ~83% | ~90% | ~23.2 | |
| guangzhou23 | | ~79% | ~87% | | |
| guangzhou25 | | ~83% | ~90% | | |
| guangzhou30 | | ~86% | ~78% | | |
| guangzhou31 | | ~81% | ~73% | ~44 | |
| guangzhou32 | | ~89% | ~90% | ~8.0 | ~7.0 |
| SCo34 | | ~60% | ~74% | ~3732 | |
| SCo1 | ORF1AB | ~76% | ~80% | | |
| SCo2 | | ~73% | ~76% | | |
| SCo8 | | ~52% | ~65% | ~3186 | |

Figure 19 (Table 1)

| siRNA Sequence (sense): T to U (5'-3') | SEQ ID NO: | siRNA Sequence (anti-sense): (5'-3') | SEQ ID NO: | G/C content (%) | Start base in 2019-nCoV Sequence (from No. 1 to No. 29875) |
|---|---|---|---|---|---|
| GUUCAACUUAGUGAAAUUAdTdT | 203 | UAAUUUCACUAAGUUGAACdTdT | 263 | 23.81 | 12604 |
| CUUGAACAGCCCUAUGUGdTdT | 204 | ACACAUAGGGCUGUUCAAGdTdT | 264 | 47.62 | 471 |
| GAAAACUACCGAAGUUGUAdTdT | 205 | UACAACUUCGGUAGUUUCdTdT | 265 | 38.10 | 6477 |
| GAUGUUGUUAACAAUGCUdTdT | 206 | AGCAUUGUUAACAACAUCdTdT | 266 | 38.10 | 10952 |
| CAUGCAGGGUGCUGUAGACdTdT | 207 | GUCUACAGCACCCUGCAUGdTdT | 267 | 52.38 | 12041 |
| CACCUUAUGGGUUGGAUUdTdT | 208 | AAUCCAACCCAUAAGGUGdTdT | 268 | 42.86 | 15293 |
| GCCAUGCUUAACAUGCUUAdTdT | 209 | UAAGCAUGUUAGGCAUGCdTdT | 269 | 47.62 | 15327 |
| CCUUACCCAGAUCCAUCAAdTdT | 210 | UUGAUGGAUCUGGGUAAGGdTdT | 270 | 47.62 | 15944 |
| GCACACUAGAACCAGAAUAdTdT | 211 | UAUUCUGGUUCUAGUGUGCdTdT | 271 | 38.10 | 17496 |
| UAUGACUAUGUCAUAUUCAdTdT | 212 | UGAAUAUGACAUAGUCAUAdTdT | 272 | 28.57 | 17862 |
| CAUUUGAGCUUUGGCUAAdTdT | 213 | UUAGCCAAAGCUCAAAUGdTdT | 273 | 47.62 | 19797 |
| GAGUCACAUUAAUUGGAGAdTdT | 214 | UCUCCAAUUAAUGUGACUCdTdT | 274 | 38.10 | 20125 |
| GUUCUUCUCGUAAGAACGGUAAUA | 215 | UAUUACCGUUCUUACGAGAAGAAC | 275 | 36.00 | 642 |
| CAUGUGGUAGUUGUUUUAACAU | 216 | AUGUUAAAACAACUACCACAUG | 276 | 36.00 | 10501 |
| GAUCUGAGGACAAGAGGCAAAAGU | 217 | ACUUUUGCCCUCUUGUCCUCAGAUC | 277 | 48.00 | 12331 |
| CACUACAAGUUUUUGGACCACUAGU | 218 | ACUAGUGGUCCAAAACUUGUAGGUG | 278 | 44.00 | 14421 |
| CACUAUAUGUUAAACCAGGUGAAC | 219 | GUUCACCUGGUUUAACAUAUAGUG | 279 | 40.00 | 15471 |
| CUUGUCGAUUCCAGAUCUUAAUGACU | 220 | AGUCAUUAAGAUCUGGAAUCGACAAG | 280 | 36.00 | 20957 |
| GGGCUAGAGUCCCUAAGAGUGAUGG | 221 | CCAUCACUCUUAGGGAAUCUAGCCC | 281 | 52.00 | 12589 |
| GUGGAAAGGUAUGGCUGUAGUUGU | 222 | ACAACUACAGCCAUACCUUUCCAC | 282 | 44.00 | 13406 |
| GUGACAUGGUACCACAUAUAUCACG | 223 | CGUGAUAUAUGUGGUACCAUGUCAC | 283 | 44.00 | 13779 |
| CAAUAGCCGCCACUAGAGGAGCUAC | 224 | GUAGCUCCUCUAGUGGCGGCUAUUG | 284 | 56.00 | 15189 |
| CACCUACACAGGCCACUACACACC | 225 | GGUGUGUAGGUGCCUGUGUAGGAUG | 285 | 56.00 | 18110 |
| CUACCACAGGCACCUACACCUCAG | 226 | CUGAGGUGUAGGUGCCUGUGUAG | 286 | 56.00 | 18114 |
| CAUAACAGAUGCCAAACAGGUUCA | 227 | UGAACCUGUUUGGCGCAUCUGUUAUG | 287 | 44.00 | 20473 |
| GUUUCUUUAAGGAAGAAGUUCUGU | 228 | ACAGAACUUCCUUCCUUAAAGAAAC | 288 | 36.00 | 14736 |
| GGACCACUGGUACUGGUAAGAGUC | 229 | GACUCUUACCAGUACCAGUGGUCC | 289 | 56.00 | 17096 |
| CCUGGUACUGGUAAGAGUCAUUUG | 230 | CAAAUGACUCUUACCAGUACCAGG | 290 | 44.00 | 17102 |
| UACUUUGAUUGUUACGAUGGUGGCU | 231 | AGCCACCAUCGUAACAAUCAAAGUA | 291 | 40.00 | 14891 |

Figure 19 (Table 1) (continued)

| Sequence | # | Sequence | # | Value |
|---|---|---|---|---|
| GAUUGUUACGAUGGUGGCUGUAUUA | 232 | UAAUACAGCCACCAUGCUAACAAUC | 292 | 40.00 | 14897 |
| CAAUGAGUUAUGAGGAUCAAGAUGC | 233 | GCAUCUUGAUCUCAUAACUCAUUG | 293 | 40.00 | 15009 |
| GUUAUGAGGAUCAAGAUGCACUUUU | 234 | AAAGUGCAUCUUGAUCUCAUAAC | 294 | 36.00 | 15015 |
| CCUAAUCAGGAGUAUGCUGAUGUCU | 235 | AGACAUCAGCAUACUCCUGAUUAGG | 295 | 44.00 | 16073 |
| GAGUUUAUGAGGCUAUGUACACAC | 236 | GUGUGUACAUAGCCUCAUAAACUC | 296 | 40.00 | 16211 |
| CUCUGAAGAAGUAGUGGAAAAUCCU | 237 | AGGAUUUCCACUACUCUUCAGAG | 297 | 40.00 | 6422 |
| GUAGUGGAAAAUCCUACCAUACAGA | 238 | UCUGUAUGGUAGGAUUUCCACUAC | 298 | 40.00 | 6432 |
| CAACGAGAAAAACACGUCCAACUC | 239 | GAGUUGGACGUGUGUUUUCGUUG | 299 | 48.00 | 305 |
| GAAAACACGUCCAACUCAGUUUG | 240 | CAAACUGAGUUGGACGUGUGUUUUC | 300 | 44.00 | 311 |
| GGGUAAGGCUAGACUGUUAUUAUGA | 241 | UCAUAAUAAAGUCUAGCCUUACCC | 301 | 40.00 | 14982 |
| GUCCUGCUGAAAUGUUGACACUGU | 242 | ACAGUGUCAACAAUUCAGCAGGAC | 302 | 44.00 | 17583 |
| CAGAACUGGAACCACCUUGUAGGUU | 243 | AACCUACAAGGUGGUUCCAGUUCUG | 303 | 48.00 | 12901 |
| CCUGUAGGUUGUGUUACAGACACAC | 244 | GUGUGUCUGUAACAACCUACAAGG | 304 | 44.00 | 12915 |
| CUUUUCAAACUGUCAAACCGGUAA | 245 | UUACCGGUUUGACAGUUUGAAAAG | 305 | 40.00 | 14673 |
| GCAAAAUGUUGGACTGAGACTGACC | 246 | GGUCAGUCUCAGUCCAACAUUUUGC | 306 | 48.00 | 15845 |
| GACTGAGACTGACCTTACTAAAGGA | 247 | UCCUUUAGUAAGGUCAGUCUCAGUC | 307 | 44.00 | 15856 |
| GAGAGUACACCUUUGAAAAGGUGA | 248 | UCACCUUUUCAAAGGUGUACUCUC | 308 | 40.00 | 16839 |
| GAAAAAGGUGACUAUGGUGAUGCUG | 249 | CAGCAUCACCAUAGUCACCUUUUUC | 309 | 44.00 | 16853 |
| CUCAGAUGAGUUUUCUAGCAAUGUU | 250 | AACAUUGCUAGAAAACUCAUCUGAG | 310 | 36.00 | 17026 |
| GAUGAGUUUUCUAGCAAUGUUGCAA | 251 | UUGCAACAUUGCUAGAAAACUCAUC | 311 | 36.00 | 17030 |
| GCAAUGUUGCAAAUUAUCAAAAGGU | 252 | ACCUUUUGAUAAUUUGCAACAUUGC | 312 | 32.00 | 17043 |
| GUUUUUAAACCGGUUUGCGGUGUAA | 253 | UUACACCGCAAACCGGUUUAAAAAC | 313 | 40.00 | 13475 |
| GGGUUUGCGGUGUAAGUGCAGCCCG | 254 | CGGGCUGCACUUACACCGCAAACCC | 314 | 64.00 | 13485 |
| GUAAGUGCAGCCCGUCUUACACCGU | 255 | ACGGUGUAAGACGGGCUGCACUUAC | 315 | 56.00 | 13496 |
| GUGCGGGCACAGGCACUAGUACUGAU | 256 | AUCAGUACUAGUGCCUGUGCCGCAC | 316 | 56.00 | 13519 |
| GUAAUGUCAUCCUACUAUAACUCA | 257 | UGAGUUAUAGUAGGAUGACAUUAC | 317 | 36.00 | 15054 |
| GAAUCUUAAUGUAAUGCCAUUAGUGCA | 258 | UGCACUAAUGGCAUACUAAGAUUC | 318 | 36.00 | 15082 |
| CCAUUAGUGCAAAGAAUAUGAGCUG | 259 | CGAGCUCUAUUCUUUGCACUAAUGG | 319 | 44.00 | 15096 |
| GAAUAGAGCUCGCACCGUAGCUGGU | 260 | ACCAGCUACGGUGCGAGCUCUAUUC | 320 | 56.00 | 15109 |
| CACCGUAGCUGGUGUCUAUCUGU | 261 | ACAGAUAGAGACACCAGCUACGGUG | 321 | 52.00 | 15121 |
| GCUGGUGUCUAUCUGUAGUACUA | 262 | UAGUACUACAGAUAGAGACACCAGC | 322 | 44.00 | 15128 |

Figure 20 (Table 2)

| siRNA Sequence (sense): (5'-3') | SEQ ID NO. | siRNA Sequence (anti-sense): (5'-3') | SEQ ID NO: | G/C content | Start base in 2019-nCoV Sequence |
|---|---|---|---|---|---|
| CAAUGGUACUAAGAGGUUUdTdT | 324 | AAACCUCUUAGUACCAUUGdTdT | 358 | 36.84% | 21781 |
| UCUUAUGGACCUUGAAGGAdTdT | 325 | UCCUUCAAGGUCCAUAAGAdTdT | 359 | 42.11% | 22087 |
| UUCUUCUUCAGGUUGGACAdTdT | 326 | UGUCCAACCUGAAGAAGAAdTdT | 360 | 42.11% | 22321 |
| UGAAAAUGGAACCAUUACAdTdT | 327 | UGUAAUGGUUCCAUUUUCAdTdT | 370 | 31.58% | 22402 |
| AGUUUUUAACGCCACCAGAdTdT | 328 | UCUGGUGGCGUUAAAAACUdTdT | 371 | 42.11% | 22582 |
| ACCUUGUAAUGGUGUUGAAdTdT | 440 | UUCAACACCAUUACAAGGUdTdT | 372 | 36.84% | 22996 |
| CAACUUCAAUGGUUUAACAdTdT | 330 | UGUUAAACCAUUGAAGUUGdTdT | 373 | 31.58% | 23185 |
| GAUUCUUGACAUUACACCAdTdT | 331 | UGGUGUAAUGUCAAGAAUCdTdT | 374 | 36.84% | 23311 |
| CAGUGUUAUAACACCAGGAdTdT | 332 | UCCUGGUGUUAUAACACUGdTdT | 375 | 42.11% | 23347 |
| GGAUGUUAACUGCACAGAAdTdT | 333 | UUCUGUGCAGUUAACAUCCdTdT | 376 | 42.11% | 23401 |
| CUCAUAUGAGUGUGACAUAdTdT | 334 | UAUGUCACACUCAUAUGAGdTdT | 377 | 36.84% | 23536 |
| AUGCGCUAGUUAUCAGACUdTdT | 335 | AGUCUGAUAACUAGCGCAUdTdT | 378 | 42.11% | 23572 |
| GUCACUUGGUGCAGAAAAUdTdT | 336 | AUUUUCUGCACCAAGUGACdTdT | 379 | 42.11% | 23653 |
| UGCAGAAAAUUCAGUUGCUdTdT | 337 | AGCAACUGAAUUUUCUGCAdTdT | 380 | 36.84% | 23662 |
| GACAUCAGUAGAUUGUACAdTdT | 338 | UGUACAAUCUACUGAUGUCdTdT | 381 | 36.84% | 23761 |
| GCAAUAUGGCAGUUUUUGUdTdT | 339 | ACAAAAACUGCCAUAUUGCdTdT | 382 | 36.84% | 23824 |
| CCAAGAAGUUUUUGCACAAdTdT | 340 | UUGUGCAAAAACUUCUUGGdTdT | 383 | 36.84% | 23896 |
| CAACAAAGUGACACUUGCAdTdT | 341 | UGCAAGUGUCACUUUGUUGdTdT | 384 | 42.11% | 24031 |
| CACAGAUGAAAUGAUUGCUdTdT | 342 | AGCAAUCAUUUCAUCUGUGdTdT | 385 | 36.84% | 24157 |
| GUUAGCGGGUACAAUCACUdTdT | 343 | AGUGAUUGUACCCGCUAACdTdT | 386 | 47.37% | 24193 |
| CUAUUGGCAAAAUUCAAGAdTdT | 344 | UCUUGAAUUUUGCCAAUAGdTdT | 387 | 31.58% | 24355 |
| UUCAAGAUGUGGUCAACCAdTdT | 345 | UGGUUGACCACAUCUUGAAdTdT | 388 | 42.11% | 24409 |
| UGGUCAACCAAAAUGCACAdTdT | 346 | UGUGCAUUUUGGUUGACCAdTdT | 389 | 42.11% | 24418 |
| UUGACAAAGUUGAGGCUGAdTdT | 347 | UCAGCCUCAACUUUGUCAAdTdT | 390 | 42.11% | 24517 |

Figure 20 (Table 2) (continued)

| | | | | |
|---|---|---|---|---|
| GCAGACUUCAAAGUUUGCAdTdT | 348 | UGCAAACUUUGAAGUCUGCdTdT | 391 | 42.11% | 24562 |
| GACAAUCAAAAGAGUUGAdTdT | 349 | UCAACUCUUUUUGAUUGUCdTdT | 392 | 31.58% | 24670 |
| CCAUUGUCAUGAUGGAAAdTdT | 350 | UUUCCAUCAUGACAAAUGGdTdT | 393 | 36.84% | 24805 |
| AUGGCACCACUGGUUUGUdTdT | 351 | ACAAACCAGUGUGCCAUdTdT | 394 | 47.37% | 24859 |
| CUACAGACAACACAUUUGUdTdT | 352 | ACAAAUGUGUUGUCUGUAGdTdT | 395 | 36.84% | 24913 |
| CUUUGCAACCUGAAUUAGAdTdT | 353 | UCUAAUUCAGGUUGCAAAGdTdT | 396 | 36.84% | 24985 |
| CUGGCAUUAAAUGCUUCAGdTdT | 354 | ACUGAAGCAUUAAAUGCCAGdTdT | 397 | 42.11% | 25075 |
| ACAUUUGGCUAGGUUUUAUdTdT | 355 | AUAAAACCUAGCCAAAUGUdTdT | 398 | 31.58% | 25210 |
| GAUCCUGCUGCAAAUUUGAdTdT | 356 | UCAAAUUUGCAGCAGGAUCdTdT | 399 | 42.11% | 25318 |
| GCAAAUUUGAUGAAGACGAdTdT | 357 | UCGUCUUCAUCAAAUUUGCdTdT | 400 | 36.84% | 25327 |

Figure 21 (Table 3)

| siRNA Name | SEQ ID NO: | sense strand (5'-3') | anti-sense strand (5'-3') | SEQ ID NO: |
|---|---|---|---|---|
| target ORF1AB | | | | |
| SCo1 | 1 | GAAAACACGUCCAACUCAGUUUG | CAAACUGAGUUGGACGUGUUUUC | 102 |
| SCo2 | 2 | CUCUGAAGAAGUAGUGGAAAAUCCU | AGGAUUUUCCACUACUUCUUCAGAG | 103 |
| SCo3 | 3 | GAUCUGAGGACAAGAGGGCAAAAGU | ACUUUUGCCCUCUGUCCUCAGAUC | 104 |
| SCo4 | 4 | CAGAACUGGAACCACCUUGUAGGUU | AACCUACAAGGUGGUUCCAGUUCUG | 105 |
| SCo5 | 5 | CCUUGUAGGUUUGUAACAGACACAC | GUGUGUCUGUAACAAACCUACAAGG | 106 |
| SCo6 | 6 | GUGGAAAGGUUAUGGCUGUAGUUGU | ACAACUACAGCCAUAACCUUUCCAC | 107 |
| SCo7 | 7 | GUGCGGGCACAGGCACUAGUACUGAU | AUCAGUACUAGUGCCUGUGCCGCAC | 108 |
| SCo8 | 8 | CACCUACAAGUUUUGGACCACUAGU | ACUAGUGGUCCAAAACUUGUAGGUG | 109 |
| SCo9 | 9 | CAAUGAGUUAUGAGGAUCAAGAUGC | GCAUCUUGAUCCUCAUAACUCAUUG | 110 |
| SCo10 | 10 | GAACUUAAGUAGUAUGCCAUUAGUGCA | UGCACUAAUGGCAUACUUAAGAUUC | 111 |
| SCo11 | 11 | CCAUUAGUGCAAAGAAUAGAGCUCG | CGAGCUCUAUUCUUUGCACUAAUGG | 112 |
| SCo12 | 12 | CACCGUAGCUGGUGUCUCUAUCUGU | ACAGAUAGAGACACCAGCUACGGUG | 113 |
| SCo13 | 13 | GACTGAGACTGACCTTACTAAAGGA | UCCUUUAGUAAGGUCAGUCUCAGUC | 114 |
| SCo14 | 14 | CCUAAUCAGGAGUAUGCUGAUGUCU | AGACAUCAGCAUACUCCUGAUUAGG | 115 |
| SCo15 | 15 | GAAAAAGGUGACUAUGGUGAUGCUG | CAGCAUCACCAUAGUCACCUUUUUC | 116 |
| SCo16 | 16 | GCAAUGUUGCAAAUUAUCAAAAGGU | ACCUUUUGAUAAUUUGCAACAUUGC | 117 |
| SCo17 | 17 | GGACCACUGGGUACUGGUAAGAGUC | GACUCUUACCAGUACCAGGUGGUCC | 118 |
| SCo18 | 18 | CAUCCUACACAGGCCACUACACACC | GGUGUGUAGGUGCCUGUGUAGGAUG | 119 |
| SCo19 | 19 | CAUAACAGAGAUGCGCAAACAGGUUCA | UGAACCUGUUUGCGCAUCUGUUAUG | 120 |

Figure 21 (Table 3) (continued)

| | | | | |
|---|---|---|---|---|
| SCo20 | 20 | GUGUCUUUAGCUAUAGAUGCUUACC | GGUAAGCAUCUAUAGCUAAAGACAC | 121 |
| SCo21 | 21 | CAUUUGGUGCUGGUUCUGAUAAAG | CUUUAUCAGAACCAGCACCAAAAUG | 122 |
| SCo22 | 22 | CUUGAACAGCCCUAUGUGdTdT | ACACAUAGGGCUGUUUCAAGdTdT | 123 |
| SCo23 | 23 | GAAAACUACCGAAGUUGUAdTdT | UACAACUUCGGUAGUUUUCdTdT | 124 |
| SCo24 | 24 | CACCUUAUGGGUUGGGAUUdTdT | AAUCCCAACCCAUAAGGUGdTdT | 125 |
| SCo25 | 25 | CCUUACCCAGAUCCAUCAAdTdT | UUGAUGGAUCUGGGUAAGGdTdT | 126 |
| SCo26 | 26 | GCACACUAGAACCAGAAUAdTdT | UAUUCUGGUUCUAGUGUGCdTdT | 127 |
| SCo27 | 27 | GGUGAACGUGUACGCCAAGdTdT | CUUGGCGUACACGUUCACCdTdT | 128 |
| SCo28 | 28 | CUUAUGGGUUGGGAUUAUCdTdT | GAUAAUCCCAACCCAUAAGdTdT | 129 |
| Negative control siRNA | | | | |
| SCo29 | 29 | GUGAUUCUUAAACUUCGUUGCGUGG | CCACGCAACGAAGUUUAAGAAUCAC | 130 |
| SCo30 | 30 | GUUCCUUUAGUAUAUUUUGdTdT | ACAAAUAUACUAAAGGAACdTdT | 131 |
| target S gene | | | | |
| SCo31 | 31 | CAAUGGUACUAAGAGGUUUdTdT | AAACCUCUUAGUACCAUUGdTdT | 132 |
| SCo32 | 32 | GAAGUCUAAAUCUCAAACCUdTdT | AGGUUUGAGAUUAGACUUCdTdT | 133 |
| SCo33 | 33 | CCAACAAUUGGCAGAGACUdTdT | GUCUCUGCCAAUUGUUGGdTdT | 134 |
| SCo34 | 34 | CAUUGCUGACACUACUGAUdTdT | AUCAGUAGUGUCAGCAAUGdTdT | 135 |
| SCo35 | 35 | GAUUCUUGACAUUACACCAdTdT | UGGUGUAAUGUCAAGAAUCdTdT | 136 |
| SCo36 | 36 | GGAUGUUAACUGCACAGAAdTdT | UUCUGUGCAGUUAACAUCCdTdT | 137 |
| SCo37 | 37 | CUCAUAUGAGUGACAUAdTdT | UAUGUCACUCAUAUGAGdTdT | 138 |
| SCo38 | 38 | GUGUGACAUACCCAUUGGUdTdT | ACCAAUGGGUAUGUCACACdTdT | 140 |

Figure 21 (Table 3) (continued)

| | | | | |
|---|---|---|---|---|
| SCo39 | 39 | CUACACUAUGUCACUUGGUdTdT | ACCAAGUGACAUAGUGUAGdTdT | 141 |
| SCo40 | 40 | GUCACUUGGUGCAGAAAAUdTdT | AUUUUCUGCACCAAGUGACdTdT | 142 |
| SCo41 | 41 | GACAUCAGUAGAUUGUACAdTdT | UGUACAAUCUACUGAUGUCdTdT | 143 |
| SCo42 | 42 | GCAAUAUGGCAGUUUUUGUdTdT | ACAAAAACUGCCAUAUUGCdTdT | 144 |
| SCo43 | 43 | CAAAAACACCCAAGAAGUUdTdT | AACUUCUUGGGUGUUUUUGdTdT | 145 |
| SCo44 | 44 | CCAAGAAGUUUUGCACAAdTdT | UUGUGCAAAAACUUCUUGGdTdT | 146 |
| SCo45 | 45 | GAGGUCAUUAUUGAAGAUdTdT | AUCUUCAAUAAUGACCUCdTdT | 147 |
| SCo46 | 46 | CAACAAAGUGACACUUGCAdTdT | UGCAAGUGUCACUUUGUUGdTdT | 148 |
| SCo47 | 47 | CUUCAUCAAACAAUAUGGUdTdT | ACCAUAUUGUUUGAUGAAGdTdT | 149 |
| SCo48 | 48 | CACAGAUGAAAUGAUUGCUdTdT | AGCAAUCAUUUCAUCUGUGdTdT | 150 |
| SCo49 | 49 | GUUAGCGGUACAAUCACUdTdT | AGUGAUUGUACCCGCUAACdTdT | 151 |
| SCo50 | 50 | CCAAAAAUUGAUUGCCAA.dTdT | .UUGGCAAUCAAUUUUGGdTdT | 152 |
| SCo51 | 51 | CUAUUGGCAAAUUCAAGAdTdT | UCUUGAAUUUUGCCAAUAGdTdT | 153 |
| SCo52 | 52 | CAAGUGCACUUGGAAAACUdTdT | AGUUUCCAAGUGCACUUGdTdT | 154 |
| SCo53 | 53 | GCAGACUUCAAGUUUUGCdTdT | UGCAAAACUUGAAGUCUGCdTdT | 155 |
| SCo54 | 54 | GUUACUUGGACAAUCAAAdTdT | UUUGAUUGUCCAAGUACACdTdT | 156 |
| SCo55 | 55 | GACAAUCAAAAAGAGUUGAdTdT | UCAACUCUUUUGAUUGUCdTdT | 157 |
| SCo56 | 56 | GAAAGGGCUAUCAUCUUAUdTdT | AUAAGAUGAUAGCCCUUUCdTdT | 158 |
| SCo57 | 57 | CACCUCAUGGUGUAGUCUUdTdT | AAGACUACACCAUGAGGUGdTdT | 439 |
| SCo58 | 58 | GUGUAGUCUUCUUGCAUGUdTdT | ACAUGCAAGAGACUACACdTdT | 159 |
| SCo59 | 59 | CCAUUGUCAUGAUGGAAAdTdT | UUUCCAUCAUGACAAUGGdTdT | 160 |

Figure 21 (Table 3) (continued)

| | | | |
|---|---|---|---|
| SCo60 | 60 | GGAAUUUUAUGAACCACAdTdT | UGUGGUUCAUAAAAAUUCCdTdT | 161 |
| SCo61 | 61 | CUACAGACAACACAUUUGUdTdT | ACAAAUGUUGUCUGUAGdTdT | 162 |
| SCo62 | 62 | GAAUUGUCAACAACACAGUdTdT | ACUGUGUUGUUGACAAUUCdTdT | 163 |
| SCo63 | 63 | CUUUGCAACCUGAAUUAGAdTdT | UCUAAUUCAGGUUGCAAAGdTdT | 164 |
| SCo64 | 64 | CUGAAUUAGACUCAUUCAAdTdT | UUGAAUGAGUCUAAUUCAGdTdT | 165 |
| SCo65 | 65 | GUGACACUCUGGCAUUAAdTdT | UUAAUGCCAGAGUGUCACdTdT | 166 |
| SCo66 | 66 | CUGGCAUUAAUGCUUCAGUdTdT | ACUGAAGCAUUAAUGCCAGdTdT | 167 |
| SCo67 | 67 | GUUGCUGUAGUUGUCUCAAdTdT | UUGAGACAACUACAGCAACdTdT | 168 |
| SCo68 | 68 | GAUCCUGCAAAAUUUGdTdT | UCAAAUUUGCAGCAGGAUCdTdT | 169 |
| SCo69 | 69 | GCAAAUUGAUGAGAGACGdTdT | UCGUCUCAUCAAAUUUGCdTdT | 170 |
| guangzhou1 | 70 | CCUAAUAUUACAAACUUGUdTdT | ACAAGUUUGUAAUAUUAGGdTdT | 171 |
| guangzhou2 | 71 | CUAAUAUUACAAACUGUGdTdT | CACAAGUUUGUAAUAUUAGdTdT | 172 |
| guangzhou3 | 72 | CAUUCAAAAAGAAAUGACdTdT | GUCAAAUUCUUUUGAAUGdTdT | 173 |
| guangzhou4 | 73 | GUCAAAUUACAACACAUdTdT | AUGUAAUGUAAUUGACdTdT | 174 |
| guangzhou5 | 74 | CAAGUCAAACAAAUUACAdTdT | UGUAAUUUGUUUGACUUGdTdT | 175 |
| guangzhou6 | 75 | GUGGUUUUAAUUUUUCACAdTdT | UGUGAAAAAUUAAAACCACdTdT | 176 |
| guangzhou7 | 76 | CUAUGCAGAUUCAUUUGUAdTdT | UACAAAUGAAUCUGCAUAGdTdT | 177 |
| guangzhou8 | 77 | CUUGUUAAACAACUUAGCUdTdT | AGCUAAGUUGUUUAACAAGdTdT | 178 |
| guangzhou9 | 78 | GUUCUAUGAGAACCAAAdTdT | UUUGGUUCUCAUAGAGAACdTdT | 179 |
| guangzhou10 | 79 | GGUUGCUGAUUAUUCUGUdTdT | ACAGAAUAAUCAGCAACACdTdT | 180 |
| guangzhou11 | 80 | GUCUAUGCAGAUUCAUUUGdTdT | CAAAUGAAUCUGCAUAGACdTdT | 181 |

Figure 21 (Table 3) (continued)

| | | | | |
|---|---|---|---|---|
| guangzhou12 | 81 | CUAAUCUUGCUGCUACUAAdGdTdT | UUAGUAGCAGCAAGAUUAGdTdT | 182 |
| guangzhou13 | 82 | CUUGCUGCUACUAAAAUGUdGdTdT | ACAUUUAGUAGCAGCAAGdTdT | 183 |
| guangzhou14 | 83 | UCAAAAAGAAAUUGACCGCdTdT | GCGGUCAAUUCUUUUUGAdTdT | 184 |
| guangzhou15 | 84 | CUUGGACAAUCAAAAGAGdTdT | CUCUUUUUGAUUGUCCAAGdTdT | 185 |
| guangzhou16 | 85 | GGACAAUCAAAAGAGUUGdTdT | CAACUCUUUUGAUUGUCCdTdT | 186 |
| guangzhou17 | 86 | GUGGUUUUAAUUUUCACAAAUAUU | AAUAUUUGUGAAAAAUUAAAACCAC | 187 |
| guangzhou18 | 87 | GGUUUUAAUUUUCACAAAUAUUAC | GUAAUAUUUGUGAAAAAUUAAACC | 188 |
| guangzhou19 | 88 | GUUUUAAUUUUCACAAAUAUUACC | GGUAAUAUUUGUGAAAAAUUAAAAC | 189 |
| guangzhou20 | 89 | GGUGUUUUAAUUUUUCACAAAAAU | AUAUUUGUGAAAAAUUAAAACCACC | 190 |
| guangzhou21 | 90 | CUGCUAAUCUUGCUGCUACUAAAAU | AUUUUAGCAGCAAGAUUAGCAG | 191 |
| guangzhou22 | 91 | GCUAAUCUUGCUGCUACUAAAAUGU | ACAUUUAGUAGCAGCAAGAUUAGC | 192 |
| guangzhou23 | 92 | CUAAUCUUGCUGCUACUAAAAUGUC | GACAUUUAGUAGCAGCAAGAUUAG | 193 |
| guangzhou24 | 93 | CAAAUACCAUUUGCUAUGCAAAUGG | CCAUUUGCAUAGCAAAUGGUAUUUG | 194 |
| guangzhou25 | 94 | UGCUAAUCUUGCUGCUACUAAAAUG | CAUUUAGUAGCAGCAAGAUUAGCA | 195 |
| guangzhou26 | 95 | AACAUUCAAAAGAAAUUGACCGCC | GGCGGUCAAUUCUUUUGAAUGUU | 196 |
| guangzhou27 | 96 | AAAUACCAUUUGCUAUGCAAAUGGC | GCCAUUUGCAUAGCAAAUGGUAUUU | 197 |
| guangzhou28 | 97 | AUUUUGGUGGUUUUAAUUUUUCACA | UGUGAAAAAUUAAAACCACCAAAAU | 198 |
| guangzhou29 | 98 | UUUUGGUGGUUUUAAUUUUUCACAA | UUGUGAAAAAUUAAAACCACCAAAA | 199 |
| guangzhou30 | 99 | UUUGGUGGUUUUAAUUUUUCACAAA | UUUGUGAAAAAUUAAAACCACCAAA | 200 |
| guangzhou31 | 100 | UUGGUGGUUUUAAUUUUUCACAAAU | AUUUGUGAAAAAUUAAAACCACCAA | 201 |
| guangzhou32 | 101 | UCUGCUAAUCUUGCUGCUACUAAAA | UUUUAGUAGCAGCAAGAUUAGCAGA | 202 |

SEQUENCE LISTING

```
<160> NUMBER OF SEQ ID NOS: 440

<210> SEQ ID NO 1
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gaaaacacac guccaacuca guuug                                                25

<210> SEQ ID NO 2
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cucugaagaa guaguggaaa auccu                                               25

<210> SEQ ID NO 3
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gaucugagga caagagggca aaagu                                               25

<210> SEQ ID NO 4
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
cagaacugga accaccuugu agguu                                               25

<210> SEQ ID NO 5
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
ccuuguaggu uuguuacaga cacac                                               25

<210> SEQ ID NO 6
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
guggaaaggu uauggcugua guugu                                               25

<210> SEQ ID NO 7
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gugcggcaca ggcacuagua cugau                                               25

<210> SEQ ID NO 8
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
caccuacaag uuuuggacca cuagu                                              25

<210> SEQ ID NO 9
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
caaugaguua ugaggaucaa gaugc                                              25

<210> SEQ ID NO 10
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gaaucuuaag uaugccauua gugca                                              25

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccauuagugc aaagaauaga gcucg                                              25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
caccguagcu ggugucucua ucugu                                              25

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gactgagact gaccttacta aagga                                              25

<210> SEQ ID NO 14
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 14
ccuaaucagg aguaugcuga ugucu                                              25

<210> SEQ ID NO 15
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
gaaaaaggug acuaugguga ugcug                                              25

<210> SEQ ID NO 16
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
gcaauguugc aaauuaucaa aaggu                                              25

<210> SEQ ID NO 17
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 17
ggaccaccug guacugguaa gaguc                                              25

<210> SEQ ID NO 18
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 18
cauccuacac aggcaccuac acacc                                              25

<210> SEQ ID NO 19
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 19
cauaacagau gcgcaaacag guuca                                              25

<210> SEQ ID NO 20
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 20
gugucuuuag cuauagaugc uuacc                                              25

<210> SEQ ID NO 21
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21 cauuuggug cugguucuga uaaag                                               25

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
cuugaacagc ccuaugugut t                                                  21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
gaaaacuacc gaaguuguat t                                                  21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 24
caccuuaugg guugggauut t                                                  21

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 25
ccuuacccag auccaucaat t                                              21

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
gcacacuaga accagaauat t                                              21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
ggugaacgug uacgccaagt t                                              21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28
cuuauggguu gggauuauct t                                              21

<210> SEQ ID NO 29
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
gugauucuua aacuucguug cgugg                                          25

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 30
guuccuuuag uauauuugut t                                              21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 31
caaugguacu aagagguuut t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32
gaagucuaau cucaaaccut t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
ccaacaauuu ggcagagact t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
cauugcugac acuacugaut t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 35
gauucuugac auuacaccat t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ggauguuaac ugcacagaat t                                              21

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
cucauaugag ugugacauat t                                              21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
gugugacaua cccauuggut t                                              21

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cuacacuaug ucacuuggut t                                              21

<210> SEQ ID NO 40
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 40
gucacuuggu gcagaaaaut t                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
gacaucagua gauuguacat t                                              21

<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
gcaauauggc aguuuuugut t                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
caaaaacacc caagaaguut t                                              21

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 44
ccaagaaguu uuugcacaat t                                              21

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 45
gaggucauuu auugaagaut t                                              21

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
caacaaagug acacuugcat t                                              21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
cuucaucaaa caauauggut t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
cacagaugaa augauugcut t                                              21

<210> SEQ ID NO 49
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 49
guuagcgggu acaaucacut t                                              21

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 50
ccaaaaauug auugccaatt                                                    20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cuauuggcaa aauucaagat t                                                  21

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 52
caagugcacu uggaaaacut t                                                  21

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
gcagacuuca aaguuugcat t                                                  21

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 54
guguacuugg acaaucaaat t                                                  21

<210> SEQ ID NO 55
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 55
gacaaucaaa aagaguugat t                                              21

<210> SEQ ID NO 56
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
gaaagggcua ucaucuuaut t                                              21

<210> SEQ ID NO 57
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
caccucaugg uguagucuut t                                              21

<210> SEQ ID NO 58
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
guguagucuu cuugcaugut t                                              21

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
ccauuuguca ugauggaaat t                                              21

<210> SEQ ID NO 60
<211> LENGTH: 21
<212> TYPE: DNA
<213> ORGANISM: Artificial Sequence
<220> FEATURE:

<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
ggaauuuuua ugaaccacat t                                        21

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 61
cuacagacaa cacauuugut t                                        21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
gaauugucaa caacacagut t                                        21

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
cuuugcaacc ugaauuagat t                                        21

<210> SEQ ID NO 64
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
cugaauuaga cucauucaat t                                        21

<210> SEQ ID NO 65
<211> LENGTH: 21
<212> TYPE: DNA
<213> ORGANISM: Artificial Sequence -continued

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 65
gugacaucuc uggcauuaat t                                              21

<210> SEQ ID NO 66
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 66
cuggcauuaa ugcuucagut t                                              21

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 67
guugcuguag uugucucaat t                                              21

<210> SEQ ID NO 68
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 68
gauccugcug caaauuugat t                                              21

<210> SEQ ID NO 69
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 69
gcaaauuuga ugaagacgat t                                              21

<210> SEQ ID NO 70
<211> LENGTH: 21
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 70
ccuaauauua caaacuugut t         21

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 71
cuaauauuac aaacuugugt t         21

<210> SEQ ID NO 72
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 72
cauucaaaaa gaaauugact t         21

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 73
gucaaauuac auuacacaut t         21

<210> SEQ ID NO 74
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 74
caagucaaac aaauuuacat t         21

<210> SEQ ID NO 75
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75
gugguuuuaa uuuuucacat t                                                  21

<210> SEQ ID NO 76
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
cuaugcagau ucauuuguat t                                                  21

<210> SEQ ID NO 77
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 77
cuuguuaaac aacuuagcut t                                                  21

<210> SEQ ID NO 78
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 78
guucucuaug agaaccaaat t                                                  21

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
guguugcuga uuauucugut t                                                  21

<210> SEQ ID NO 80
```

<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 80
gucuaugcag auucauuugt t                                              21

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 81
cuaaucuugc ugcuacuaat t                                              21

<210> SEQ ID NO 82
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 82
cuugcugcua cuaaaaugut t                                              21

<210> SEQ ID NO 83
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 83
ucaaaaagaa auugaccgct t                                              21

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 84
cuuggacaau caaaaagagt t                                              21

```
<210> SEQ ID NO 85
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
ggacaaucaa aaagaguugt t                                                   21

<210> SEQ ID NO 86
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 86
gugguuuuaa uuuuucacaa auauu                                               25

<210> SEQ ID NO 87
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
gguuuuaauu uuucacaaau auuac                                               25

<210> SEQ ID NO 88
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 88 guuuaauuu ucacaaaua uuacc                                                 25

<210> SEQ ID NO 89
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 89
ggugguuuua auuuucaca aauau                                                25

<210> SEQ ID NO 90
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 90
cugcuaaucu ugcugcuacu aaaau                                               25
```

<210> SEQ ID NO 91
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
gcuaaucuug cugcuacuaa aaugu                                          25

<210> SEQ ID NO 92
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cuaaucuugc ugcuacuaaa auguc                                          25

<210> SEQ ID NO 93
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 93
caaauaccau uugcuaugca aaugg                                          25

<210> SEQ ID NO 94
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 94
ugcuaaucuu gcugcuacua aaaug                                          25

<210> SEQ ID NO 95
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 95
aacauucaaa aagaaauuga ccgcc                                          25

<210> SEQ ID NO 96
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 96
aaauaccauu ugcuaugcaa auggc                                          25

<210> SEQ ID NO 97
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 97
auuuuggugg uuuuaauuuu ucaca                                      25

<210> SEQ ID NO 98
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 98
uuuugguggu uuuaauuuuu cacaa                                      25

<210> SEQ ID NO 99
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 99
uuuggugguu uuaauuuuuc acaaa                                      25

<210> SEQ ID NO 100
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 100
uuggugguuu uaauuuuuca caaau                                      25

<210> SEQ ID NO 101
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
ucugcuaauc uugcugcuac uaaaa                                      25

<210> SEQ ID NO 102
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
caaacugagu uggacgugug uuuuc                                      25

```
<210> SEQ ID NO 103
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 103
aggauuuucc acuacuucuu cagag                                          25

<210> SEQ ID NO 104
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 104
acuuuugccc ucuuguccuc agauc                                          25

<210> SEQ ID NO 105
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 105
aaccuacaag gugguuccag uucug                                          25

<210> SEQ ID NO 106
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 106
gugugucugu aacaaaccua caagg                                          25

<210> SEQ ID NO 107
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 107
acaacuacag ccauaaccuu uccac                                          25

<210> SEQ ID NO 108
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 108
aucaguacua gugccugugc cgcac                                          25

<210> SEQ ID NO 109
```

<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 109
acuagugguc caaaacuugu aggug                25

<210> SEQ ID NO 110
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 110
gcaucuugau ccucauaacu cauug                25

<210> SEQ ID NO 111
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 111
ugcacuaaug gcauacuuaa gauuc                25

<210> SEQ ID NO 112
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 112
cgagcucuau ucuuugcacu aaugg                25

<210> SEQ ID NO 113
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 113
acagauagag acaccagcua cggug                25

<210> SEQ ID NO 114
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 114
uccuuuagua aggucagucu caguc                25

<210> SEQ ID NO 115
<211> LENGTH: 25

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 115
agacaucagc auacuccuga uuagg                                              25

<210> SEQ ID NO 116
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 116
cagcaucacc auagucaccu uuuuc                                              25

<210> SEQ ID NO 117
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 117 accuuugau aauuugcaac auugc                                               25

<210> SEQ ID NO 118
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
gacucuuacc aguaccaggu ggucc                                              25

<210> SEQ ID NO 119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
gguguguagg ugccugugua ggaug                                              25

<210> SEQ ID NO 120
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
ugaaccuguu ugcgcaucug uuaug                                              25

<210> SEQ ID NO 121
<211> LENGTH: 25
<212> TYPE: RNA
```

<213> ORGANISM: Artificial Sequence
<220> FEATURE:
<223> OTHER INFORMATION: Description of Artificial Sequence: Synthetic
    oligonucleotide

<400> SEQUENCE: 121
gguaagcauc uauagcuaaa gacac                                    25

<210> SEQ ID NO 122
<211> LENGTH: 25
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 122
cuuuaucaga accagcacca aaaug                                    25

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 123
acacauaggg cguucaagt t                                         21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 124
uacaacuucg guaguuuuct t                                        21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 125
aaucccaacc cauaaggugt t                                        21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:

```
<223> OTHER INFORMATION: Description of Combined DNA/RNA Molecule:
      Synthetic oligonucleotide

<400> SEQUENCE: 126
uugauggauc uggguaaggt t                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
uauucugguu cuagugugct t                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
cuuggcguac acguucacct t                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
gauaauccca acccauaagt t                                              21

<210> SEQ ID NO 130
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
ccacgcaacg aaguuuaaga aucac                                          25

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 131
acaaauauac uaaaggaact t                                              21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132
aaaccucuua guaccauugt t                                              21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
agguuugaga uuagacuuct t                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
gucucugcca aauuguuggt t                                              21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
aucaguagug ucagcaaugt t                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 136
ugguguaaug ucaagaauct t                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
uucugugcag uuaacaucct t                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
uaugucacac ucauaugagt t                                              21

<210> SEQ ID NO 139

<400> SEQUENCE: 139

000

<210> SEQ ID NO 140
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
accaaugggu augucacact t                                              21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
accaagugac auaguguagt t                                              21

<210> SEQ ID NO 142

-continued

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
auuuucugca ccaagugact t                                              21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
uguacaaucu acugauguct t                                              21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
acaaaaacug ccauauugct t                                              21

<210> SEQ ID NO 145
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
aacuucuugg guguuuuugt t                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
uugugcaaaa acuucuuggt t                                              21
```

```
<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
aucuucaaua aaugaccuct t                                                   21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
ugcaaguguc acuuuguugt t                                                   21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
accauauugu uugaugaagt t                                                   21

<210> SEQ ID NO 150
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
agcaaucauu ucaucugugt t                                                   21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
agugauugua cccgcuaact t                                                   21
```

```
<210> SEQ ID NO 152
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
uuggcaauca auuuuuggtt                                                   20

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
ucuugaauuu ugccaauagt t                                                 21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
aguuuuccaa gugcacuugt t                                                 21

<210> SEQ ID NO 155
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
ugcaaacuuu gaagucugct t                                                 21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
uuugauuguc caaguacact t                                                 21
```

```
<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
ucaacucuuu uugauuguct t                                              21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
auaagaugau agcccuuuct t                                              21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
acaugcaaga agacuacact t                                              21

<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
uuuccaucau gacaaauggt t                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
```
ugugguucau aaaaauucct t                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
acaaaugugu ugucuguagt t                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
acuguguugu ugacaauuct t                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
ucuaauucag guugcaaagt t                                              21

<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
uugaaugagu cuaauucagt t                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
uuaaugccag agaugucact t                     21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
acugaagcau uaaugccagt t                     21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
uugagacaac uacagcaact t                     21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
ucaaauuugc agcaggauct t                     21

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
ucgucuucau caaauuugct t                     21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 171
acaaguuugu aauauuaggt t                                          21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
cacaaguuug uaauauuagt t                                          21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
gucaauuucu uuugaaugt t                                           21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
auguguaaug uaauuugact t                                          21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
uguaaauuug uuugacuugt t                                          21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 176
ugugaaaaau uaaaaccact t                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
uacaaaugaa ucugcauagt t                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
agcuaaguug uuuaacaagt t                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179
uuugguucuc auagagaact t                                              21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
acagaauaau cagcaacact t                                              21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 181
caaaugaauc ugcauagact t            21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
uuaguagcag caagauuagt t            21

<210> SEQ ID NO 183
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
acauuuuagu agcagcaagt t            21

<210> SEQ ID NO 184
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 184
gcggucaauu ucuuuuugat t            21

<210> SEQ ID NO 185
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
cucuuuuuga uuguccaagt t            21

<210> SEQ ID NO 186
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 186
caacucuuuu ugauugucct t                                           21

<210> SEQ ID NO 187
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 187
aauauuugug aaaaauuaaa accac                                       25

<210> SEQ ID NO 188
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 188
guaauauuug ugaaaaauua aaacc                                       25

<210> SEQ ID NO 189
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 189
gguaauauuu gugaaaaauu aaaac                                       25

<210> SEQ ID NO 190
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 190
auauuuguga aaauuaaaa ccacc                                        25

<210> SEQ ID NO 191
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 191
auuuuaguag cagcaagauu agcag                                       25

<210> SEQ ID NO 192
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 192
acauuuuagu agcagcaaga uuagc                                              25

<210> SEQ ID NO 193
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 193
gacauuuuag uagcagcaag auuag                                              25

<210> SEQ ID NO 194
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 194
ccauuugcau agcaaauggu auuug                                              25

<210> SEQ ID NO 195
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 195 cauuuagua gcagcaagau uagca                                               25

<210> SEQ ID NO 196
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 196
ggcggucaau uucuuuuuga auguu                                              25

<210> SEQ ID NO 197
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 197
gccauuugca uagcaaaugg uauuu                                              25

<210> SEQ ID NO 198
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 198
ugugaaaaau uaaaaccacc aaaau                                    25

<210> SEQ ID NO 199
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 199
uugugaaaaa uuaaaaccac caaaa                                    25

<210> SEQ ID NO 200
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 200
uuugugaaaa auuaaaacca ccaaa                                    25

<210> SEQ ID NO 201
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 201
auuugugaaa aauuaaaacc accaa                                    25

<210> SEQ ID NO 202
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 202
uuuuaguagc agcaagauua gcaga                                    25

<210> SEQ ID NO 203
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
guucaacuua gugaaauuat t                                        21

<210> SEQ ID NO 204
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 204
cuugaacagc ccaugugut t                                              21

<210> SEQ ID NO 205
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
gaaaacuacc gaaguuguat t                                             21

<210> SEQ ID NO 206
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
gauguuguua gacaaugcut t                                             21

<210> SEQ ID NO 207
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
caugcagggu gcuguagact t                                             21

<210> SEQ ID NO 208
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
caccuuaugg guugggauut t                                             21

<210> SEQ ID NO 209
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 209
gccaugccua acaugcuuat t                                              21

<210> SEQ ID NO 210
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
ccuuacccag auccaucaat t                                              21

<210> SEQ ID NO 211
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
gcacacuaga accagaauat t                                              21

<210> SEQ ID NO 212
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
uaugacuaug ucauauucat t                                              21

<210> SEQ ID NO 213
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
cauuugagcu uugggcuaat t                                              21

<210> SEQ ID NO 214
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
gagucacauu aauuggagat t                                                    21

<210> SEQ ID NO 215
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 215
guucuucuuc guaagaacgg uaaua                                                25

<210> SEQ ID NO 216
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 216
caugugguag uguugguuuu aacau                                                25

<210> SEQ ID NO 217
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 217
gaucugagga caagagggca aaagu                                                25

<210> SEQ ID NO 218
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 218
caccuacaag uuuuggacca cuagu                                                25

<210> SEQ ID NO 219
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 219
cacuauaugu uaaaccaggu ggaac                                                25

<210> SEQ ID NO 220
```

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 220
cuugucgauu cagaucuuaa ugacu                                          25

<210> SEQ ID NO 221
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 221
gggcuagauu cccuaagagu gaugg                                          25

<210> SEQ ID NO 222
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 222
guggaaaggu uauggcugua guugu                                          25

<210> SEQ ID NO 223
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 223
gugacauggu accacauaua ucacg                                          25

<210> SEQ ID NO 224
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 224
caauagccgc cacuagagga gcuac                                          25

<210> SEQ ID NO 225
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 225
cauccuacac aggcaccuac acacc                                          25

<210> SEQ ID NO 226
<211> LENGTH: 25
```

<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 226
cuacacaggc accuacacac cucag                                              25

<210> SEQ ID NO 227
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 227
cauaacagau gcgcaaacag guuca                                              25

<210> SEQ ID NO 228
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 228
guuucuuuaa ggaaggaagu ucugu                                              25

<210> SEQ ID NO 229
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 229
ggaccaccug guacugguaa gaguc                                              25

<210> SEQ ID NO 230
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 230
ccugguacug guaagaguca uuuug                                              25

<210> SEQ ID NO 231
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 231
uacuuugauu guuacgaugg uggcu                                              25

<210> SEQ ID NO 232
<211> LENGTH: 25
<212> TYPE: RNA

<213> ORGANISM: Artificial Sequence
<220> FEATURE:
<223> OTHER INFORMATION: Description of Artificial Sequence: Synthetic
      oligonucleotide

<400> SEQUENCE: 232
gauuguuacg augguggcug uauua                                          25

<210> SEQ ID NO 233
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 233
caaugaguua ugaggaucaa gaugc                                          25

<210> SEQ ID NO 234
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 234
guuaugagga ucaagaugca cuuuu                                          25

<210> SEQ ID NO 235
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 235
ccuaaucagg aguaugcuga ugucu                                          25

<210> SEQ ID NO 236
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 236
gaguuuuaug aggcuaugua cacac                                          25

<210> SEQ ID NO 237
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 237
cucugaagaa guaguggaaa auccu                                          25

<210> SEQ ID NO 238
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 238
guaguggaaa auccuaccau acaga                                          25

<210> SEQ ID NO 239
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 239
caacgagaaa acacacgucc aacuc                                          25

<210> SEQ ID NO 240
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 240
gaaaacacac guccaacuca guuug                                          25

<210> SEQ ID NO 241
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 241
gggguaaggc uagacuuuau uauga                                          25

<210> SEQ ID NO 242
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 242
guccugcuga aauuguugac acugu                                          25

<210> SEQ ID NO 243
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 243
cagaacugga accaccuugu agguu                                          25

<210> SEQ ID NO 244
<211> LENGTH: 25
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 244
ccuuguaggu uuguuacaga cacac                                       25

<210> SEQ ID NO 245
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 245
cuuuucaaac ugucaaaccc gguaa                                       25

<210> SEQ ID NO 246
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 246
gcaaaatgtt ggactgagac tgacc                                       25

<210> SEQ ID NO 247
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 247
gactgagact gaccttacta aagga                                       25

<210> SEQ ID NO 248
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 248
gagaguacac cuuugaaaaa gguga                                       25

<210> SEQ ID NO 249
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 249 gaaaaggug acuaugguga ugcug                                        25

<210> SEQ ID NO 250
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 250
cucagaugag uuuucuagca auguu     25

<210> SEQ ID NO 251
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 251
gaugaguuuu cuagcaaugu ugcaa     25

<210> SEQ ID NO 252
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 252
gcaauguugc aaauuaucaa aaggu     25

<210> SEQ ID NO 253
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 253
guuuuuaaac ggguuugcgg uguaa     25

<210> SEQ ID NO 254
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 254
ggguuugcgg uguaagugca gcccg     25

<210> SEQ ID NO 255
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 255
guaagugcag cccgucuuac accgu     25

<210> SEQ ID NO 256
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 256
gugcggcaca ggcacuagua cugau                                          25

<210> SEQ ID NO 257
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 257
guaaugucau cccuacuaua acuca                                          25

<210> SEQ ID NO 258
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 258
gaaucuuaag uaugccauua gugca                                          25

<210> SEQ ID NO 259
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 259
ccauuagugc aaagaauaga gcucg                                          25

<210> SEQ ID NO 260
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 260
gaauagagcu cgcaccguag cuggu                                          25

<210> SEQ ID NO 261
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 261
caccguagcu ggugucucua ucugu                                          25

<210> SEQ ID NO 262
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide -continued

<400> SEQUENCE: 262
gcuggugucu cuaucuguag uacua					25

<210> SEQ ID NO 263
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
uaauuucacu aaguugaact t					21

<210> SEQ ID NO 264
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
acacauaggg cguucaagt t					21

<210> SEQ ID NO 265
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
uacaacuucg guaguuuct t					21

<210> SEQ ID NO 266
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
agcauugucu aacaacauct t					21

<210> SEQ ID NO 267
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
gucuacagca cccugcaugt t                                              21

<210> SEQ ID NO 268
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
aaucccaacc cauaaggugt t                                              21

<210> SEQ ID NO 269
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
uaagcauguu aggcauggct t                                              21

<210> SEQ ID NO 270
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
uugauggauc uggguaaggt t                                              21

<210> SEQ ID NO 271
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
uauucugguu cuagugugct t                                              21

<210> SEQ ID NO 272
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 272
ugaauaugac auagucauat t                                              21

<210> SEQ ID NO 273
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 273
uuagcccaaa gcucaaaugt t                                              21

<210> SEQ ID NO 274
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
ucuccaauua augugacuct t                                              21

<210> SEQ ID NO 275
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 275
uauuaccguu cuuacgaaga agaac                                          25

<210> SEQ ID NO 276
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 276
auguuaaaac caacacuacc acaug                                          25

<210> SEQ ID NO 277
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 277
acuuuugccc ucuugccuc agauc                                           25

<210> SEQ ID NO 278

```
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 278
acuagugguc caaaacuugu aggug                                               25

<210> SEQ ID NO 279
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 279
guuccaccug guuuaacaua uagug                                               25

<210> SEQ ID NO 280
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 280
agucauuaag aucugaaucg acaag                                               25

<210> SEQ ID NO 281
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 281
ccaucacucu uagggaaucu agccc                                               25

<210> SEQ ID NO 282
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 282
acaacuacag ccauaaccuu uccac                                               25

<210> SEQ ID NO 283
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 283
cgugauauau gugguaccau gucac                                               25

<210> SEQ ID NO 284
<211> LENGTH: 25
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 284
guagcuccuc uaguggcggc uauug                                              25

<210> SEQ ID NO 285
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 285
gguguguagg ugccugugua ggaug                                              25

<210> SEQ ID NO 286
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 286
cugaggugug uaggugccug uguag                                              25

<210> SEQ ID NO 287
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 287
ugaaccuguu ugcgcaucug uuaug                                              25

<210> SEQ ID NO 288
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 288
acagaacuuc cuuccuuaaa gaaac                                              25

<210> SEQ ID NO 289
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 289
gacucuuacc aguaccaggu ggucc                                              25

<210> SEQ ID NO 290
<211> LENGTH: 25
<212> TYPE: RNA
```

<213> ORGANISM: Artificial Sequence
<220> FEATURE:
<223> OTHER INFORMATION: Description of Artificial Sequence: Synthetic
      oligonucleotide

<400> SEQUENCE: 290
caaaaugacu cuuaccagua ccagg                                              25

<210> SEQ ID NO 291
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 291
agccaccauc guaacaauca aagua                                              25

<210> SEQ ID NO 292
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 292
uaauacagcc accaucguaa caauc                                              25

<210> SEQ ID NO 293
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 293
gcaucuugau ccucauaacu cauug                                              25

<210> SEQ ID NO 294
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
aaaagugcau cuugauccuc auaac                                              25

<210> SEQ ID NO 295
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
agacaucagc auacuccuga uuagg                                              25

<210> SEQ ID NO 296
<211> LENGTH: 25
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 296
guguguacau agccucauaa aacuc                                              25

<210> SEQ ID NO 297
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 297
aggauuuucc acuacuucuu cagag                                              25

<210> SEQ ID NO 298
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 298
ucuguauggu aggauuuucc acuac                                              25

<210> SEQ ID NO 299
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 299
gaguuggacg uguguuuucu cguug                                              25

<210> SEQ ID NO 300
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 300
caaacugagu uggacgugug uuuuc                                              25

<210> SEQ ID NO 301
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 301
ucauaauaaa gucuagccuu acccc                                              25

<210> SEQ ID NO 302
<211> LENGTH: 25
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 302
acagugucaa caauuucagc aggac                                            25

<210> SEQ ID NO 303
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 303
aaccuacaag gugguuccag uucug                                            25

<210> SEQ ID NO 304
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 304
gugugucugu aacaaaccua caagg                                            25

<210> SEQ ID NO 305
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 305
uuaccggguu ugacaguuug aaaag                                            25

<210> SEQ ID NO 306
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 306
ggucagucuc aguccaacau uuugc                                            25

<210> SEQ ID NO 307
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 307
uccuuuagua aggucagucu caguc                                            25

<210> SEQ ID NO 308
<211> LENGTH: 25
<212> TYPE: RNA
<213> ORGANISM: Artificial Sequence
<220> FEATURE:
<223> OTHER INFORMATION: Description of Artificial Sequence: Synthetic
``` oligonucleotide

<400> SEQUENCE: 308
ucaccuuuuu caaaggugua cucuc    25

<210> SEQ ID NO 309
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 309
cagcaucacc auagucaccu uuuuc    25

<210> SEQ ID NO 310
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 310
aacauugcua gaaaacucau cugag    25

<210> SEQ ID NO 311
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 311
uugcaacauu gcuagaaaac ucauc    25

<210> SEQ ID NO 312
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 312
accuuuugau aauuugcaac auugc    25

<210> SEQ ID NO 313
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 313
uuacaccgca aacccguuua aaaac    25

<210> SEQ ID NO 314
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 314
cgggcugcac uuacaccgca aaccc                                         25

<210> SEQ ID NO 315
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 315
acgguguaag acgggcugca cuuac                                         25

<210> SEQ ID NO 316
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 316
aucaguacua gugccugugc cgcac                                         25

<210> SEQ ID NO 317
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 317
ugaguuauag uagggaugac auuac                                         25

<210> SEQ ID NO 318
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 318
ugcacuaaug gcauacuuaa gauuc                                         25

<210> SEQ ID NO 319
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 319
cgagcucuau ucuuugcacu aaugg                                         25

<210> SEQ ID NO 320
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 320
accagcuacg gugcgagcuc uauuc                                         25

<210> SEQ ID NO 321
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 321
acagauagag acaccagcua cggug                                         25

<210> SEQ ID NO 322
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 322
uaguacuaca gauagagaca ccagc                                         25

<210> SEQ ID NO 323

<400> SEQUENCE: 323

000

<210> SEQ ID NO 324
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
caaugguacu aagagguuut t                                             21

<210> SEQ ID NO 325
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
ucuuauggac cuugaaggat t                                             21

<210> SEQ ID NO 326
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 326
uucuucuuca gguuggacat t                                              21

<210> SEQ ID NO 327
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
ugaaaaugga accauuacat t                                              21

<210> SEQ ID NO 328
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 328
aguuuuuaac gccaccagat t                                              21

<210> SEQ ID NO 329

<400> SEQUENCE: 329

000

<210> SEQ ID NO 330
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
caacuucaau gguuuaacat t                                              21

<210> SEQ ID NO 331
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
gauucuugac auuacaccat t                                              21

<210> SEQ ID NO 332

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
caguguuaua acaccaggat t                                              21

<210> SEQ ID NO 333
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 333
ggauguuaac ugcacagaat t                                              21

<210> SEQ ID NO 334
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
cucauaugag ugugacauat t                                              21

<210> SEQ ID NO 335
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
augcgcuagu uaucagacut t                                              21

<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
gucacuuggu gcagaaaaut t                                              21
```

```
<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
ugcagaaaau ucaguugcut t                                             21

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 338
gacaucagua gauuguacat t                                             21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
gcaauauggc aguuuuugut t                                             21

<210> SEQ ID NO 340
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
ccaagaaguu uuugcacaat t                                             21

<210> SEQ ID NO 341
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
caacaaagug acacuugcat t                                             21
```

<210> SEQ ID NO 342
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 342
cacagaugaa augauugcut t                                        21

<210> SEQ ID NO 343
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 343
guuagcgggu acaaucacut t                                        21

<210> SEQ ID NO 344
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 344
cuauuggcaa aauucaagat t                                        21

<210> SEQ ID NO 345
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 345
uucaagaugu ggucaaccat t                                        21

<210> SEQ ID NO 346
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 346
uggucaacca aaaugcacat t                                        21

```
<210> SEQ ID NO 347
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
uugacaaagu ugaggcugat t                                              21

<210> SEQ ID NO 348
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 348
gcagacuuca aaguuugcat t                                              21

<210> SEQ ID NO 349
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
gacaaucaaa aagaguugat t                                              21

<210> SEQ ID NO 350
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
ccauuuguca ugauggaaat t                                              21

<210> SEQ ID NO 351
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
```
auggcacaca cugguuugut t                                        21

<210> SEQ ID NO 352
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
cuacagacaa cacauuugut t                                        21

<210> SEQ ID NO 353
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
cuuugcaacc ugaauuagat t                                        21

<210> SEQ ID NO 354
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
cuggcauuaa ugcuucagut t                                        21

<210> SEQ ID NO 355
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
acauuuggcu agguuuuaut t                                        21

<210> SEQ ID NO 356
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356

```
gauccugcug caaauuugat t                                              21

<210> SEQ ID NO 357
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
gcaaauuuga ugaagacgat t                                              21

<210> SEQ ID NO 358
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
aaaccucuua guaccauugt t                                              21

<210> SEQ ID NO 359
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
uccuucaagg uccauaagat t                                              21

<210> SEQ ID NO 360
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
uguccaaccu gaagaagaat t                                              21

<210> SEQ ID NO 361

<400> SEQUENCE: 361

000

<210> SEQ ID NO 362

<400> SEQUENCE: 362
```

000

<210> SEQ ID NO 363
<400> SEQUENCE: 363
000

<210> SEQ ID NO 364
<400> SEQUENCE: 364
000

<210> SEQ ID NO 365
<400> SEQUENCE: 365
000

<210> SEQ ID NO 366
<400> SEQUENCE: 366
000

<210> SEQ ID NO 367
<400> SEQUENCE: 367
000

<210> SEQ ID NO 368
<400> SEQUENCE: 368
000

<210> SEQ ID NO 369
<400> SEQUENCE: 369
000

<210> SEQ ID NO 370
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
uguaaugguu ccauuuucat t                                              21

<210> SEQ ID NO 371
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371 ucuggggcg uuaaaaacut t                                        21

<210> SEQ ID NO 372
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
uucaacacca uuacaaggut t                                       21

<210> SEQ ID NO 373
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
uguuaaacca uugaaguugt t                                       21

<210> SEQ ID NO 374
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
ugguguaaug ucaagaauct t                                       21

<210> SEQ ID NO 375
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375 uccuggguu auaacacugt t                                        21

<210> SEQ ID NO 376
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 376
uucugugcag uuaacaucct t                                              21

<210> SEQ ID NO 377
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
uaugucacac ucauaugagt t                                              21

<210> SEQ ID NO 378
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378
agucugauaa cuagcgcaut t                                              21

<210> SEQ ID NO 379
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
auuuucugca ccaagugact t                                              21

<210> SEQ ID NO 380
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
agcaacugaa uuuucugcat t                                              21

<210> SEQ ID NO 381
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 381
uguacaaucu acugauguct t          21

<210> SEQ ID NO 382
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
acaaaaacug ccauauugct t          21

<210> SEQ ID NO 383
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 383
uugugcaaaa acuucuuggt t          21

<210> SEQ ID NO 384
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
ugcaaguguc acuuuguugt t          21

<210> SEQ ID NO 385
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
agcaaucauu ucaucugugt t          21

<210> SEQ ID NO 386
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 386
agugauugua cccgcuaact t                                                    21

<210> SEQ ID NO 387
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
ucuugaauuu ugccaauagt t                                                    21

<210> SEQ ID NO 388
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 388
ugguugacca caucuugaat t                                                    21

<210> SEQ ID NO 389
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 389
ugugcauuuu gguugaccat t                                                    21

<210> SEQ ID NO 390
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 390
ucagccucaa cuuugucaat t                                                    21

<210> SEQ ID NO 391
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 391
ugcaaacuuu gaagucugct t                                              21

<210> SEQ ID NO 392
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 392
ucaacucuuu uugauuguct t                                              21

<210> SEQ ID NO 393
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
uuuccaucau gacaaaggt t                                               21

<210> SEQ ID NO 394
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 394
acaaaccagu gugugccaut t                                              21

<210> SEQ ID NO 395
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 395 acaaugugu ugucuguagt t                                               21

<210> SEQ ID NO 396
<211> LENGTH: 21
<212> TYPE: DNA
<213> ORGANISM: Artificial Sequence
<220> FEATURE:
<223> OTHER INFORMATION: Description of Artificial Sequence: Synthetic
```

```
                      oligonucleotide
<220> FEATURE:
<223> OTHER INFORMATION: Description of Combined DNA/RNA Molecule:
      Synthetic oligonucleotide

<400> SEQUENCE: 396
ucuaauucag guugcaaagt t                                              21

<210> SEQ ID NO 397
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 397
acugaagcau uaaugccagt t                                              21

<210> SEQ ID NO 398
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
auaaaaccua gccaaaugut t                                              21

<210> SEQ ID NO 399
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
ucaaauuugc agcaggauct t                                              21

<210> SEQ ID NO 400
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
ucgucuucau caaauuugct t                                              21

<210> SEQ ID NO 401
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 401
ggaaggaagt tctgttgaa                                                19

<210> SEQ ID NO 402
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 402
ggaaggaagt tctgttgaat taaaa                                         25

<210> SEQ ID NO 403
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 403
gccattagtg caaagaata                                                19

<210> SEQ ID NO 404
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 404
ggccgcaaat tgcacaatt                                                19

<210> SEQ ID NO 405
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 405
ccaccaacag agcctaaaa                                                19

<210> SEQ ID NO 406
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 406
ccaccaacag agcctaaaaa ggaca                                         25

<210> SEQ ID NO 407
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 407

Lys His His His Lys His His His Lys His His His Lys His His His
1               5                   10                  15

Lys

<210> SEQ ID NO 408
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 408
ggaaggaagt tctgttgaat t                                            21

<210> SEQ ID NO 409
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 409
cctttgaaaa aggtgactat t                                            21

<210> SEQ ID NO 410
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 410
cgactactag vgtgccttt t                                             21

<210> SEQ ID NO 411
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 411
cgttcgattg tgtgcgtatt                                              20

<210> SEQ ID NO 412
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 412
ccagaacaaa cccaaggaat t                                            21

<210> SEQ ID NO 413
<211> LENGTH: 21
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 413
cctaatgtgt aaaattaatt t                                              21

<210> SEQ ID NO 414
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 414
ggttcaccat ctggtgttt                                                 19

<210> SEQ ID NO 415
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 415
ggtgacatgg taccacata                                                 19

<210> SEQ ID NO 416
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 416
ggaaggaagt tctgttgaa                                                 19

<210> SEQ ID NO 417
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 417
gccattagtg caaagaata                                                 19

<210> SEQ ID NO 418
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 418
cctttgaaaa aggtgacta                                                 19

<210> SEQ ID NO 419
<211> LENGTH: 19
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 419
cgactactag cgtgccttt                                               19

<210> SEQ ID NO 420
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 420
cgtgcctttg taagcacaa                                               19

<210> SEQ ID NO 421
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 421
ggtacgttaa tagttaata                                               19

<210> SEQ ID NO 422
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 422
cgcttcgatt gtgtgcgta                                               19

<210> SEQ ID NO 423
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 423
gctacatcac gaacgcttt                                               19

<210> SEQ ID NO 424
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 424
cgctttctta ttacaaatt                                               19

<210> SEQ ID NO 425
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 425
cgtgctacaa cttcctcaa                                                19

<210> SEQ ID NO 426
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 426
ccagaacaaa cccaaggaa                                                19

<210> SEQ ID NO 427
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 427
ggccgcaaat tgcacaatt                                                19

<210> SEQ ID NO 428
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 428
gccgcaaatt gcacaattt                                                19

<210> SEQ ID NO 429
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 429
ggcatggaag tcacacctt                                                19

<210> SEQ ID NO 430
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 430 ccccaccaaca gagcctaaa                                               19

<210> SEQ ID NO 431
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 431
ccaccaacag agcctaaaa                                              19

<210> SEQ ID NO 432
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 432
gcagaatgaa ttctcgtaa                                              19

<210> SEQ ID NO 433
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 433
cctatatgga agagccta                                               19

<210> SEQ ID NO 434
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 434
ggaagagccc taatgtgta                                              19

<210> SEQ ID NO 435
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 435
gccctaatgt gtaaaatta                                              19

<210> SEQ ID NO 436
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 436
ccctaatgtg taaaattaa                                              19

<210> SEQ ID NO 437
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 437
cctaatgtgt aaaattaat                                              19

<210> SEQ ID NO 438
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 438
gctatcccca tgtgatttt                                              19

<210> SEQ ID NO 439
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
aagacuacac caugaggugt t                                           21

<210> SEQ ID NO 440
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
accuuguaau gguguugaat t                                           21
```

COMPOSITION AND METHODS OF RNAI PROPHYLACTICS AND THERAPEUTICS FOR TREATMENT OF SEVERE ACUTE RESPIRATORY INFECTION CAUSED BY 2019 NOVEL CORONAVIRUS (2019-NCOV)

This application claims priority to U.S. Provisional application Ser. No. 62/965,063, filed Jan. 23, 2020, the contents of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 10, 2021, is named 4690_0001C_SL.txt and is 121,924 bytes in size.

FIELD OF INVENTION

Novel therapeutic agents for treatment of 2019-nCoV infection are provided. Specifically, siRNA molecules targeting genes or single-stranded viral RNAs of Wuhan seafood market pneumonia virus (2019-nCoV) are provided, together with pharmaceutical formulations comprising chemically modified siRNA oligonucleotides, and optionally containing additional components including: surfactant solution, D5W solution, and other respiratory tract surface-friendly solutions; Histidine-Lysine Co-polymers (HKP), or Spermine-liposome Conjugates (SLiC), or a lung tissue targeted moiety, such as a peptide, a nucleotides, a small molecule and an antibody. Methods of making and using the siRNA molecules and pharmaceutical compositions are provided, including formulations of siRNA/nanoparticle carrier, methods of process development, and specific delivery routes and treatment regimens.

BACKGROUND 2019-nCoV Virus Disease: Biology and Pathology

On Dec. 31, 2019, the World Health Organization (WHO) China Country Office was informed of cases of pneumonia of unknown etiology (unknown cause) detected in Wuhan City, Hubei Province of China. The the WHO reported that a novel coronavirus (2019-nCoV) was identified as the causative virus by Chinese authorities on 7 January (Lu H, Stratton C W, Tang Y W. Outbreak of Pneumonia of Unknown Etiology in Wuhan China: the Mystery and the Miracle. J Med Virol. 2020 Jan. 16.). Wuhan seafood market pneumonia virus (2019-nCoV) is a highly lethal respiratory disease caused by a novel single-stranded, positive-sense RNA betacoronavirus. Symptoms of 2019-nCoV are similar to a range of other illnesses such as influenza and do not necessarily mean that you have 2019-nCoV. Symptoms include fever, coughing and difficulty breathing. Difficulty breathing is a sign of possible pneumonia and requires immediate medical attention. The diagnoses included severe pneumonia, acute respiratory distress syndrome, septic shock and multi-organ failure. The 2019-nCoV infection in Wuhan appears clinically milder than SARS or MERS overall in terms of severity, case fatality rate and transmissibility.

The latest study of the genetic code of 2019-nCoV confirms that the new virus is most closely related to two bat SARS-like coronavirus samples from China, initially suggesting that, like SARS and MERS, the bat might also be the origin of 2019-nCoV (Ji W, Wang W, Zhao X, Zai J, Li X. Homologous recombination within the spike glycoprotein of the newly identified coronavirus 2019-nCoV may boost cross-species transmission from snake to human. J Med Virol. 2020 Jan. 22.). Genomes and subgenomes of CoVs contain at least 6 open reading frames (ORFs). The first ORF (ORF1a/b), about two-third of genome length, encodes 16 non-structural proteins (nsp1-16), except Gammacoronavirus that lacks nsp1. There is a −1 frameshift between ORF1a and ORF1b, leading to production of two polypeptides: pp1a and pp1ab. These polypeptides will be processed by virally encoded chymotrypsin-like protease (3CLpro) or main protease (Mpro) and one or two papain-like protease (PLPs) into 16 nsps (Ziebuhr J, Snijder E J, Gorbalenya A E. Virus-encoded proteinases and proteolytic processing in the Nidovirales. J Gen Virol. 2000; 81(Pt 4): 853-879.). Other ORFs on the one-third of genome near the 3' terminus encode at least four main structural proteins: spike (S), membrane (M), envelope (E), and nucleocapsid (N) proteins.

A 2019-nCoV was isolated from a patient within a short time on 7 Jan. 2020 and subjected to genome sequencing. The 2019-nCoV is a β CoV of group 2B with at least 70% similarity in genetic sequence to SARS-CoV and has been named 2019-nCoV by the WHO (Hui D S, I Azhar E, Madani T A, Ntoumi F, Kock R, Dar O, Ippolito G, Mchugh T D, Memish Z A, Drosten C, Zumla A, Petersen E., "The continuing 2019-nCoV epidemic threat of novel coronaviruses to global health—The latest 2019 novel coronavirus outbreak in Wuhan, China" Int J Infect Dis. 2020 Jan. 14; 91:264-266.). Sequence analysis showed that the 2019-nCoV possesses a typical genome structure of a coronavirus and belongs to the cluster of betacoronaviruses that includes Bat-SARS-like (SL)-ZC45, Bat-S L ZXC21, SARS-CoV and 2019-nCoV. Based on the phylogenetic tree of CoVs, 2019-nCov is more closely related to bat-SL-CoV ZC45 and bat-SL-CoV ZXC21 and more distantly related to SARS-CoV (Chen Y, Liu Q, Guo D. "Coronaviruses: genome structure, replication, and pathogenesis," J Med Virol. 2020 Jan. 22.).

Current Prophylaxis and Therapeutics

At present, there are no specific antiviral therapies for coronavirus and the main treatments are palliative. Recombinant interferons (IFN) with ribavirin have only limited effects on coronavirus infections (Cinatl J, Morgenstern B, Bauer G, Chandra P, Rabenau H, Doerr H W., "Treatment of SARS with human interferons," Lancet. 2003; 362(9380): 293-294.). After the SARS and MERS epidemic, a number of anti-CoV agents were developed against CoVs proteases, polymerases, MTases, and entry proteins, but none of these have yet been proved effective in clinical trials (Dyall J, Gross R, Kindrachuk J, Johnson R F, Olinger G G Jr, Hensley L E, Frieman M B, Jahrling P B., "Middle East Respiratory Syndrome and Severe Acute Respiratory Syndrome: Current Therapeutic Options and Potential Targets for Novel Therapies," Drugs. 2017 December; 77(18):1935-1966; Chan J F, Chan K H, Kao R Y, To K K, Zheng B J, Li C P, Li P T, Dai J, Mok F K, Chen H, Hayden F G, Yuen K Y., "Broad-spectrum antivirals for the emerging Middle East respiratory syndrome coronavirus," J Infect. 2013; 67(6): 606-616; Liu Q, Zhou Y H, Ye F, Yang Z Q., "Antivirals for Respiratory Viral Infections: Problems and Prospects," Semin Respir Crit Care Med. 2016; 37(4): 640-646).

So far, therapies with plasma and antibody obtained from convalescent patients have been proposed as principal treatment (Mair-Jenkins J, Saavedra-Campos M, Baillie J K, Cleary P, Khaw F M, Lim W S, Makki S, Rooney K D, Nguyen-Van-Tam J S, Beck C R; "Convalescent Plasma Study Group. The effectiveness of convalescent plasma and hyperimmune immunoglobulin for the treatment of severe acute respiratory infections of viral etiology: a systematic review and exploratory meta-analysis," J Infect Dis. 2015; 211(1): 80-90). At present however, there is very limited clinical information available regarding the 2019-nCoV infection, and data are missing regarding the age range, animal source of the virus, incubation period, epidemic curve, viral kinetics, transmission route, pathogenesis, autopsy findings and any treatment response to antivirals among the severe cases. The Wuhan outbreak is a stark reminder of the continuing threat of zoonotic diseases to global health security. More significant and better targeted investments are required for a more concerted and collaborative global effort, learning from experiences from all geographical regions (Zumla A, Dar O, Kock R, Muturi M, Ntoumi F, Kaleebu P, et al., "Taking forward a'One Health' approach for turning the tide against the Middle East respiratory syndrome coronavirus and other zoonotic pathogens with epidemic potential," Int J Infect Dis. 2016; 47: 5-9).

Unfortunately, there is no approved vaccine or antiviral treatment available for coronavirus infection. A better understanding of the life cycle of 2019-nCoV, including the source of the virus, how it is transmitted and how it replicates are needed to both prevent and treat the disease. As there are no effective therapeutics or vaccines, the best way to deal with severe infections of CoVs is to control the source of infection, early diagnosis, reporting, isolation, supportive treatments, and timely publishing of epidemic information to avoid unnecessary panic. At the same time, it is extremely important to quickly promote the development of innovative drugs.

SUMMARY OF THE INVENTION

What is provided is a pharmaceutical composition containing at least two siRNA molecules that target the conserved regions of the Wuhan seafood market novel pneumonia 2019 Novel Coronavirus (2019-nCoV), where the composition contains a pharmaceutically acceptable carrier, and where the carrier contains a polymeric nanoparticle and/or a liposomal nanoparticle carrier. The siRNA molecules contain oligonucleotides having a length of 19-25 base pairs. The composition may contain siRNA molecules that inhibit non-structural (NS) RdRp, replicase or helicase virus gene expression, or Spike viral gene expression, 2019-nCoV genes other than Spike. The siRNAs may be designed against the sense strand sequences of NS genes and/or at least one sense strand sequence of the 2019-nCoV Spike gene. The siRNAs may be designed against the sense strand sequences of 2019-nCoV genes other than the Spike gene.

In one embodiment, the sense strand of each siRNA is selected from the siRNAs having the sequences of SEQ ID NO:1-101. In a further embodiment the sense strand of each siRNA is selected from the siRNAs having the sequences of Table E. In a particular set of embodiments, the two siRNA molecules are selected from the group consisting of:

CoV3 and Cov18;
CoV3 and CoV14;
CoV4 and CoV14; and
AoV4 and CoV18,
where CoV3 has the sequence GGAAGGAAGTTCTGTTGAA (SEQ ID NO: 401) or GGAAGGAAGTTCTGTTGAATTAAAA (SEQ ID NO: 402), CoV4 contains the sequence GCCATT-AGTGCAAAGAATA (SEQ ID NO: 403), CoV14 contains the sequence GGCCGCAAATTGCACAATT (SEQ ID NO: 404), and CoV18 has the sequence CCAC-CAACAGAGCCTAAAA (SEQ ID NO: 405) or CCAC-CAACAGAGCCTAAAAAGGACA (SEQ ID NO: 406).

The composition may contain a polymeric nanoparticle carrier, such as Histidine-Lysine co-polymer (HKP) and/or it may contain a liposomal nanoparticle carrier, such as a Spermine-Lipid Conjugate (SLiC) in formulation with cholesterol. In these compositions, the HKP and the siRNA molecules self-assemble into nanoparticles and/or the SLiC and the siRNA self-assemble into nanoparticles in a formulation containing cholesterol.

Also provided are methods of treating a subject, such as a human subject, infected with a 2019 Novel Coronavirus infection by administering to the subject a pharmaceutically effective amount of the composition as described above. The composition may be administered through airway instillation; intraperitoneal administration; and/or through an airway nebulizer.

The subject may alternatively be a mouse, ferret, or monkey.

BRIEF DESCRIPTION OF THE DRAWINGS

FIG. 7A shows a standard curve used to measure IFN-α concentration (Lowry Method) and FIG. 7B shows how IFN-α concentration in each sample was determined and normalized to total protein.

FIG. 14 shows the inhibiting effects and $EC_{50}$s of some siRNAs for the expression of target genes in 293T and A549 cells. The $EC_{50}$s of these siRNAs were generally less than 10 pg/μL.

FIG. 19 (Table 1) shows siRNA sequences, 25-mer blunt-end oligos and 21-mer sticky-end oligos, targeting various viral RNA (non-structure proteins).

FIG. 20 (Table 2) shows siRNA sequences, 25-mer blunt-end oligos and 21-mer sticky-end oligos, targeting various viral RNAs (spike protein), FIG. 21 (Table 3) shows the most potent siRNA oligos, 25-mer blunt-end oligos and 21-mer sticky-end oligos, targeting various viral proteins and genes.

DETAILED DESCRIPTION

Figure 1:
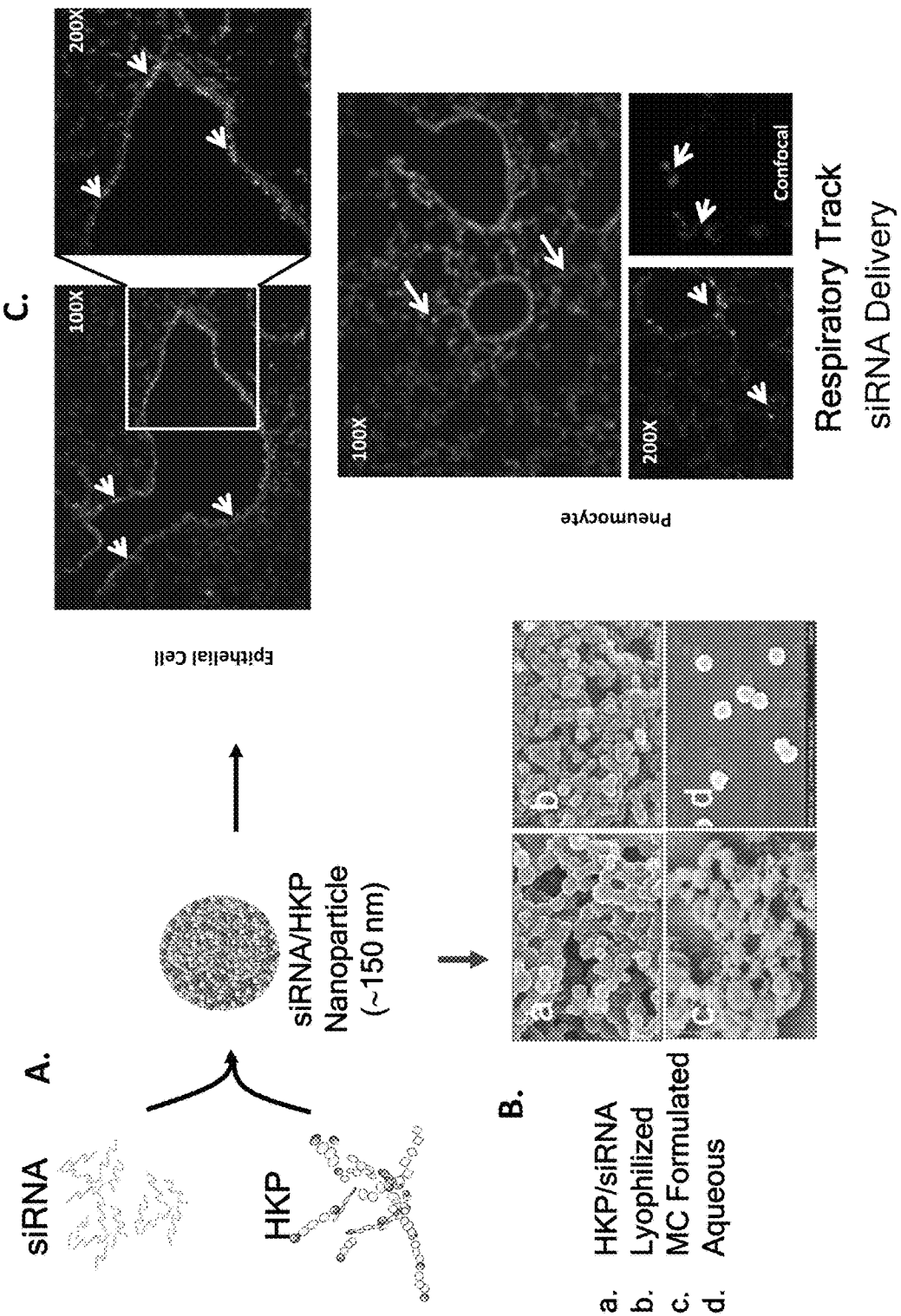
FIG. 1 shows Histidine-Lysine co-polymer enhances topical and subcutaneous siRNA deliveries in vivo. (a) The self-assembled HKP/siRNA nanoparticles (average 150 nm in diameter) can be dissolved in aqueous solution, can be lyophilized into dry powder, and can be redissolved and mixed with methylcellulose, or with RNAse free water. HKP/siRNA nanoparticle delivery to mouse respiratory tract: upper airway, bronchi, alveoli.

Small interfering RNA (siRNA) molecular compositions are provided that inhibit the infection and/or replication of the severe acute respiratory syndrome coronavirus 2 (SARS-CoV-2). The siRNAs target the conserved gene sequences of the SARS-CoV-2 viruses, and the sense strand of the siRNAs are exactly the same as the gene sequences of the SARS-CoV-2 viruses. These conserved gene sequences include the genes that involve multiple proteins and/or enzymes that closely related to the invasion, replication, assembly, release of the SARS-CoV-2. When the SARS-Cov-2 viruses lack these proteins and/or enzymes, they cannot complete their entire life cycle. Preferably, the siRNAs can simultaneously inhibit the sequences of SARS-CoV and SARS-CoV-2, or simultaneously inhibit the sequences of MERS-CoV and SARS-CoV-2. Compositions also are provided that contain pharmaceutical material as a delivery carrier, for example a polypeptide polymer carrier. Advantageously this carrier is a polypeptide polymer composed of histidine and lysine. Combining siRNAs with the delivery carrier to form nano-particles provides compositions that effectively inhibit the SARS-CoV-2 virus from infecting host cells in vivo and in vitro, and inhibit the replication and assembly, and release from the cells.

RNA interference (RNAi) is a naturally occurring, highly specific mode of gene regulation. The mechanics of RNAi are both exquisite and highly discriminating. At the onset, short (19-25 bp) double stranded RNA sequences (referred to as short interfering RNAs, siRNAs) associate with the cytoplasmically localized RNA Interference Silencing Complex (RISC) (Jinek M, Doudna J A., "A three-dimensional view of the molecular machinery of RNA interference," Nature. 2009; 457(7228): 405-412.). The resultant complex then searches messenger RNAs (mRNAs) for complementary sequences, eventually degrading (and/or attenuating translation of) these transcripts. Scientists have co-opted the endogenous RNAi machinery to advance a wide range of uses for siRNAs, including as therapeutics.

There are many biological barriers and factors that protect the lungs from foreign particles, such as a thick and elastic mucus layer that may bind inhaled drugs and remove them via mucus clearance mechanism, low basal and stimulated rates of endocytosis on the apical surfaces of well-differentiated airway epithelial cells, the presence of RNase extra- and intra-cellularly, and the presence of endosomal degradation systems in the target cells, among others. Overcoming the difficulties concerning respiratory tract delivery and effective cellular entry and function will pave the way for siRNA as a systemic anti-2019-nCoV therapeutic.

In addition, the delivery vehicle and mode of administration must be chosen to be appropriate to the stage of the infection and provide the fastest onset of silencing at the required site of action, e.g. early stage infection/prophylaxis at the epithelial/endothelial cells, and in later stage disease through systemic administration. Among them, topical/systemic delivery through inhalation has been shown to be the most effective way to treat the respiratory system diseases. In a pandemic setting, this delivery approach will allow ease of administration directly to patients.

Antiviral Strategies

Coronaviruses are enveloped viruses and their positive strand RNA genome, the largest of all RNA viruses, encodes for as many as 16 non-structural proteins (nsps), 4 major structural proteins, and up to 8 accessory proteins. Many of these proteins provide essential, frequently enzymatic, functions during the viral life cycle and are therefore attractive targets for antiviral intervention. Antiviral strategies are mainly proposed for targeting coronavirus entry and essential enzymatic functions, such as coronavirus protease or RNA-dependent RNA polymerase (RdRp) activities. For example, the spike (S) protein mediates binding of different CoVs to their specific cellular receptors, an event associated with preferential virus tropism for either ciliated or non-ciliated cells of the airway epithelium. The S protein also mediates fusion between lipids of the viral envelope and the host cell plasma membrane or membranes of endocytic vesicles to promote delivery of viral genomic RNA into the cytoplasm.

Virus binding and cell entry events can be inhibited by antibodies directed against the S protein, antibodies or small molecules interfering with the virus receptors, or synthetic peptides derived from the fusion-triggering heptad repeat regions of the S protein. Following virus entry, the coronavirus genome, a positive sense, capped and polyadenylated RNA strand, is directly translated, resulting in the synthesis of coronavirus replicase gene-encoded nsps. Coronavirus nsps are translated as two large polyproteins harboring proteolytic enzymes, namely papain-like and chymotrypsin-like proteinases that extensively process coronavirus polyproteins to liberate up to 16 nsps (nsp 1-16). These proteolytic functions are considered essential for coronavirus replication and, consequently, a number of candidate drugs were reported to inhibit coronavirus polyprotein processing. Likewise, the coronavirus RdRp activities, which reside in nsp8 and nsp12, are considered essential for coronavirus replication and attractive targets for antiviral intervention. In addition to these classical drug targets, coronaviruses encode an array of RNA-processing enzymes representing additional candidate targets. These include a helicase activity linked to an NTPase activity in nsp13, a 3'-5'-exonuclease activity linked to a N7-methyltransferase activity in nsp14, an endonuclease activity in nsp15, and a 2'-O-methyltransferase activity in nsp16.

Like all positive strand RNA viruses, coronaviruses synthesize viral RNA in organelle-like structures in order to compartmentalize this critical step of the viral life cycle to a specialized environment that is enriched in replicative viral and host-cell factors, and at the same time protected from antiviral host defense mechanisms. There is now a growing body of knowledge concerning the involvement, rearrangement and requirement of cellular membranes for RNA synthesis of a number of positive-strand RNA viruses, including coronaviruses. Three coronaviral nsps, i.e., nsp3, nsp4, and nsp6 are thought to participate in formation of these sites for viral RNA synthesis. In particular, these proteins contain multiple transmembrane domains that are thought to anchor the coronavirus replication complex through recruitment of intracellular membranes to form a reticulovesicular network (RVN) of modified, frequently paired, membranes that includes convoluted membranes and double membrane vesicles (DVM) interconnected via the outer membrane with the rough ER.

Viruses can use different strategies to escape the RNAi mechanism. In the process of virus evolution, mutations occur from time to time. When siRNA initiates the RNAi mechanism, viruses may make siRNA ineffective through mutation of the target sequence. Therefore, how to resolve the contradiction between frequent virus mutations and the high specificity of RNAi is the key issue to siRNA molecular design. The SARS-CoV virus frequently mutates and, recently, researchers discovered that a mutation in the SARS-CoV-2 genome increased its ability to infect human cells. The mutation was named "D614G". This mutation causes a small but effective change in the S protein protruding on the surface of the virus, increasing the ability to infect human cells, thus helping it become the dominant strain spreading in the world today. To address this problem of evasion of the RNAi mechanism that may be caused by virus mutations, the compositions and methods presented herein adopt two strategies: (1) siRNA molecules are designed against the conserved gene sequence of the virus that are the most critical for virus replication and assembly, so they are highly conserved sequences after actual verification, and; (2) two or more siRNAs are used to simultaneously inhibit the expression of two or more key genes of the virus.

Target Selection 2019-nCoV is an enveloped single-stranded positive-sense RNA virus belonging to the genus Betacoronavirus. The length of the genome is around 30k nt. The genome contains 14 predicted open reading frames (ORFs): ORF1a, ORF1b, Spike (S) Protein, 3, 4a, 4b, 5, Envelope (E) Protein, Membrane (M) Protein and Nucleocapsid (N) Protein, with 5' two third of the genome (ORF1a, ORF1b) encoding 16 non-structure proteins (nsp1-16), and rest 3' third of the genome encoding 4 structure proteins (S, E, M and N proteins).

The spike (S)protein of 2019-nCoV is a glycoprotein with 1282 amino acids, having a molecular weight of over 150 kDa, which is an important determinant of virus virulence and host range. Trimers of S protein form the spikes on the 2019-nCoV envelope, which are responsible for the receptor binding and membrane fusion. Similar to the HIV envelope (env) and influenza hemagglutinin (HA), S protein of 2019-nCoV are Class I viral fusion proteins, which require protease cleavage between the S1 and S2 domains to allow the conformational changes in S2, and initiate the virus entry and syncytia formation. The importance of S protein on virus entry and virus-host membrane fusion makes it an excellent target for anti-2019-nCoV siRNA development.

After entry into the cell, two polyproteins, pp1a and pp1ab of 2019-nCoV express and undergo co-translational proteolytic processing into the proteins that form the viral replication complex. During this processing, the activity of nsp-3, papain-like protease (PL$^{pro}$) and nsp-5, 3C-like proteinase (3CL$^{pro}$) are critical for the generation of 16 non-structural proteins from the polyprotein.

2019-nCoV RNA-dependent RNA polymerase (RdRP), encoded by nsp-12, is the most important component of viral replication complex. This complex is responsible for both the transcription of the nested sub-genomic mRNAs and the replication of the genomic positive-strand RNA. Both processes take place in the cytoplasm. In the viral mRNA transcription, the negative-strand RNAs are generated from genomic RNA at first, and then transcribe a set of 3'-co-terminal nested sub-genomic mRNAs by the replication complex, with a common 5' "leader" sequence (67 nt) derived from the 5' end of the genome. The newly synthetic genomic RNAs are produced by the taking the negative-strand RNAs as the template. The key role of nsp-12 on viral mRNA transcription and genome replication means this this gene is a target for design of anti-2019-nCoV siRNA.

Based upon the above information, we selected RNA-dependent RNA polymerase (RdRp), replicase, helicase, spike (S) protein and some other structure genes (such as M and N protein) and non-structural genes (such as nsp-2, nsp-10 and nsp-15) of 2019-nCoV as the targets for siRNA cocktail-mediated therapeutic approach. The present disclosure provides siRNA molecules comprising a double-stranded sequence of 21 or 25 nucleotides in length, where the siRNA molecule inhibits expression of the target genes of 2019-nCoV. The siRNA molecule has blunt ends, or has 3' overhangs of one or more nucleotides on both sides of the double-stranded region. The siRNA cocktail of the invention contains two, three, four or more sequences targeting those genes of 2019-nCoV. Preferably the cocktail of siRNAs are against different segments of the virus—which ensures that the virus will be inhibited by at least one of the siRNAs unless both segments undergo mutations at the siRNA targeting site at the same time—a very unlikely prospect.

A series of 25 base pair blunt-end siRNAs and 19 base pair sticky-end siRNAs was designed to interfere with key genes or partial gene sequences that are critical to the SARS-CoV-2 replication cycle. These key genes include, but are not limited to, the S gene, E gene, M gene, N gene, and RdRP gene, etc. Each gene of the SARS-CoV-2 strain can be included in this list.

In particular, the siRNA compositions described herein include siRNAs that inhibit spike glycoprotein gene (S), which can effectively inhibit the expression of S protein. The S protein infects the host cells by interacting with the host receptor (ACE2), which determines the virus's infection target and infection ability.

The siRNA molecular compositions also include siRNAs that inhibit the ORF1AB gene of SARS-CoV-2, which can effectively inhibit the expression of Mpro (nsp5), PLpro, 3CLPro (3CL hydrolase), RdRp (nsp12), Helicase (nsp13) and other protein/enzymes. The ORF1AB gene is located at the 5' end of the viral genome and encodes multifunctional proteins that involved in viral RNA transcription and replication, which contains a protease responsible for cleaving the polyprotein.

The siRNA molecular compositions also include siRNAs that effectively inhibit the expression of ORF3A protein. The protein encoded by ORF3a is an accessory protein that has the function of inducing cell apoptosis and helps change the environment inside the infected cell, making it easier for the virus to replicate. The ORF3a protein makes holes in the membrane of infected cells, making it easier for the virus to escape.

The siRNA molecular compositions also include siRNAs that inhibit the envelope protein gene (E), which can effectively inhibit the expression of E protein. The E protein plays a key role in virus morphogenesis and assembly, and through self-assembly in the host cell membrane to form pentameric protein-lipid pores that allow ion transport, and also plays a role in the induction of apoptosis.

The siRNA molecular compositions also include siRNAs that inhibit the membrane protein gene (M), which can effectively inhibit the expression of M protein. The M protein is an important component of the viral envelope and plays a central role in the morphogenesis and assembly of the virus through interaction with other viral proteins.

The siRNA molecular compositions also include siRNAs that inhibit the nucleocapsid protein gene (N), which can effectively inhibit the expression of N protein. The N protein functions through the interaction with the viral genome and the M protein during the virus assembly process and plays an important role in improving the transcription efficiency of the viral genome and virus replication.

The siRNA compositions as described herein include an siRNA that inhibits the ORF10 gene, which can effectively inhibit the expression of ORF10 protein. The ORF10 protein is a small accessory protein unique to SARS-CoV-2, and its function is not yet fully defined.

The siRNA molecular compositions also include siRNAs that inhibit the 3'-end untranslated region sequence (3'-UTR). The molecules can bind to the 3'-UTR of the viral mRNA, degrading the viral mRNA.

The siRNAs described herein typically have a short double-stranded RNA structure with a length of 19 base pairs or 25 base pairs. The 19-base pair siRNA is a double-stranded RNA with a sticky end of two deoxythymidine (dTdT) protrusions at the 3' end of each RNA strand. The 25-base pair siRNA is a double-stranded RNA with blunt ends.

Two methods may be used to predict siRNAs targeting conserved regions of viral genes. One method is to arrange all the genes of multiple strains and determine the overlapping regions of these genes, and then decide whether it is possible to design siRNA with relevant pharmacological activities to target and inhibit these specific gene domains. This method can usually achieve good results, however, when some virus strains have large variations, it will severely limit the number of predictable siRNAs, and the siRNA designed by this method may show lower effectiveness in gene silencing.

Advantageously, siRNA design takes into account the consistency of the siRNA sequence and the target gene sequence in the viral gene. The 19-base pair siRNA has been proven to effectively silence related genes both in vivo and in vitro. Because the siRNAs also include 25-base pair siRNAs, these siRNAs may have some sequence redundancy. After removing these redundant sequences, the target gene can still be completely silenced. Methods have been established to detect gene domains that may not be 100% identical to all bases in the siRNA sequence, but the gene domain should have, at least, 19 consecutive bases that are consistent with siRNA. The ability to identify genes that are not identical to all 25-base pairs siRNA may increase the number of virus strains that can be targeted by siRNA.

Synergistic Effects of Combining Multiple siRNAs

By expanding the search of siRNAs for all coronavirus genes and the sequences of all the pathogenic coronaviruses such as SARS-CoV, MERS-CoV, and SARS-CoV-2, we can determine the following two types of siRNAs: a) siRNAs that show significant strain specificity; b) siRNAs that target specific genes in specific virus strains. By combining the siRNAs in the list that can inhibit a broad range of virus strains (such as anti-S protein), the specific siRNAs against another gene in SARS-CoV-2 (such as RdRP or helicase), and a third siRNA that can target another specific gene of SARS-CoV-2, we can produce a broad and effective siRNAs composition that can inhibit multiple virus strains. This composition can inhibit virus mutation by inhibiting multiple targets of the virus, therefore, preventing the virus from escaping the treatment.

The siRNA compositions as described herein include one, two, or more siRNAs. The siRNAs can match the gene sequence of SARS-CoV-2. When the siRNA enters the host cell, it binds to the RNA-induced silencing complex (RISC), thereafter, the guide strand of the RNA will bind to the viral mRNA. After the guide strand carries the RISC approaches the viral mRNA, the protease in RISC will degrade viral mRNA, thereby inhibiting viral gene expression. The viral mRNA may be the positive-strand genomic RNA of the virus or it may also be replicated based on the viral genomic RNA which acts as the positive-strand RNA of the next-generation of the viral genome.

When the composition contains two or more siRNAs, these siRNAs advantageously target different genes of SARS-CoV-2, that is, they simultaneously inhibit the expression of two or more genes of SARS-CoV-2. More advantageously, in these two or more siRNAs, one siRNA targets at least one structural protein gene and at least one targets non-structural protein genes. In this fashion the composition can simultaneously inhibit the expression of at least one structural protein gene and one non-structural protein gene.

A combination of siRNAs is provided that can inhibit the expression of both the S protein gene and the RdRp gene located in ORF1AB. After transferring these two siRNAs into host cells, the expression of the RdRp enzyme can be inhibited, therefore, preventing the virus from replicating its RNA; At the same time, they can also inhibit the expression of S protein, so that the virus cannot be packaged into complete virus particles, thus lacking the ability to infect new host cells.

A combination of 2 siRNAs is provided that can inhibit the ORF1ab and N-protein within the virus. It was demonstrated that silencing both these targets at the same time inhibited the replication of the virus. More than 80% inhibition of the virus occurred with a combination of each siRNA at 41 pM of each.

A combination of siRNAs is provided that can inhibit the expression of both the E protein gene and the RdRp gene located in ORF1AB. After transferring these two siRNAs into host cells, the expression of the RdRp enzyme can be inhibited, therefore, preventing the virus from replicating its RNA; At the same time, they can also inhibit the expression of E protein, so that the virus cannot be packaged into complete virus particles, and the morphogenesis and assembly of the virus cannot be completed, thus lacking the ability to release from the cells.

A combination of siRNAs is provided that can inhibit the expression of both the S protein gene and the helicase gene located in ORF1AB. After transferring these two siRNAs into host cells, they can inhibit the expression of helicase, and inhibit the melting of nucleic acid double strands necessary for virus replication, and restrain the formation of viral replication/transcription complexes; At the same time, they can also inhibit the expression of S protein, so that the virus cannot be packaged into complete virus particles, thus lacking the ability to infect new host cells.

A combination of siRNAs is provided that can inhibit the expression of both the E protein gene and the RdRp gene located in ORF1AB. After transferring these two siRNAs into host cells, the expression of the RdRp enzyme can be inhibited, therefore, preventing the virus from replicating its RNA; At the same time, they can also inhibit the expression of E protein, so that the virus cannot be packaged into complete virus particles, thus lacking the ability to release from the cells.

A combination of siRNAs is provided that can inhibit the expression of the S protein gene, the E protein gene, and the RdRp gene located in ORF1AB. After transferring these three siRNAs into host cells, the expression of the RdRp enzyme can be inhibited, therefore, preventing the virus from replicating its RNA; At the same time, they can also inhibit the expression of S protein and E protein, so that the virus cannot be packaged into complete virus particles and released from cells, thus lacking the ability to infect new host cells.

A combination of 2 siRNAs is provided that can inhibit the ORF1ab and N-protein within the virus. It was demonstrated that silencing both these targets at the same time inhibited the replication of the virus. More than 80% inhibition of the virus occurred with a combination of each siRNA at 41 pM of each.

The composition containing two or more siRNAs can be packaged individually or mixed into a package. That is, the two or more siRNAs may be provided already admixed, may be mixed prior to administration, or may be administered separately.

HKP-Based Polymeric Nanoparticle siRNA Delivery System

The pharmaceutical preparations containing the siRNAs advantageously contain a specific sized nanoparticle preparation, mainly spherical or ellipsoidal. In this preparation, the polypeptide/lipid cationic polymeric carriers and the siRNAs interact through electrostatic force. In the case of excess polymer carrier molecules, most of the siRNAs are placed inside the nanoparticles, making the entire nanoparticle particle carry a positive charge. The diameter of the nanoparticles is 50-300 nm, preferably, the diameter is 100-200 nm. The electric potential (zeta potential) of the nanoparticle preparation particles is 5-50 mV, preferably, the electric potential is 10-40 mV, and more preferably, the electric potential is 30-45 mV.

The present disclosure also provides a therapeutic agent, a HKP-siRNA Nanoparticle, which includes the siRNA molecules and a pharmaceutically acceptable carrier. Histidine-lysine polymers (HKP) have been applied for siRNA deliveries in vitro and in vivo. A pair of the HK polymer species, H3K4b and H3K(+H)4b, have a lysine backbone with four branches containing multiple repeats of Histidine, Lysine or Asparagine. When this HKP aqueous solution was mixed with siRNA at a N/P ratio of 4:1, or 3:1, or 5:1 by mass, the nanoparticles (average size of 100-200 nm in diameter) self-assembled (FIG. 1). Optimal branched histidine-lysine polymer, HKP, was synthesized on a Rainin Voyager synthesizer (PTI, Tucson, AZ). The two species of the HKP used in the study were H3K4b with a structure of (R)K(R)-K(R)-(R)K(X), for H3K4b where R=KHHHKHHHKHHHKHHHK (SEQ ID NO: 407); K=lysine and H=histidine. The particle size and zeta-potential were measured with a Brookhaven Particle Sizer 90 Plus. The HKP-siRNA aqueous solution was semi-transparent without noticeable aggregation or precipitate, and could be stored at 4° C. for at least three months. We have also developed a process for lyophilizing this HKP-siRNA solution into dry powder. After dissolving this dry powder with PBS or D5W, the therapeutic agent can be administrated into the blood stream through IV infusion or it can be used for topical administration to the epidermis. The drugs can be also delivered into specific lesions of the respiratory system through inhalation administration.

SLiC-Based Lipid Nanoparticle siRNA Delivery System

Figure 2:
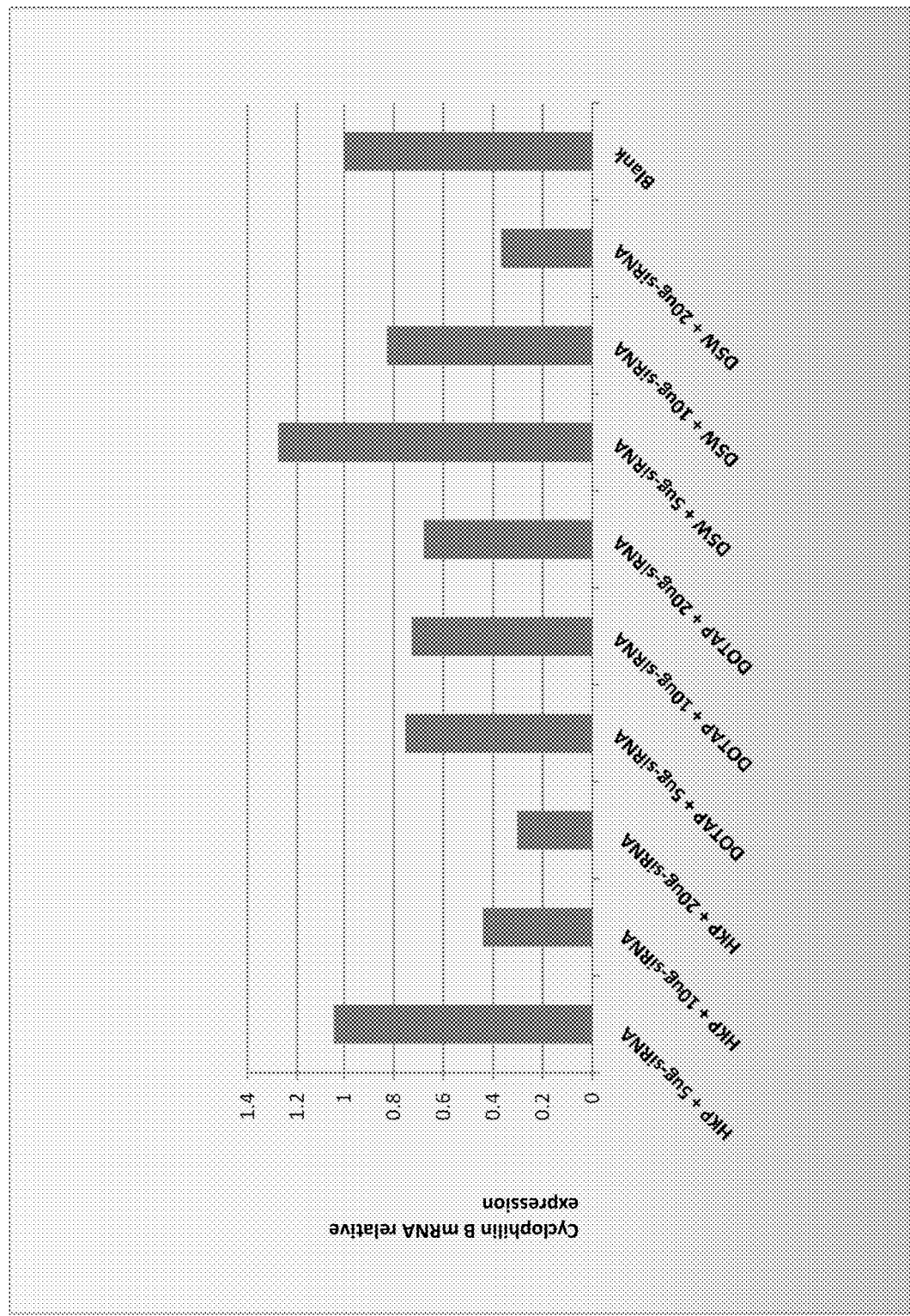
FIG. 2 a comparison of target knockdown of lung endogenous gene among HKP, DOTAP and D5W after oral tracheal deliveries of siRNA with three different dosing regimens. HKP demonstrated efficient siRNA-mediated knockdown of the target gene at the 20 μg dose.
Figure 5:
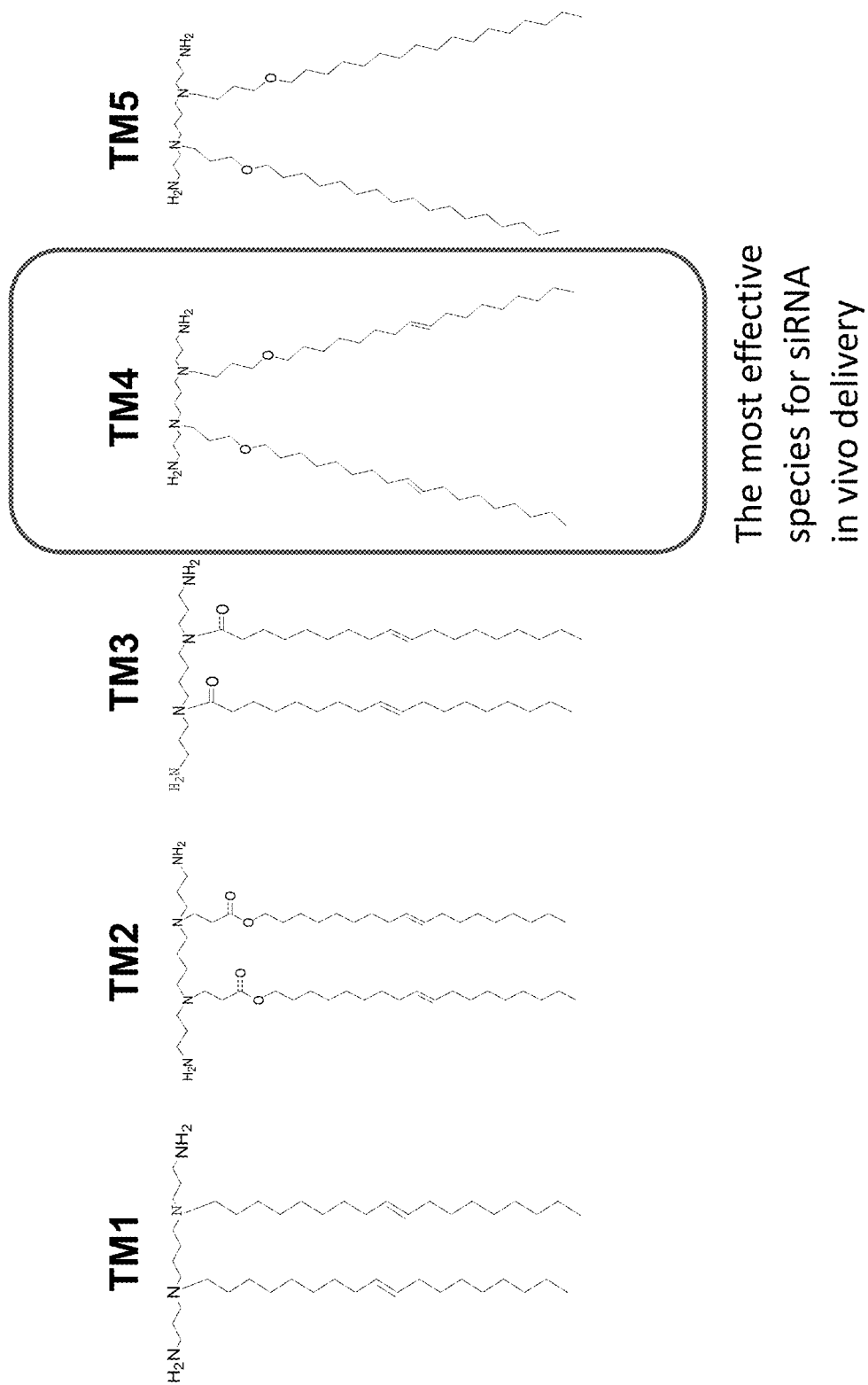
FIG. 5 shows structures of Spermine-Lipid Conjugates (SLiC).
Figure 6:
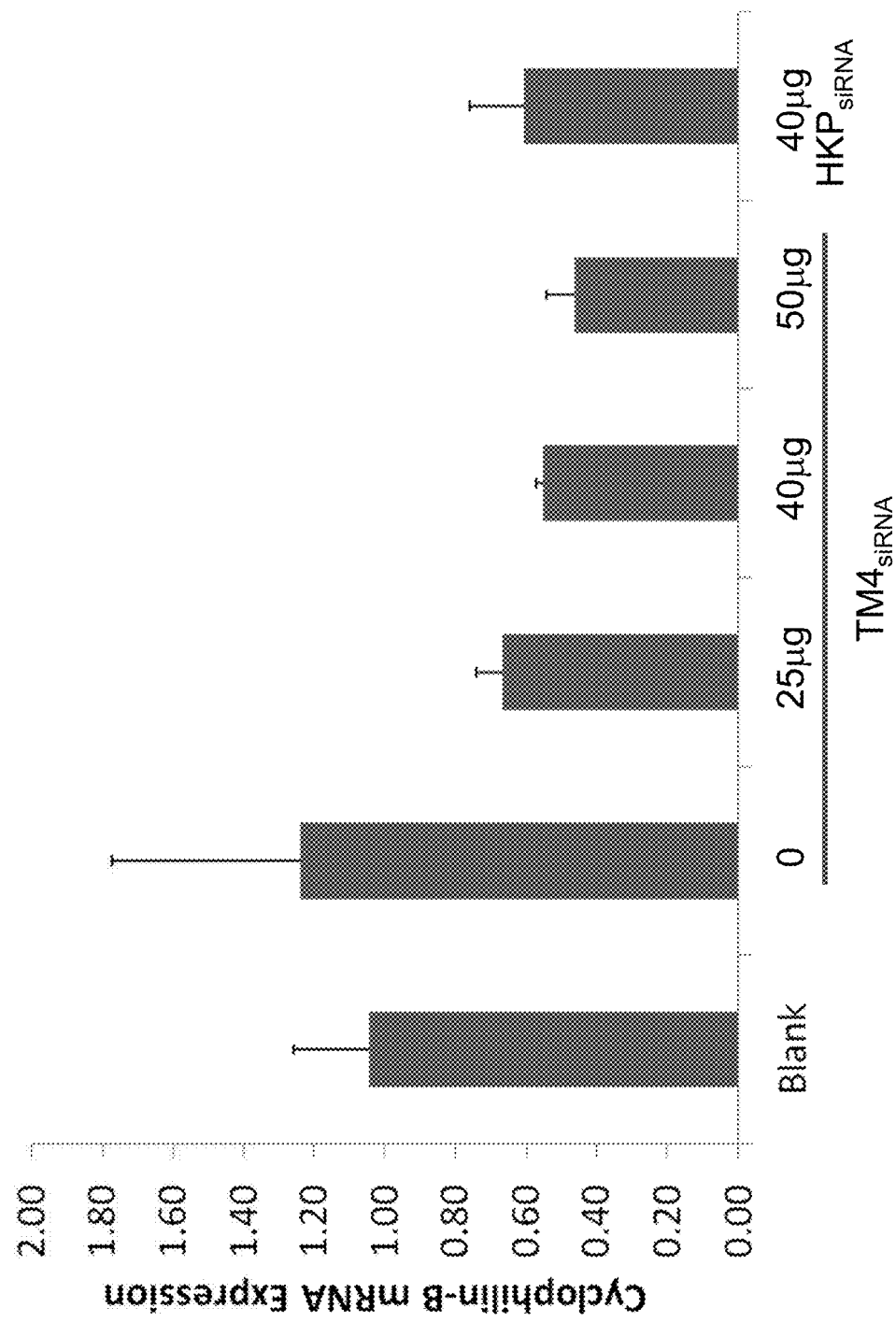
FIG. 6 shows an example of target gene expression after SLiC-mediated siRNA delivery.
Figure 7:
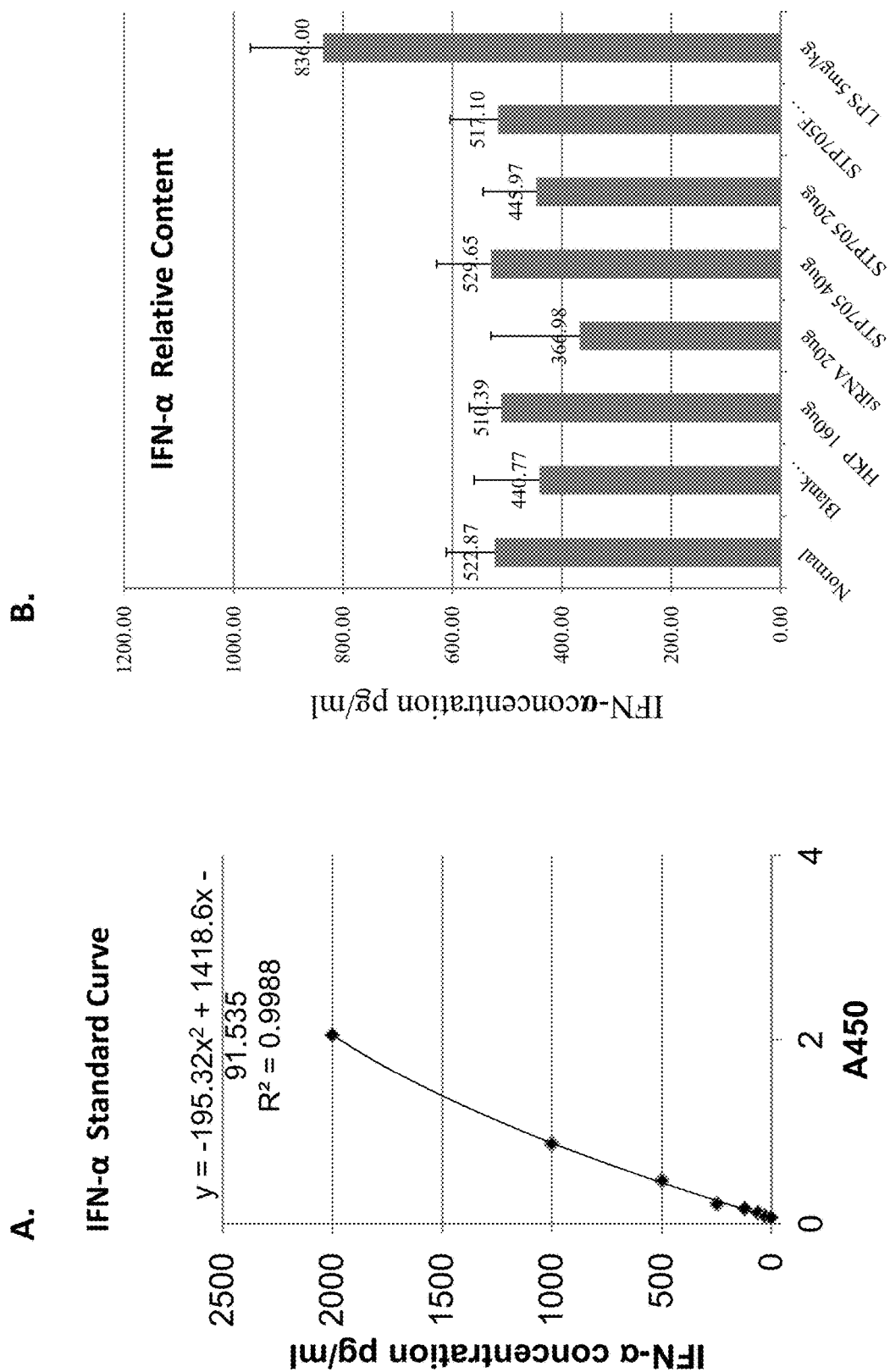
FIG. 7 shows IFN-α Expression after Histidine-Lysine Polymer mediate siRNA delivery in the Lung.

We also developed a novel drug delivery carrier containing a new cationic lipid and cholesterol (FIG. 2). The cationic lipid is made of a spermine head and an oleyl alcohol tail which is conjugated with the cholesterol as a novel and unique siRNA delivery system (Spermine-Lipid Cholesterol, SLiC). The CAS Registry Number of spermine is 71-44-3. When SLiC is mixed with siRNA duplexes in aqueous solution, siRNA/SLiC nanoparticles are formulated through a self-assembling process. This new form of lipid nanoparticle is readily biodegradable. FIG. 5 shows several species of this novel lipid structure with spermine as cationic head and oleyl alcohol tails conjugated through various bonds at two tertiary amine groups in the middle. We have applied this carrier for siRNA transfection in Hela cells and 293 cells for target gene knockdown in vitro, and we also tested it with mouse model for in vivo delivery of siRNA.

Silencing Effect of Drugs on Virus Target Genes and its Inhibitory Effect on Viruses To identify siRNAs that have a significant inhibitory effect on the target gene and that effectively block the infection and replication of the virus(es) a dual-luciferase pseudotyped virus-based reporting system or the real SARS-CoV-2 virus can achieve these two goals. A suitable reporting system is the psiCHECK system (Promega, Inc. Madison WI)

Inhalation Administration of Drugs with Nebulizer

COVID-19 is an infectious disease of the respiratory system. It enters the cells through the ACE2 receptors or Neuropilin 1 receptors on the epidermal cells of the respiratory tract and lungs to start the replication life cycle. Therefore, administration through the respiratory tract is an effective way of administration. The drug is delivered to the respiratory system, especially the lower respiratory tract and lungs through a specific inhalation device, which can effectively reach the focus of virus infection and replication to achieve high-efficiency of the inhibition of virus. One administration mode for the prevention and treatment of novel coronavirus infection is atomized inhalation administration. Specifically, a hand-held atomization device is used to atomize the nanoparticles preparation. The inhaled droplets of the drug preparation are atomized through the respiratory tract to deliver the drugs to the lower respiratory tract and lungs. The device preferably uses an ultrasonic atomization device, and more preferably, using a micro-net ultrasonic atomization inhalation device.

The present invention will be further described in detail below in conjunction with specific embodiments, but the scope of the present invention is not limited to the following embodiments. Its purpose is to enable those who skilled in the art to understand the content of the present invention and implement it, and this does not limit the protection scope of the present invention. All equivalent changes or modifications made according to the idea of the present invention should be covered by the protection scope of the present invention.

EXAMPLES

Example 1. 2019-nCoV Viral Structure and Protein Function 2019-nCoV is AN enveloped single-stranded positive sense RNA viruses with a genome of of 29,903 nt. The genome structure of 2019-nCoV is similar to other coronaviruses such as 2019-nCoV, with the 5' two-thirds of the genome encoding the non-structural proteins (NSPs) required for viral genome replication, the remaining 3' third of the genome encoding the structural genes that make up the virion (spike, envelope, membrane, and nucleocapsid proteins), and four accessory genes interspersed within the structural gene region. At the 5' end of the genome there is a leader sequence (67 nt), which is followed by an untranslated region (UTR). At the 3' end of the RNA genome there is another UTR, followed by a poly(A) sequence of variable length. Transcription-regulatory sequences (TRS 5' AACGAA 3') are found at the 3' end of the leader sequence and at different positions upstream of genes in the genomic 3'-proximal domain of 2019-nCoV. The 2019-nCoV genome contains at least 14 predicted open reading frames (ORFs): ORF1a, ORF1b, S, 3, 4a, 4b, 5, E, M and N with sixteen predicted nonstructural proteins being encoded by ORF1a/b. Several unique group-specific ORFs that are not essential for virus replication are encoded by 2019-nCoV. The functions of these group-specific ORFs are unknown; however, by analogy to other coronaviruses, they may encode structural proteins or interferon antagonist genes. Open reading frames ORF2, -6, -7 and -8a are translated from subgenomic mRNAs predicted to encode the four canonical structural genes: a >150-kDa spike glycoprotein (S); a ~23-kDa membrane glycoprotein (M); a small envelope protein (E); and a ~50-kDa nucleocapsidprotein (N), respectively.

Example 2. Design siRNA Targeting Key Genes of 2019-nCoV

We designed multiple siRNA sequences, including both 25-mer and 21-mer oligos. Table 1 shows siRNA sequences, 25-mer blunt-end oligos and 21-mer sticky-end oligos, targeting various viral RNA (non-structure proteins). The characteristics of these sequences include but are not limited to: targeting conservative gene sequences, reasonable thermodynamic stability, and low toxic side effects. Table 2 shows siRNA sequences, 25-mer blunt-end oligos and 21-mer sticky-end oligos, targeting various viral RNAs (spike protein), where the siRNAs indicated in bold type are the most potent siRNA inhibitors and the siRNAs indicated in underlined type are the second best siRNA inhibitors. Table 3 shows the most potent siRNA oligos, 25-mer blunt-end oligos and 21-mer sticky-end oligos, targeting various other viral proteins and genes.

Example 3. Cell Culture Based Screening for Potent Anti-2910-nCoV siRNA Oligos

To identify the most potent siRNA for silencing 2019-nCoV genes in Vero cell culture experiments we first used psiCheck plasmid carrying 2019-nCoV gene sequences. We then used Vero cells infected with real 2019-nCoV to test the selected siRNA for their anti-2019-nCoV infecting activities.

A. Subcloning 2019-nCoV Virus Gene Fragments as Surrogates for siRNA Potency Examination in Vero Cells In order to investigate the degrading effect of siRNA candidates on targeted 2019-nCoV genes, we used a dual luciferase reporter vector, psiCHECK-2, with gene fragments of Papain like viral protein (nsp5), Conoravirus endopeptidase C30 (nsp6), RNA synthesis protein (nsp10), RNA-dependent RNA polymerase (nsp12), and structure proteins S, E, M and N. psiCHECK-2 Vectors are designed to provide a quantitative and rapid approach for initial optimization of RNA interference (RNAi). The vectors enable monitoring of changes in expression of a target gene fused to a reporter gene. The DNA fragments of nsp5, nsp6, nsp10, nsp12 and structure proteins S, E, M and N were amplified by PCR with specific primers to those genes, and then cloned into the multiple cloning sites of the psi-CHECK-2 Vector. In this vector, *Renilla* Luciferase is used as a primary reporter gene, and the siRNA targeting genes are located downstream of the *Renilla* translational stop codon.

Vero cells were seeded in 96-well plates and incubated for 12 h. The reporter plasmids (recombinant vectors) psi-nsp5, psi-nsp6, psi-nsp10, psi-nsp12, psi-S, psi-E, psi-M and psi-N, and siRNA candidates were co-transfected into Vero cells using Lipofectamine 2000 in DMEM without FBS. The blank psi vector is taken as a negative control. Six hours post-transfection, the media was replaced with DMEM supplemented with 10% FBS. 18, 24, 36 and 48 h post-transfection the activity of the firefly luminescence and *Renilla* Luciferase in each well was detected using the Dual Luciferase Kit. The siRNA candidates dramatically decreased luciferase activity, showing that siRNA could greatly inhibit the expression of the target genes of 2019-nCoV in vitro.

B. Infection of Vero Cells with 2019-nCoV

To investigate whether 2019-nCoV mRNAs for nsp5, nsp6, nsp10, nsp12 and structure proteins S, E, M and N can be directly degraded by the specific mechanism of RNA interference (RNAi), Vero cells were seeded in 24-well plates and transfected with selected therapeutic single siRNA or siRNA combination candidates using Lipofectamine 2000 in DMEM without FBS when the cell monolayer reached 80% confluency. The transfection efficacy control is Cy3-labeled siRNA. PBS was taken as a negative control. An siRNA with a sequence unrelated to 2019-nCoV was used as a further negative control. 24 h post-transfection the media containing the transfection reagent was replaced with fresh media supplemented with 2% FBS, and cells were infected with 2019-nCoV. One hour post-infection, the inoculation solution was replaced with DMEM supplemented with 10% FBS. 24 h post-infection the cells were harvested for RNA isolation and 5'-rapid amplification of cDNA ends (5'-RACE). In a parallel experiment, at 24, 48 and 72 h post-infection, the cell supernatants were harvested for viral titer determination. All experiments were performed under Biosafety level-2 conditions.

Viral RNA was extracted from the cell supernatants and one-step quantitative real-time PCR was performed with forward and reverse primers and a TaqMan probe specific to the 2019-nCoV isolate FRA/UAE spike protein. The total RNA from the harvested cells were extracted, and 5'-RACE assay were carried out with gene-specific primers for cDNA products of nsp5, nsp6, nsp10, nsp12 and structure proteins S, E, M and N. The single siRNA or siRNA combination with the high protection efficiency was selected for in vivo studies.

Figure 3:
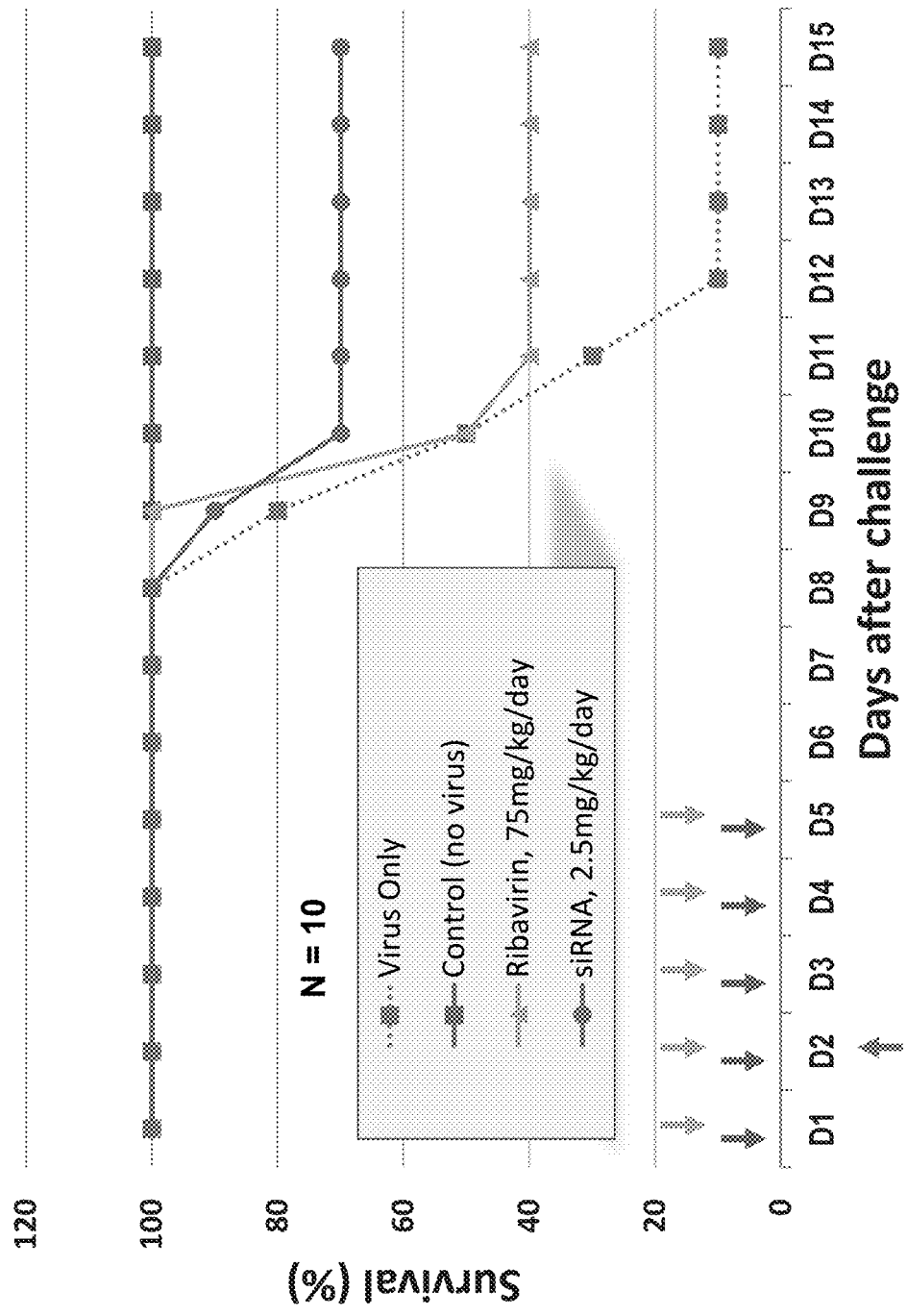
FIG. 3 shows intraperitoneal delivery of HKP-siRNA nanoparticle formulation demonstrated a prophylactic effect against H1N1 in the viral challenged mice (n=10). The HKP-siRNA combination (siRNA103-siRNA105 with a 1:1 ratio) at a concentration of 40 μg/2 ml was intraperitoneally administered on day 1, 2, 3, 4 and 5 (2.5 mg/kg/day, purple arrows). Viral challenges through intranasal administrations of 2×LD50 H1N1 (A/Puerto Rico/8/1934) were conducted on day 2 (red arrow) for the virus only, Ribavirin and siRNA treatment groups. Ribavirin as a positive control was administered through gavages of 200 ul to provide 75 mg/kg/day dosing over days 1-5 (orange arrows). The prophylactic efficacy of HKP-siRNA formulation was clearly better than that of Ribavirin.
Figure 4:
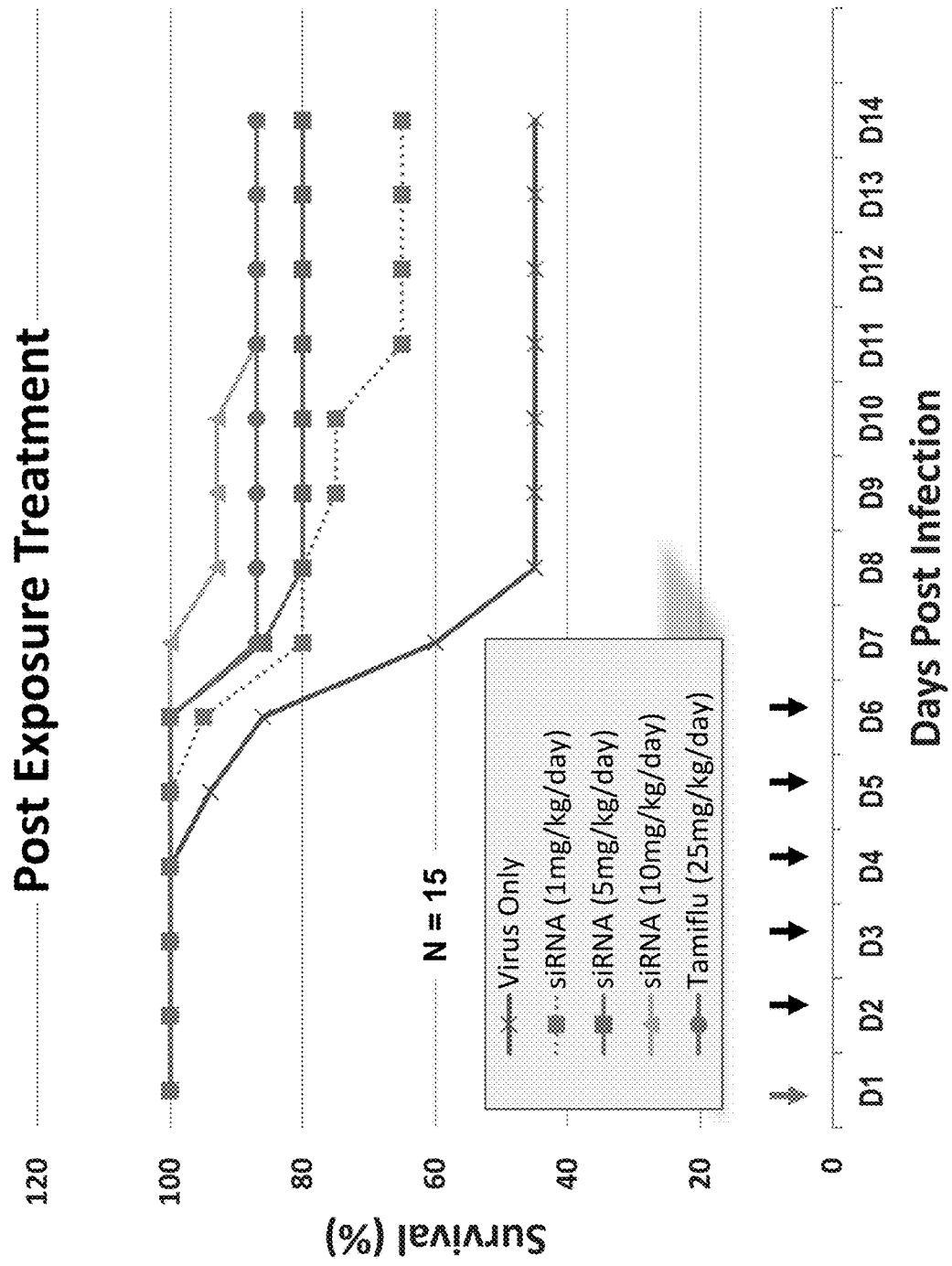
FIG. 4 shows intraperitoneal delivery of PAA-siRNA formulation demonstrated a therapeutic efficacy against H1N1 in the viral challenged mice (n=15). The viral challenges through intranasal administrations of 1×LD50 H1N1 (A/California/04/2009) were conducted on day 1 (red arrow) for the virus only, Tamiflu and siRNA treatment groups. The H1N1 challenged mice were treated with various dosages of PAA-siRNA combination (siRNA89-siRNA103 with a 1:1 ratio), 1 mg/kg, 5 mg/kg and 10 mg/kg, through intraperitoneal administration daily, from day 2 to day 6 (black arrows). Adapting the same route and dosing regimen, 25 mg/kg Tamiflu was also administered daily on the H1N1 infected mice. The therapeutic efficacy of 10 mg/kg/day of PAA-siRNA combination resulted in almost equal anti-influenza activity to that of 25 mg/kg/day of Tamiflu treatment.

In PBS-free DMEM medium (cell culture medium), Lipofectamine 2000 was used to co-transfect these reporter plasmids (contained different viral gene fragments) and the siRNAs (directed against these gene fragments) into Vero E6 cells. The siRNAs that do not target any viral genes were used as negative controls. Six hours after transfection, the ability of *Renilla* luciferase and firefly luciferase in each well to catalyze their respective substrates to emit fluorescence was tested with the Dual Luciferase Kit. When the fluorescence expression in the system decreases, it indicates that siRNAs inhibit the expression of luciferase. The decrease in the ability of the enzyme to catalyze the substrate to emit fluorescence means that the siRNA candidate drug molecules can effectively inhibit the expression of SARS-CoV-2 target genes. Using this method, we screened out multiple effective siRNAs (FIG. 3-5). In 293T and A549 cells, 8 selected siRNAs that have an inhibitory effect of more than 80% on the target gene in both cells (Among them, there are three types of siRNAs that have an inhibitory effect of more than 85% in these two cells: namely G32, R03, and R24). Especially in A549 cell lines, there are 5 siRNAs that have an inhibitory effect of more than 90% on the target gene. We further measured the EC50 of these siRNAs on the inhibition efficiency of the two cells. Among them, the $EC_{50}$ of Rec #3, which has the best inhibitory effect, was 0.3 pg/μL in A549 and 5.8 pg/μL in 293T cells. respectively.

Example 4. Verifying the Inhibitory Effect of siRNAs on SARS-CoV-2 Through In Vitro Cell Experiments Vero E6 cells were cultured overnight, and then transfected with different concentrations of siRNA (from 3.125 nM to 100 nM), and the cells were infected with SARS-CoV-2 at a specific MOI (multiplicity of infection). After culturing for several days, the virus infection rate was determined by the cytopathogenic effect. The % infection was calculated as the number of infected cells (expressing virus N protein, stained using a specific antibody) divided by the total number of cells counted as cell nuclei stained with Hoechst 33342 dye. Most siRNAs (SCo1, SCo2, SCo34, SCo36) showed a complete block of infection at the lowest concentration tested—namely 3.125 nM.

Example 5. HKP/siRNA Nanoparticle and Pulmonary Delivery

Figure 8:
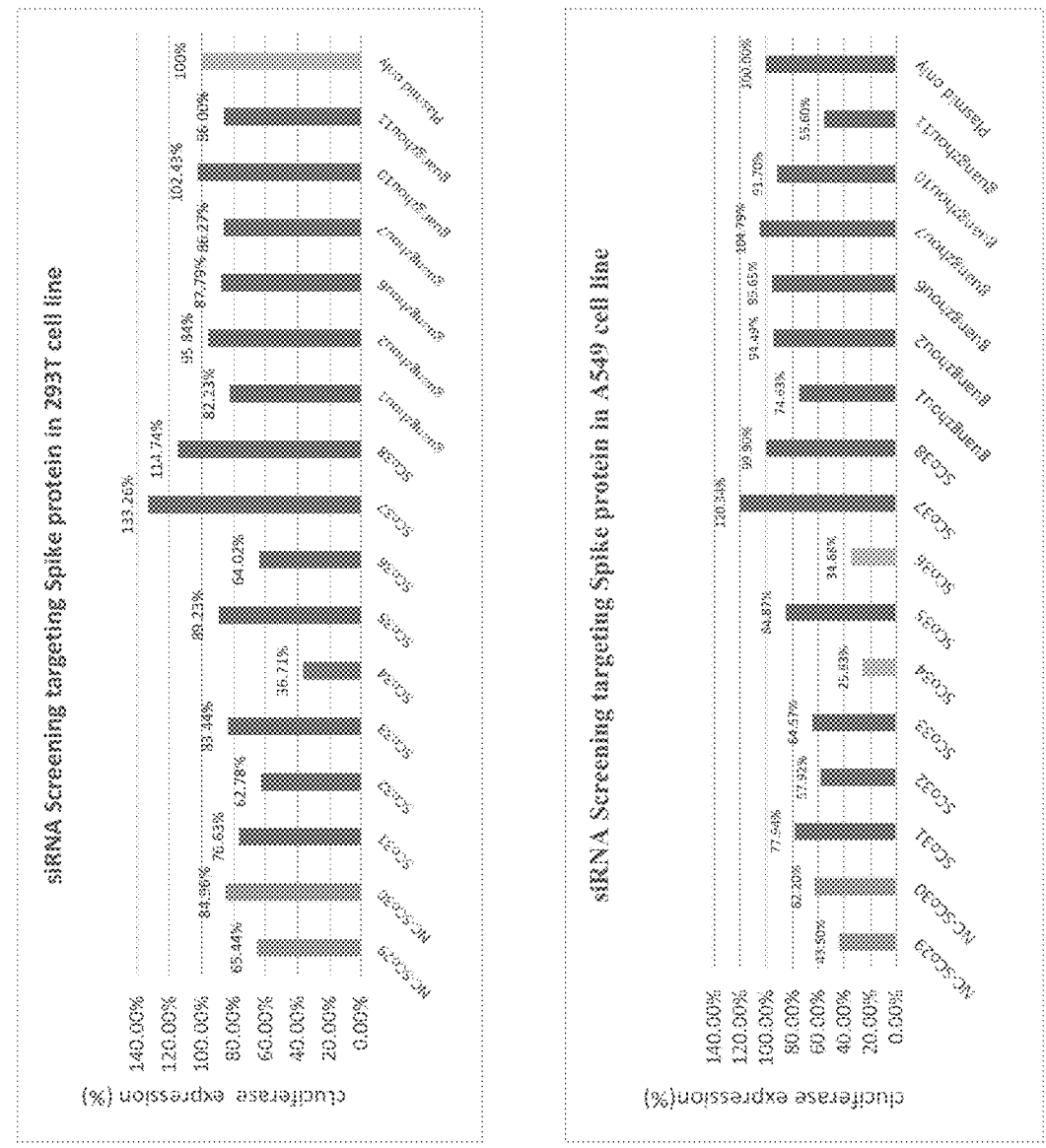
FIG. 8 shows two kinds of cells were used to screen siRNAs that target the S protein of SARS-CoV-2 (part I). The 293T (top) and A549 cells (bottom) were used to detect 14 siRNAs, such as SCO31-38, Guangzhou1 and Guangzhou2, to find out the siRNAs with better inhibitory effect on S protein gene expression. The negative control siRNA was SCO29 and SCO30 and do not inhibit the expression of any genes.
Figure 9:
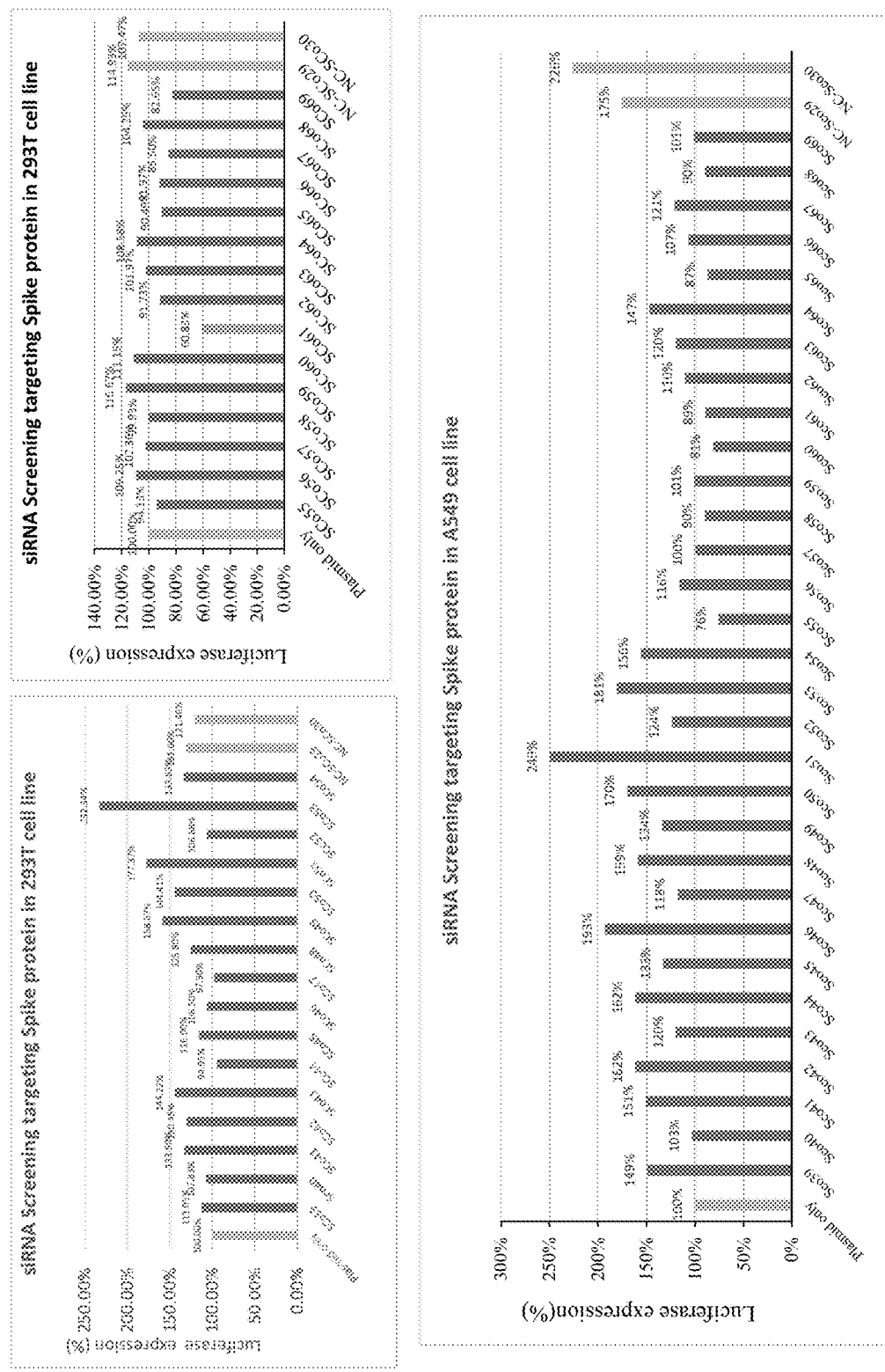
FIG. 9 shows two kinds of cells were used to screen siRNAs that target the S protein of SARS-CoV-2 (part II). The 293T and A549 cells were used to detect 31 siRNAs such as SCO39-69, and identify siRNAs with better inhibition effect on S protein gene expression.
Figure 10:
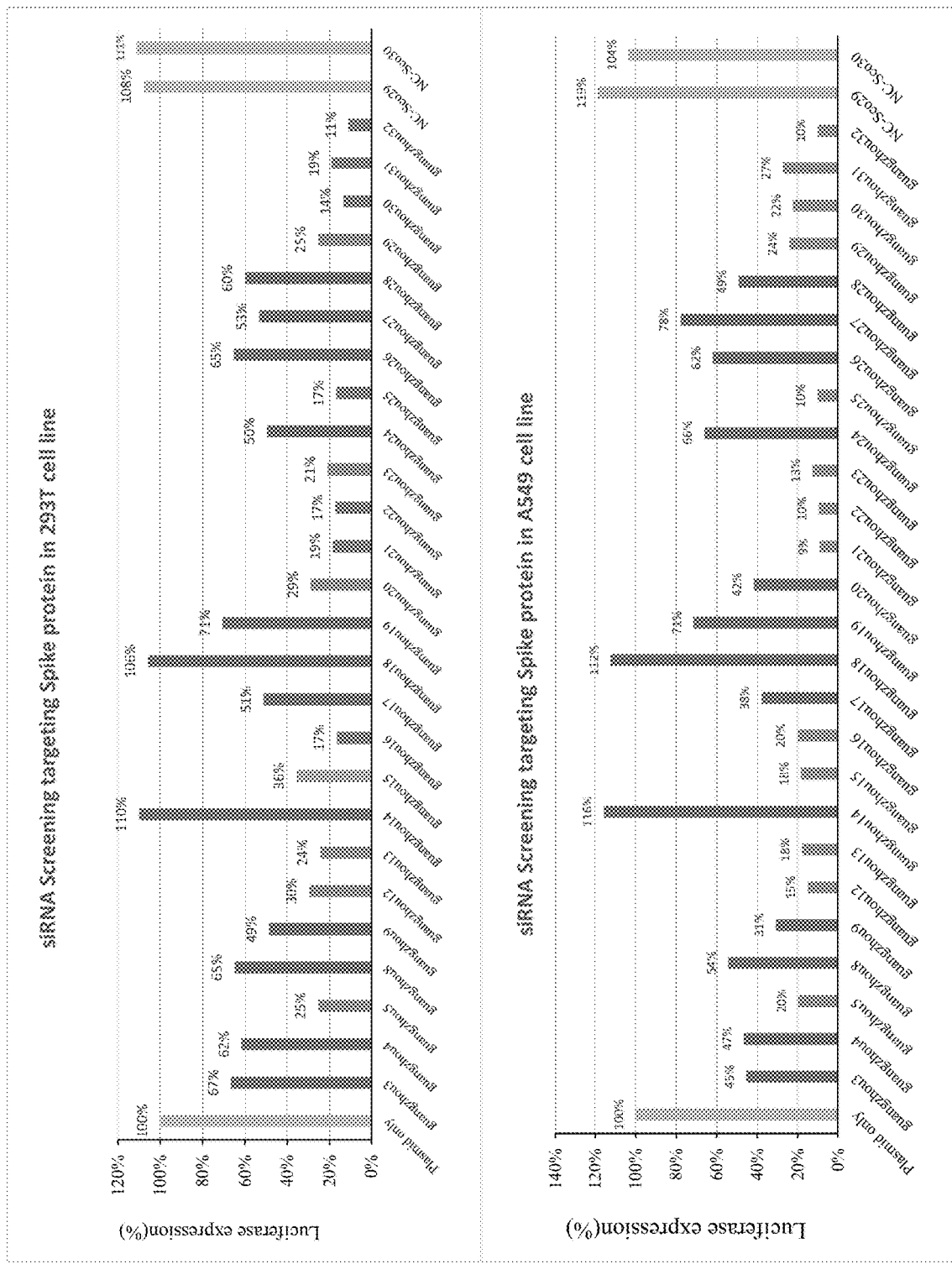
FIG. 10 shows two kinds of cells were used to screen siRNAs that target the S protein of SARS-CoV-2 (part III). The 293T and A549 cell lines were used to detect 26 siRNAs such as guangzhou3-5, guangzhou12-20, and identify siRNAs with most potent inhibition effect on S protein gene expression.
Figure 11:
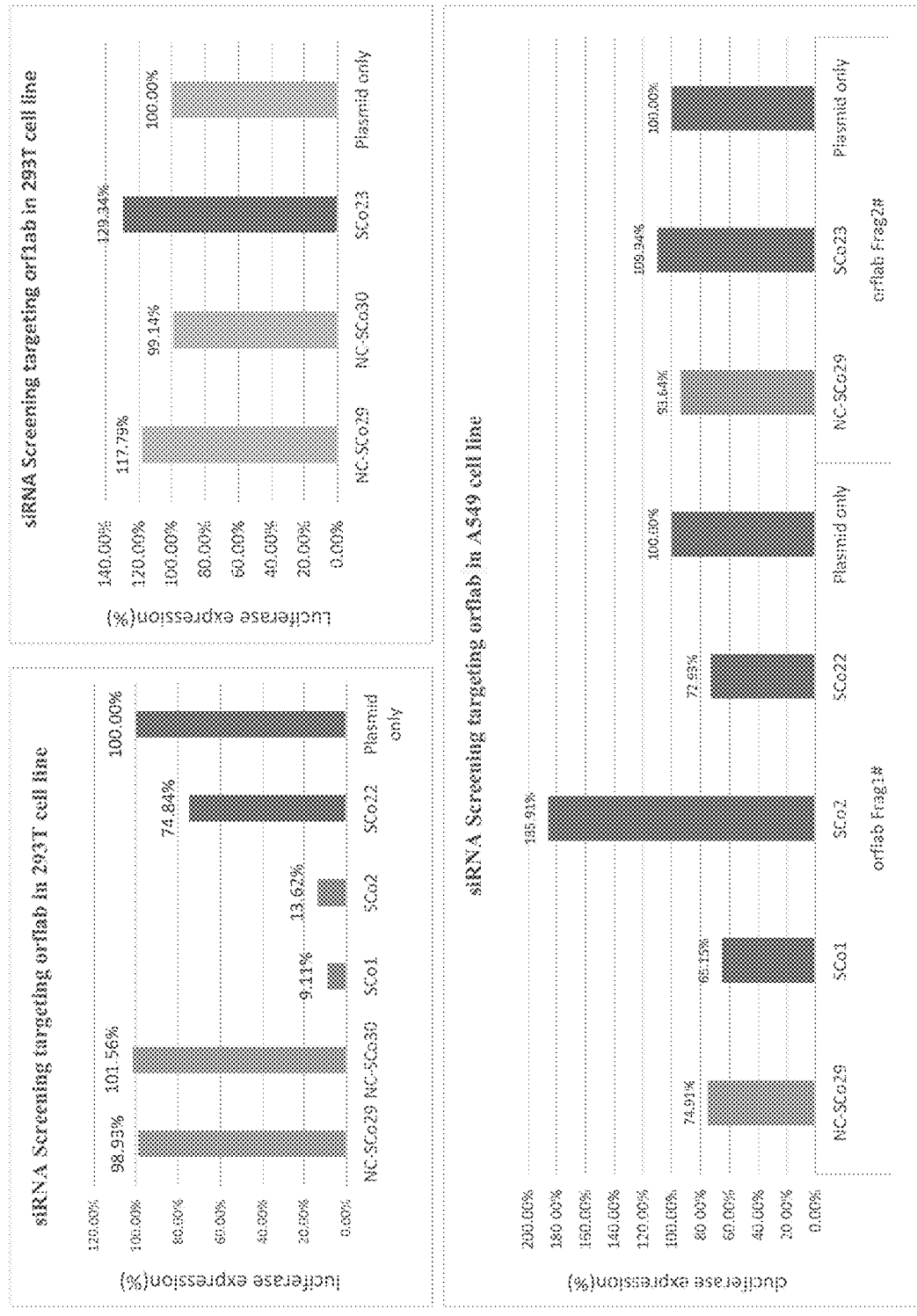
FIG. 11 shows that siRNAs targeting the ORF1AB of SARS-CoV-2 were screened by two kinds of cells (part I). The 293T (top left and right) and A549 cell lines (bottom) were used to detect 4 siRNAs, including SCO1, SCO2, SCO22, SCO23, to identify siRNAs with potent inhibition effect on ORF1Ab gene expression.
Figure 12:
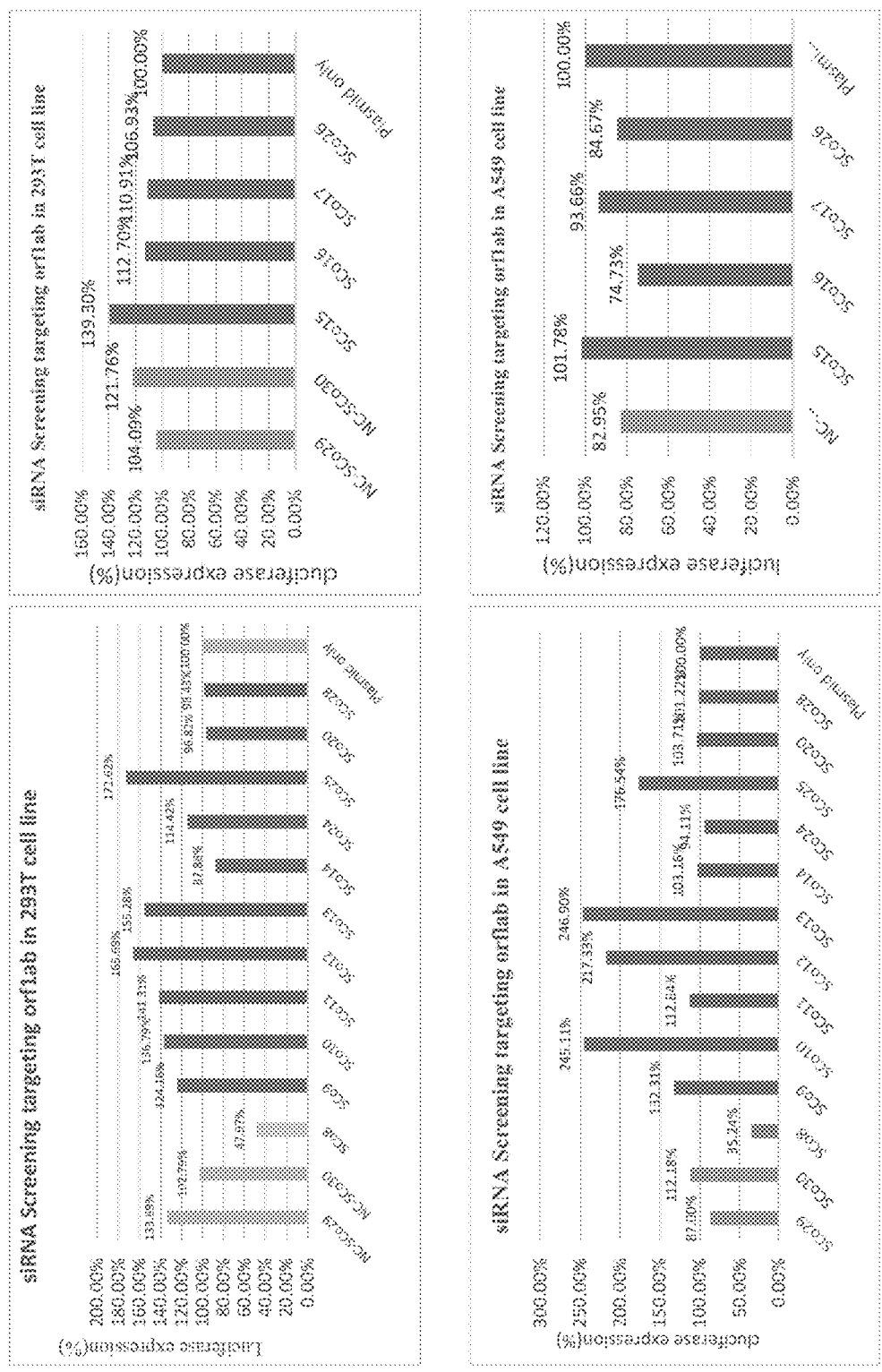
FIG. 12 shows siRNAs targeting ORF1AB of SARS-CoV-2 were screened by two kinds of cells (part II). The 293T (top left and right) and A549 cell lines (bottom left and right) were used to detect 15 siRNAs, including SCO8-17, SCO20, SCO24, SCO25, SCO26, SCO28, to identify siRNAs with a potent inhibition effect on ORF1Ab gene expression
Figure 13:
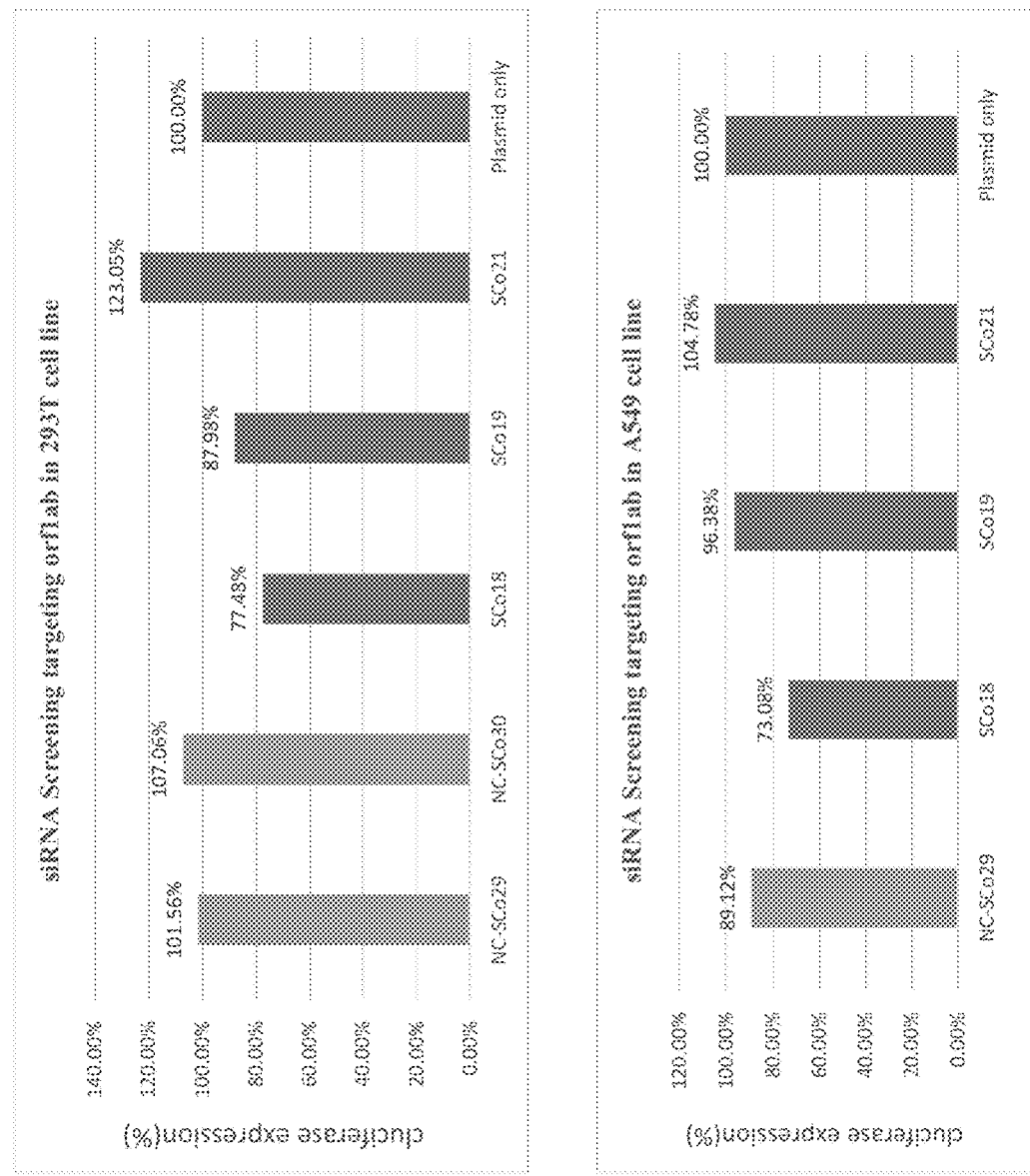
FIG. 13 shows two kinds of cells were used to screen siRNAs that target the ORF1AB of SARS-CoV-2 (part III). The 293T (top) and A549 (bottom) cell lines were used to detect 3 kinds of siRNAs, SCo18, SCo19, SCo21, to identify siRNAs with potent inhibition effect on ORF1AB gene expression.
Figure 15:
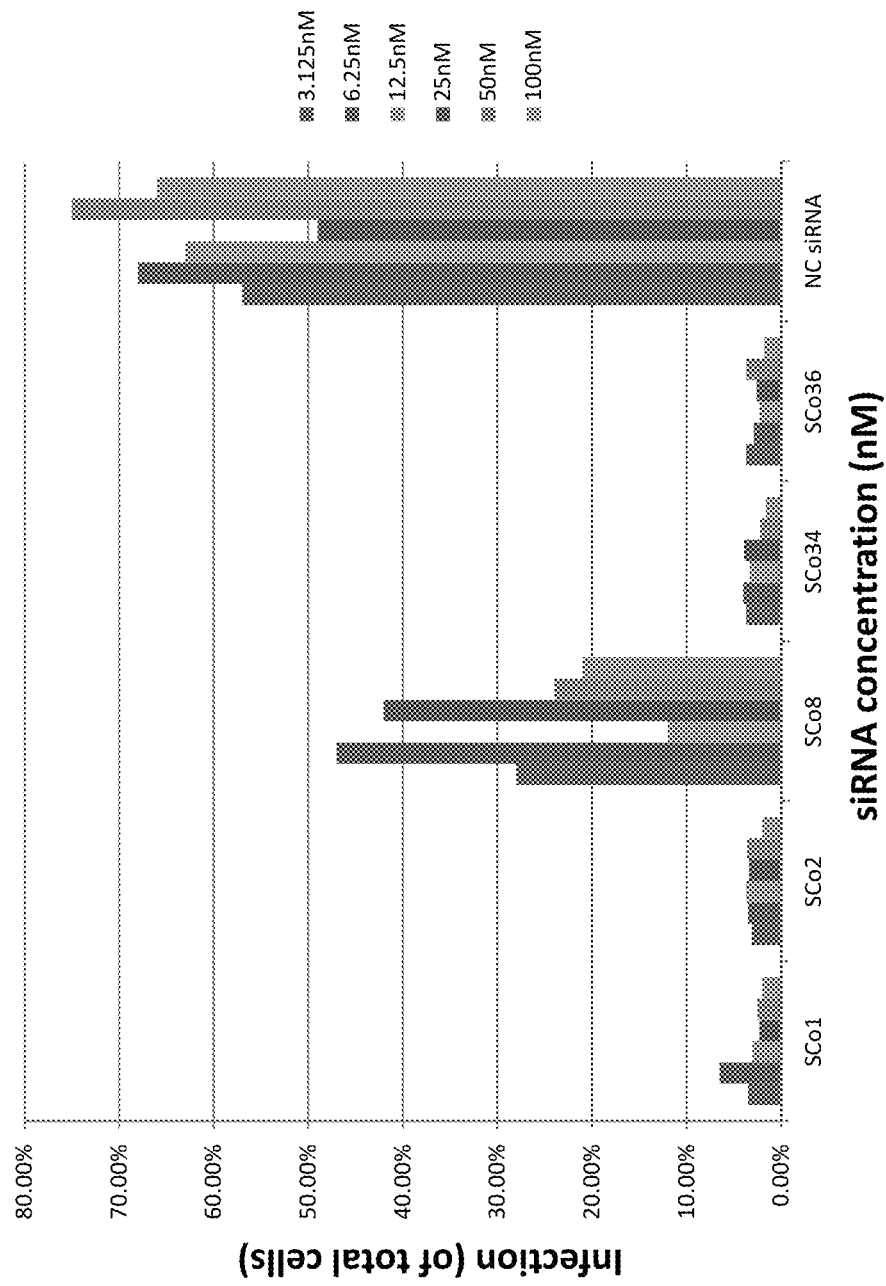
FIG. 15 shows the siRNAs were tested individually at varying concentrations for inhibition of the virus. Most siRNAs (SCo1, SCo2, SCo34, SCo36) showed a complete block of infection at the lowest concentration tested—namely 3.125 nM.

Histidine-Lysine co-polymer (HKP) siRNA nanoparticle formulations can be prepared by mixing together aqueous solutions of HKP and siRNA in a 4:1 ratio by molecular weight (N/P). A typical HKP/siRNA formulation will provide nanoparticles with an average diameter of 150 nm. The self-assembled HKP/siRNA nanoparticles were resuspended in aqueous solution, lyophilized into dry powder, and then resuspended in RNase free water. After oral-trachial administration of HKP/siRNA (red labeled) nanoparticles to the mouse respiratory track we were able to observe fluorescent siRNA in the upper (bronchi), and lower airway (alveoli). We compared the efficacy of RNAi of cyclophiline B in the lung after oraltrachial deliveries of three different doses of siRNA with HKP, DOTAP and D5W. HKP-mediated delivery demonstrated efficient RNAi of the target gene at the 20 μg dose (FIG. 8).

Example 6. Preparation and Identification of Nanoparticle Preparations

Figure 16:
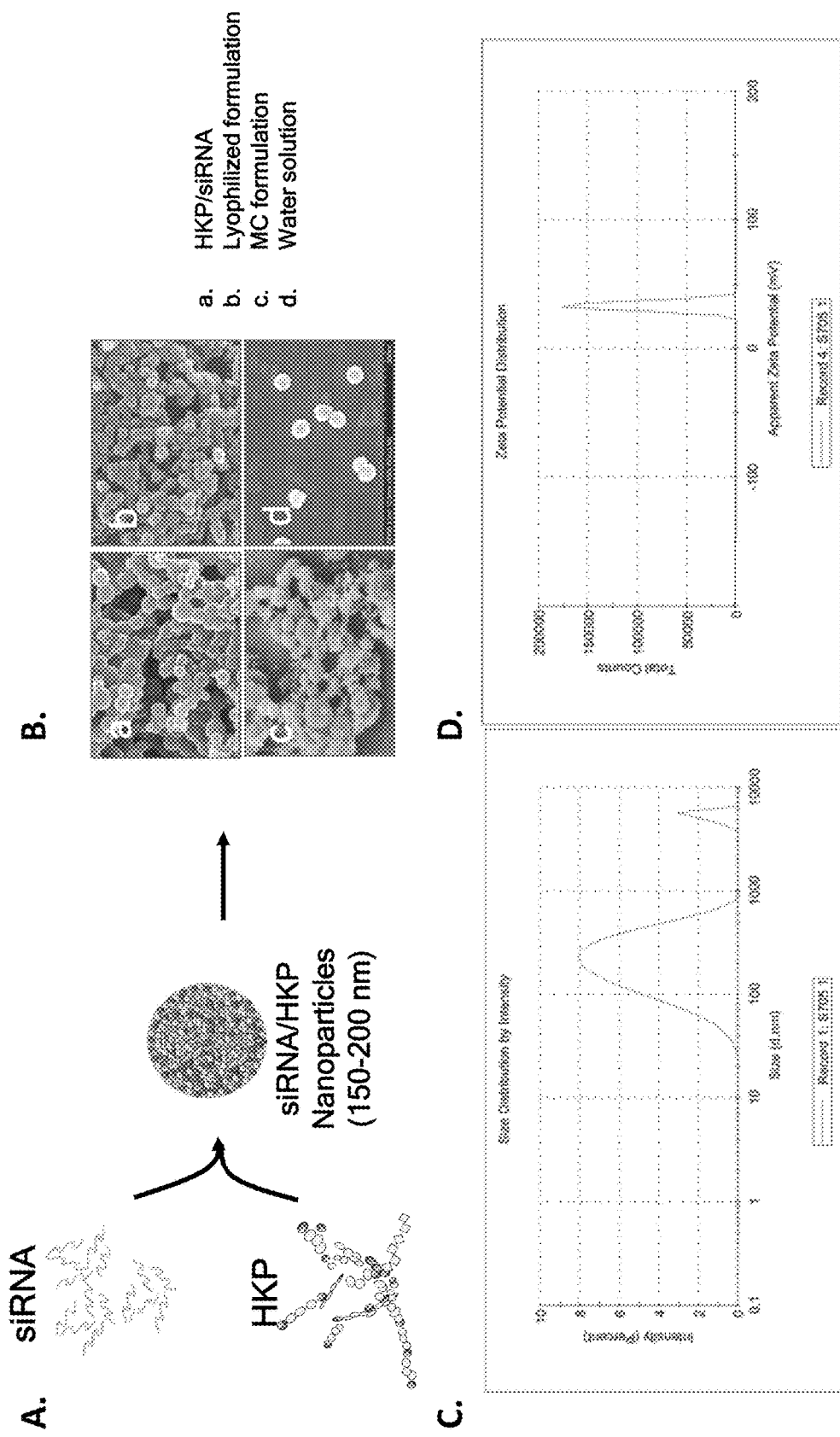
FIG. 16 shows the preparation and characterization of polypeptide nucleic acid nanomedicine. Self-assembly of siRNAs with HKP to form nanoparticles through electrostatic interaction. The average diameter is 150-200 nm, and the Zeta potential is greater than 30 mV.

Histidine-lysine copolymer (HKP) and siRNA aqueous solution were mixed at a molecular weight ratio (N/P) of 4:1 to prepare an HKP/siRNA nanoparticle formulation (FIG. 16A). The average diameter of a standard HKP/siRNA nanoparticles is generally between 150-200 nm. The self-assembled HKP/siRNA nanoparticles can be suspended in the aqueous solution. After being lyophilized into a dry powder, it can be resuspended in Ribonuclease-free water (FIG. 16B). Malvern particle size analysis was used to analyze and detect the formulated nanoparticles preparations. The results show that the average size of the nanoparticles is 193.4 nm (FIG. 16C) and the Zeta potential is 32.7 mV (FIG. 16D), which indicates that the results meet the expected requirements.

Example 7: Nebulized Inhalation Administration Test

To test the development potential of nanomedicine formulations composed of HKP and siRNA in the treatment of respiratory/pulmonary diseases by nebulized inhalation, we further carried out aerosolization tests on the active pharmaceutical ingredient (API siRNA), the delivery carrier polypeptide (HKP), and the nano-preparation (both siRNA and HKP). Moreover, we also analyzed the physical and chemical properties and biological activities of the API, excipients, and drug preparations before and after aerosolization in vitro.

In the clean bench, we clean and disinfect the Zhengyuan YS31E atomizer in advance, and insert the spray port (including the nozzle) into a 50 mL sterile centrifuge tube, insert the centrifuge tube into the ice box, make the centrifuge tube and the atomizer at right angles, and tilt them separately 45°; prepare a specific concentration of siRNA, HKP or STP705 aqueous solution, take and place most of the solution in the atomizer, start atomization, 10-20 minutes (atomize 2 mL, about 6-8 minutes). After the atomization, collect the condensed solution (B solution) in the 50 mL centrifuge tube, the remaining solution in the atomizer is C solution, and the original configuration without the atomizer is A solution. Then proceed as follows, 1) Use the spectrophotometer to measure the concentration of the protein (HKP) and/or nucleic acid (siRNA) in the three solutions A, B, and C before and after nebulization, 2) confirm the integrity of the siRNA and STP705 by electrophoresis, 3) Analyze the inhibitory effect of siRNA on target genes by transfecting cells.

Figure 17:
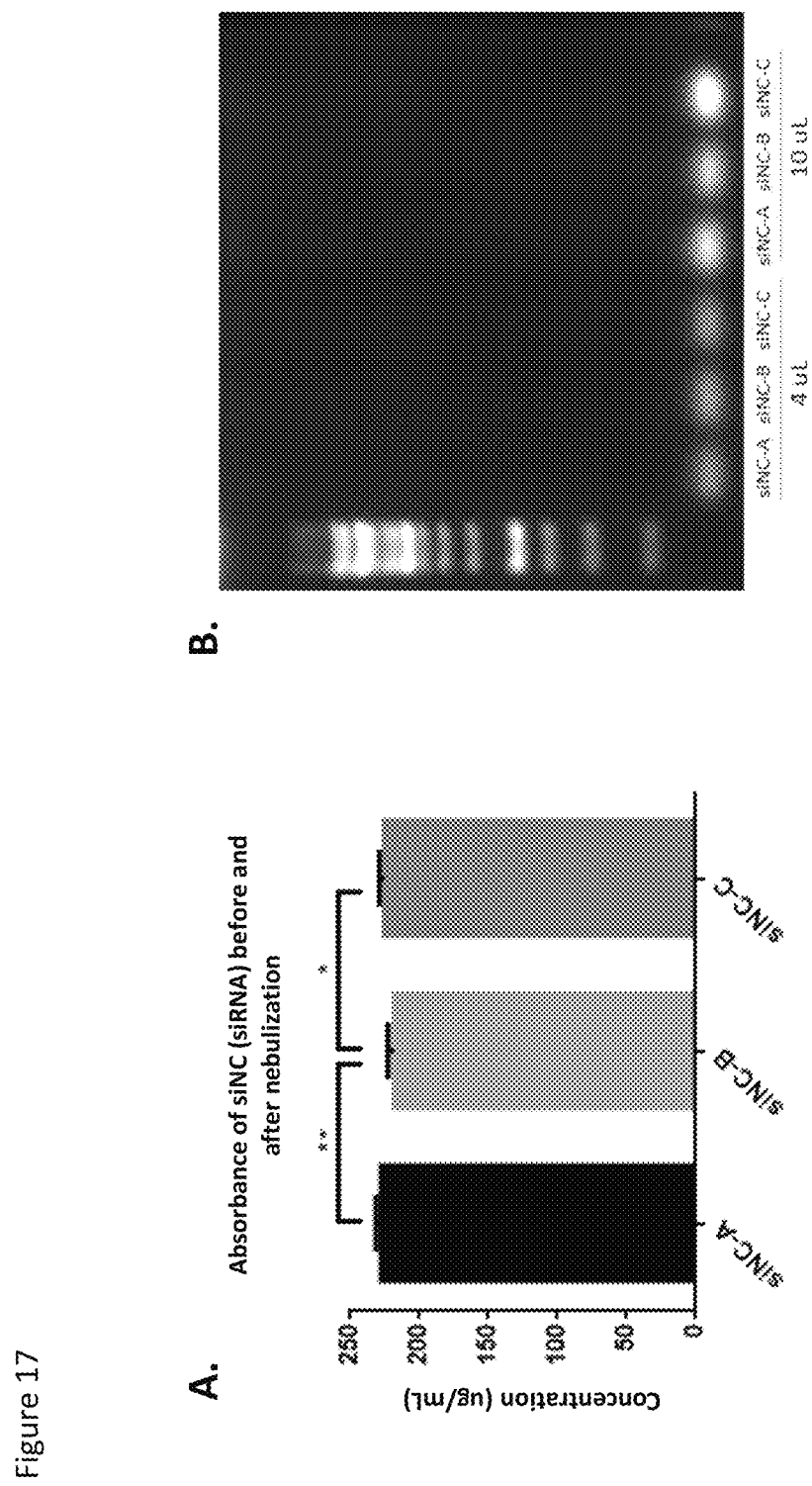
FIG. 17 shows the concentration and stability analysis of siRNA before and after nebulization. After the siRNAs are atomized through the handheld nebulizer, there is little change in the concentration of the siRNAs sprayed or remained in the nebulizer, and the molecular structure remains stable.

Firstly, we tested the stability of the siRNA solution after atomization (FIG. 17A). The results showed that after 0.2 mg/mL siRNA was nebulized, the spectrophotometer test showed that the concentration dropped by about 4% (from 227.85 ug/mL to 218.69 ug/mL), and there was no affected on the remaining siRNA solution in the nebulization device. Moreover, the electrophoresis results were also confirmed the above results (FIG. 17B), that is, except for the concentration of the siRNA solution was decreased slightly after aerosolization, the fragment of siRNAs were retaining complete.

Figure 18:
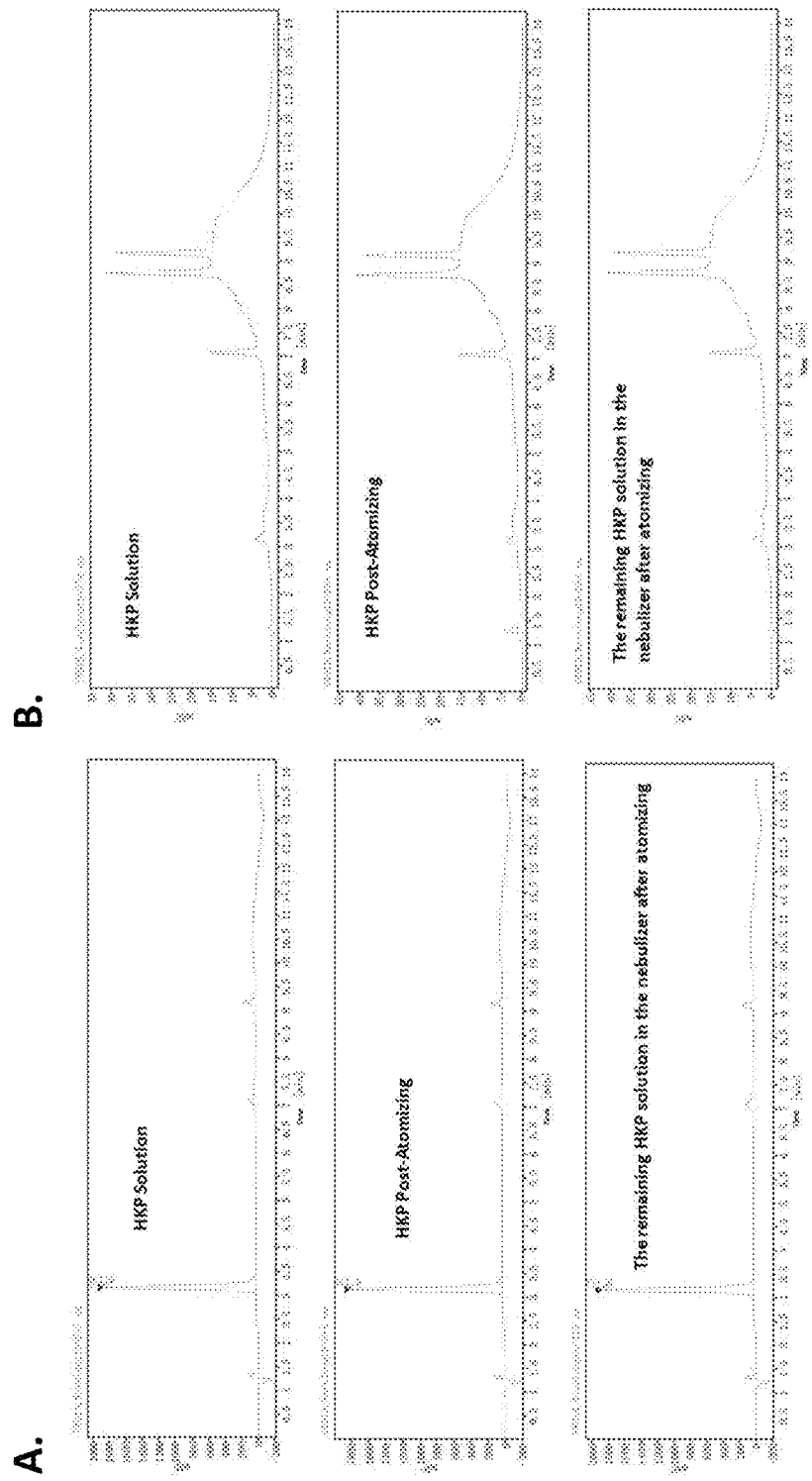
FIG. 18 shows a comparison between HKP before and after nebulization. After the polypeptide nano-delivery vector is atomized by a handheld nebulizer, it is analyzed by HPLC (two models), indicating that the molecular structure remains stable.
Figure 22A:
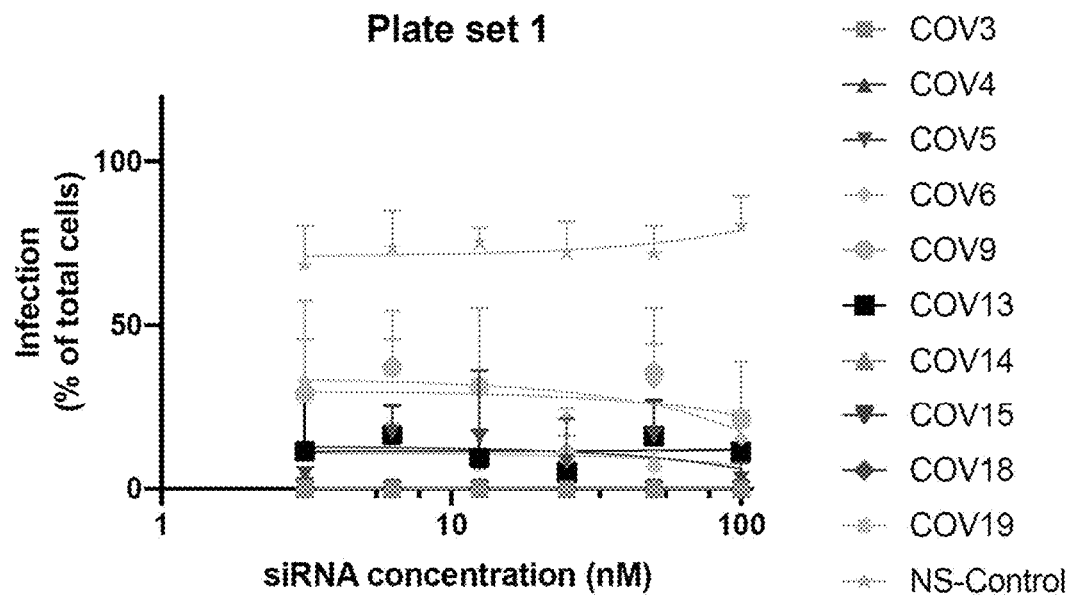
FIGS. 22A and 22B show tested of individual siRNAs at varying concentrations for inhibition of the virus.
Figure 22B:
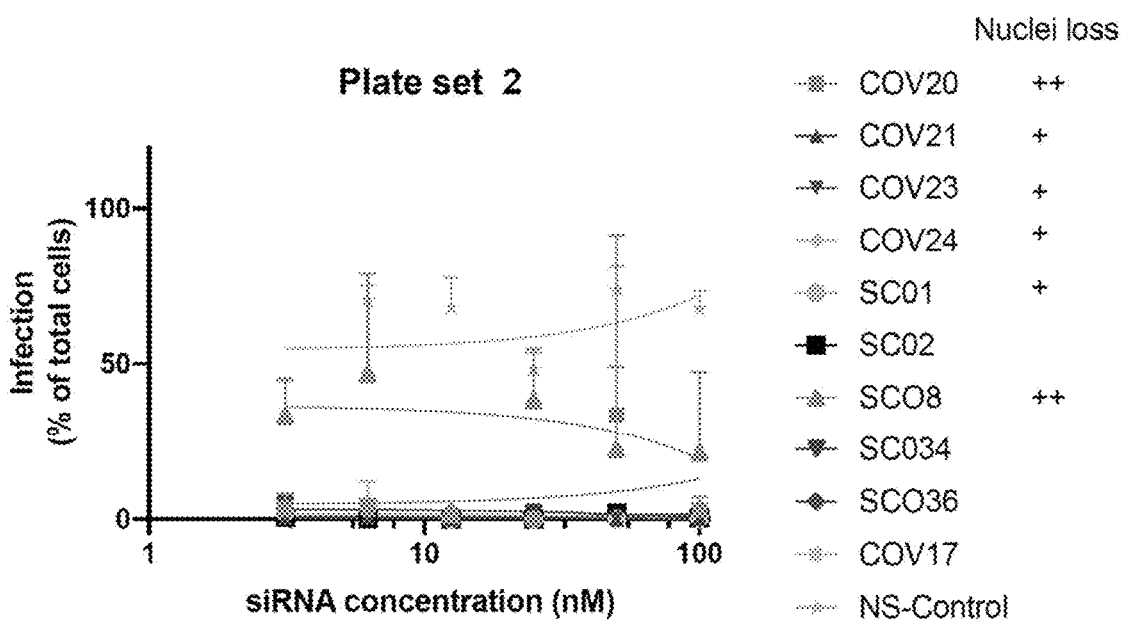

In order to analyze the influence of atomization on the HKP polypeptide delivery system, the present invention uses a YS31E atomizer to atomize the HKP solution (with a concentration of about 0.8 mg/mL). We collected three different solutions of the above HKP solution, namely A, B, and C, and then tested them with HPLC. The results confirmed that the concentration of the sprayed solution was reduced, but the HKP maintained a complete structure after atomization, indicating that the atomization had no significant effect on the structure of HKP (FIG. 18).

Example 8. HKP/siRNA Formulation for Intraperitoneal Delivery

During evaluation of prophylaxis and therapeutic benefit of siRNA inhibitors against influenza infection, we tested HKP/siRNA formulation through intraperitoneal administration using different dosage and regimens. Based on the observations of these treatment results, we found that the prophylactic effect of HKP/siRNA (two siRNAs are specific to influenza genes) exceeded the effect of Ribavirin (FIG. 3). Similarly, the therapeutic effect of HKP/siRNA (two siRNAs specific to influenza genes) is greater than the effect of Tamiflu (FIG. 4).

Example 9. SLiC/siRNA Nanoparticles

SLiC Liposome Preparation

Conventional methods were first tried to prepare liposomes with the newly synthesized SLiC molecules, such as the thin film method, solvent injection etc., with little success. Maurer et al., have reported a method of liposome preparation in which siRNA or oligonucleotide solution is slowly added under vortexing to a 50% ethanol solution (v/v) of liposome and ethanol is later removed by dialysis. This provided nanoparticles that were small in size and homogeneous. In this method siRNA was directly wrapped by cationic lipids during formation of liposome, while in most other methods siRNA or nucleic acid molecules are loaded (or entrapped) into preformed liposomes, such as Lipofectamine 2000.

Lipids dissolved in ethanol are in a metastable state in which liposomes are not very stable and tend to aggregate. We then prepared un-loaded or pre-formed liposomes using a modified Maurer method. We found that stable liposome solution could be made by simply diluting ethanol to the final concentration of 12.5% (v/v). Liposomes were prepared by addition of lipids (cationic SLiC/cholesterol, 50:50, mol %) dissolved in ethanol to sterile dd-$H_2O$. The ethanolic lipid solution was added slowly under rapid mixing.

Slow addition of ethanol and rapid mixing were required for successful preparation of SLiC liposomes, as the process allows formation of small and more homogeneous liposomes (FIG. 5). Unlike conventional methods in which siRNAs are loaded during the process of liposome formulation and ethanol or other solvent is removed at end of manufacturing, our SLiC liposomes were formulated so ethanol remained in the solution such that the liposomes were thought to be still in a metastable state. When the siRNA solution was mixed/loaded with a liposome solution, the lipid's cationic groups interact with anionic siRNA and condense to form cores. The metastable state of the SLiC liposomes helped or facilitated the liposome structure transformation to entrap siRNA or nucleic acids more effectively. As a result of the entrapment of siRNA, SLiC liposomes become more compact and homogeneous.

Physiochemical and Biological Characterization of SLiC Liposome

After liposome formation, we developed an array of assays to characterize the physicochemical properties of SLiC liposomes, including particle size, surface potential, morphology study, siRNA loading efficiency and biological activity, etc. The particle size and zeta-potentials of SLiC liposomes were measured with Nano ZS Zeta Sizer (Malvern Instruments, UK). Each new SLiC liposome was tested for particle size and zeta-potential when the ethanol content changed from 50% to 25% and to 12.5%. Data were derived from formulations of different ethanol contents. All SLiC liposomes were prepared at a concentration of 1 mg/ml and loaded with siRNA (2:1, w/w). Each of the SLiC Liposomes was composed of cationic SLiC and cholesterol dissolved in ethanol at 12.5%, e.g. TM2 (12.5).

Further analysis of the physiochemical perimeters of the SLiC liposome suggested that ethanol concentrations were positively proportional to particle sizes (the lower the ethanol concentration, the smaller the particle size), but negatively proportional to zeta-potential (the lower of ethanol concentration, the higher the zeta-potential at the same time). The higher surface potential renders particles more stable in solution. In addition to stability in solution, data shown later further indicated that toxicity also was lower with lower ethanol concentration. Accordingly, in light of these factors, an ethanol concentration of 12.5% (v/v) was selected as the solvent to suspend cholesterol as well as SLiC into the master working stock solution before they were used to prepare liposome formulations.

In contrast to bare SLiC liposome formulations, liposome particle sizes became much smaller when they were loaded with siRNA at 2:1 (w/w) resulting in particle sizes in the range of 110 to 190 nm in diameter and much lower PDI values. Conventional consideration of liposomal structure dictates that siRNA is loaded or interacted with cationic lipids through electrostatic forces, and liposomes wrap siRNA to form spherical particles in order to reduce surface tension. As the result, the liposomes particle sizes became much smaller after loading with siRNA. Liposomes formulated with siRNA also have lower surface charge, which could be explained by the neutralizing effect from loaded siRNA. The inhibiting effects of SLiC-mediated siRNAs delivery were confirmed with anti-cyclophilin-B siRNAs on the expression of cyclophilin-B.

Example 10. Airway Delivery with Mouse Model

Human host-cell dipeptidyl peptidase 4 (hDPP4) and ACE2 and NRP1 have been shown to be the receptors for 2019-nCoV. However, the mouse is not a suitable small-animal model for 2019-nCoV as it has no receptor that is recognized and bound by the virus. In this study, the mice were sensitized to 2019-nCoV infection by transduction with an Adenoviral or Lentiviral vector expressing hDPP4 in the respiratory tract. This mouse model was used to investigate the efficiency of the siRNA in inhibiting 2019-nCoV infection in vivo. The siRNA combination candidate was delivered by encapsidation with the HKP-SLiC nanoparticle system. We performed all mouse studies under Biosafety level-3 conditions.

All BALB/c mice were 18 weeks old and tested as specifically pathogen-free at the beginning of this study. To develop susceptibility to 2019-nCoV, 30 mice of an Adenoviral vector group and 30 mice of a Lentiviral vector group were transduced with Adenoviral and Lentiviral vectors expressing hDPP4, respectively. Another 20 mice were transduced with empty Adenoviral or Lentiviral vector as controls. For the Adenoviral vector group, the hDDP4 gene was cloned into the Ad5. Then, MLE 15 cells were transduced with Ad5-hDDP4 at an MOI of 20. The supernatant were collected at 48 h post-infection. The mice were transduced intranasally with $10^8$ pfu of Ad5-hDDP4. For the Lentiviral vector group, the hDDP4 gene was cloned into the plasmid pWPXLd. Then, pWPXLd-hDPP4, along with packaging vector, psPAX2 and envelope vector, pMD2.G, was co-transfected into the packaging cell line HEK 293T using the calcium phosphate method. At 48 h post-transfection, the constructed viral vector was harvested and purified, and transducted with CHO cells. The lentivirus was harvested and concentrated. The mice were transduced intranasally with lentivirus expressing hDPP4 at titers of $10^8$ transducing units/ml (TU/ml).

After confirmed that hDPP4 was expressed in the respiratory tract of the mice by western blot, Adenoviral and Lentiviral vector groups were further divided into prophylactic, therapeutic and control subgroups, with ten mice in each subgroup. Ten mice from Ad5-hDDP4 or psPAX2-hDDP4 prophylactic subgroup were intranasally inoculated with the siRNA combination encapsidated with HKP-SLiC nanoparticle system 24 h before inoculation. 24 h later, all eighty mice, including those transduced with empty vector, were infected intravenously with 105 pfu of 2019-nCoV. The prophylactic, therapeutic and control subgroup were intranasally inoculated with siRNA or PBS at 0, 24, 48, 72 and 96 h post-infection.

All mice were weighed and the survival of each subgroup was counted daily. The nasal washes were collected at 1, 3, 5, 7, 9, and 14 day post-infection for the viral titration. Two infected mice from each group were sacrificed at 3 and 5 day post-infection, respectively. Tissue, including lung, trachea, spleen, liver, heart, brain and kidney, was collected for pathological and virological study.

To determine viral titers, the tissue samples were homogenized in DMEM, and clarified by centrifugation. Both tissue suspensions and nasal washes were 10-fold serially diluted. The dilutions were added to the Vero cells monolayers grown in 96-well plates. The cytopathic effects (CPEs) were observed on day 3 post-infection, and the $TCID_{50}$ was calculated by the Reed-Muench method.

To investigate the efficiency of siRNA candidates in inhibiting viral gene expression, the total RNA was extracted from the tissues and the one-step quantitative real-time PCR were performed with forward, reverse primers and TaqMan probe specific to the conserved region of nsp12 (RNA-dependent RNA polymerase) of 2019-nCoV.

Example 11. Intraperitoneal siRNA Nanoparticle Solution

In Vivo Administration of siRNAs

The in vivo experiments were conducted using 6-8 week old female mice. For inoculation, allantoic fluid containing the influenza virus at a dose of $5 \times 10^4$ $EID_{50}$/mL was used. The infectious activity of the virus in allantoic fluid was determined in vivo by titration of lethality. Titers of the virus were calculated using the Reed and Muench method (17a). Non-infected mice that were kept in the same conditions as the infected animals were used as a negative control. Virus was administered to the animals intranasally under a light ether anesthesia. Each group of animals contained 15 mice. siRNA (1:1 ratio of anti-influenza siRNAs 89 and 103) complexed with PAA as described above, was administered to the animals at the dose of 1-10 mg/kg of body weight. siRNA was administered intraperitoneally (200 ul per injection). Control animals received PAA without siRNAs.

Animals were observed for 14 days post inoculation. The mortality of the animals in control and experimental groups was registered daily. The mortality percentage (M) was calculated in each group as: M=N/Nt where: N—the number of animals died within 14 days after infection; Nt—the total number of animals in the group. The index of protection (IP) was calculated as: IP=((Mc−Me)/Mc)×100%, where: Mc and Me—percentage of mortality in control and experimental groups, correspondingly. The median day of death (MDD) within 14 days was calculated as: MDD=($\Sigma$ N D)/Nt, where: N—the number of animals surviving D days; Nt—total number of animals in the group. Tamiflu (oseltamivir phosphate, Roche, Switzerland) was used as a reference compound. It was administered at a dose of 25 mg/kg by the same protocol.

Intraperitoneal administration could be a viable alternative, especially in patients with severe influenza or Covid19 infection with low gas-exchange volume and/or those on mechanical lung ventilation. Since siRNAs of the same length show similar properties (charge, hydrophobicity, molecular weight etc.) and since siRNAs can be rapidly designed and manufactured, it is feasible that nanoparticle-mediated siRNA delivery may form an intermediate therapeutic strategy in treating rapidly emerging influenza virus or coronavirus strains with high mortality rates that do not respond to existing therapies, while vaccines to protect the general population are under development. The siRNA cocktail demonstrated in this manuscript may provide significant value as a prophylactic/therapeutic with broad anti-Covid19 strain coverage and this coverage may well extend to as yet unidentified Covid19 strains that may emerge in the future.

treating rapidly emerging influenza virus strains with high mortality rates that do not respond to existing therapies, while vaccines to protect the general population are under development. The siRNA cocktail demonstrated in this manuscript may provide significant value as a prophylactic/therapeutic with broad anti-influenza strain coverage and this coverage may well extend to as yet unidentified Influenza strains that may emerge in the future.

We demonstrated in this study that polymeric nanoparticle-mediated delivery of a combination of two siRNAs, via IP administration, can result in a potent antiviral effect in the viral-challenged animals. Histidine Lysine Co-Polymer (HKP) nanoparticle-mediated siRNA delivery has been well validated through multiple routes with various animal models. We recently completed a full scale safety study for HKP-siRNA nanoparticle formulation via subcutaneous administration into both mouse and monkey models (data not shown). When HKP-siRNA103/105 formulation was IP administrated (10 mg/kg/day), a prophylactic and therapeutic benefit was obtained that was greater than that observed with Ribavirin (75 mg/kg/day) in protecting mice from exposure to a 2×LD50 dose of the virus. The data obtained shows that IP injection of peptide nanoparticles containing siRNAs or of a polycationic delivery vehicle carrying siRNAs can both ameliorate the lethality induced by Influenza infection in mice and therefore has the ability to overcome some of these barriers. The amphiphilic poly (allylamine) (PAA) formed polymeric micelles (PM) has been evaluated for siRNA delivery via the GI tract (33), resulting in efficient siRNA delivery and endosome/lysosome release. PAA and siRNA can be self-assembled into complexes with nano-sized diameters (150-300 nm) and cationic surface charge (+20 to 30 mV). When we IP administrated PAA-siRNA89/103 formulation (10 mg/kg) a therapeutic antiviral activity was observed equivalent to that of Tamiflu (25 mg/kg). These results clearly demonstrated that polymeric nanoparticle delivery of siRNA combinations can provide a prophylactic/therapeutic response against newly emergent strains of influenza virus.

Example 12. Non-Human Primate Study

Currently, there is neither an effective vaccine nor drug available for a prophylatic or therapeutic strategy against 2019-nCoV. Recently, the rhesus macaque has been developed as a model for 2019-nCoV using intratracheal inoculation. Similar to humans, the infected monkeys showed clinical signs of disease, virus replication, and histological lesions, indicating that rhesus macaque is a good model for evaluation of the vaccine and antiviral strategy against 2019-nCoV infection. To investigate the efficiency of the siRNA on protecting and healing from 2019-nCoV infection, we performed the non-human primate study in rhesus macaques. The siRNA cocktail candidate was encapsidated with HKP-SLiC nanoparticle system, and administered intratracheally. This monkey study was carried out under Biosafety Level-3 condition.

All rhesus monkeys were 2-3 years old at the beginning of this study. At the beginning, all monkeys tested negative for 2019-nCoV. Twelve monkeys were divided into three groups—prophylactic, protection and control group with four animals in each group. Four monkeys of prophylactic group were intratracheally inoculated with siRNA combination encapsidated in HKP-SLiC nanoparticle system using a nebulizer. 24 h later, all twelve monkeys were intratracheally inoculated with $6.5 \times 10^7$ TCID$_{50}$ of 2019-nCoV in 1 mL. The prophylactic and protection groups were continuously inoculated with siRNA combination at 0, 24, 48, 72 and 96 h post-infection using the nebulizer. The control group was inoculated with PBS at the same time points.

All monkeys were observed twice daily for the symptoms and mortality. Chest X-rays were performed 1 day pre-infection and 3, and 5 day post-infection. The oropharyngeal, nasal, and cloacal swabs were collected at 1, 3, 5, 7, 9, 14, 21, and 28 day post-infection for the viral titration. Two infected monkeys from each group were sacrificed on the day 3 post-infection. Tissue including lung, trachea, spleen, liver, heart, brain, kidney, and colon tissue were collected for pathological and virological study.

The viral titers determination in the tissue and swab samples was performed as described in Example 2. To investigate the efficiency of siRNA candidates on inhibiting viral gene expression, the total RNA was extracted from the tissues and one-step quantitative real-time PCR was performed.

To investigate the efficiency of siRNA candidates on inhibiting viral protein expression, the total RNA were extracted from the tissues and the one-step quantitative real-time PCR were performed as described in Example 8.

Example 13. Animal Pharmacodynamic Testing

Non-human primate experiments (Chinese macaques) may be used to study the efficacy of siRNAs against SARS-CoV-2 infection. The research will be conducted in a laboratory with a biosafety level 3 (BSL-3).

Before the study started, all macaques are 2-3 years old, and all macaques tested negative for SARS-CoV-2. Twelve monkeys are randomly divided into 3 groups, namely the prevention group, the treatment group, and the control group (4 monkeys in each group). The 4 monkeys in the prevention group are inoculated through the airway with a siRNA composition encapsulated by polypeptide or liposome-like nano-carriers by using a handheld atomizing spray device. After 24 hours, all 12 monkeys are inoculated with $6.5 \times 10^7$ TCID$_{50}$ of SARS-CoV-2 (1 mL) through the airways. At the time of 0 hours (h), 24 h, 48 h, 72 h, and 96 h after infection, the monkeys in the prevention group and the protection group will continue to administer the siRNA composition through the atomized spray device. The control group will be inoculated with phosphate-buffered saline (PBS) at the corresponding time point.

We observe all monkeys twice a day and record their symptoms and mortality. We performed chest X-rays on macaques on 1 day before infection and on 3 and 5 days after infection. At the time of 1 day (d), 3 d, 5 d, 7 d, 9 d, 14 d, 21 d, and 28 d after infection, we collected the swabs in the oropharyngeal, nasal, and cloacal for virus titer determination. For monkeys who died after infection at different times, their tissues were collected for pathological and virological research, including lung, trachea, spleen, liver, heart, brain, kidney, and colon tissue.

In order to study the effectiveness of siRNA candidate drugs in inhibiting the expression of the viral gene, we determined the viral titer in the respiratory tract. At the same time, we extracted viral RNA from the cell supernatant and use the FRA/UAE spike protein-specific forward and reverse primers and TaqMan probes isolated from MERS-CoV to perform one-step quantitative real-time PCR. We then extracted total RNA from the harvested cells, and use gene-specific primers for the cDNA products of the non-structural protein ORF1AB and structural proteins S, E, M, and N to perform a 5'-RACE test to verify the mechanism of action of siRNAs.

Example 14: Design and Testing of siRNAs Against Live SARS-Cov2

Sequence analysis identified 25 practically overlapping siRNA molecules common to various CoV and SARS viruses. These 25 sequences were tested in the psiCheck2 plasmid system against virus-infected 293T and A549 cells (see FIG. 21, Table 3). The results are shown in Tables A-C below:

TABLE A

| | | Primary Screening (KD %, 60 ng/well, 48 h, 96 well) | |
|---|---|---|---|
| Target Gene Fragment | SiRNA# | 293T cells | A549 cells |
| Spike Gene fragment 1 | SCo34 | 60% | 74% |
| | SCo36 | | 65% |
| Spike Gene fragment 2 | SCo61 | | |
| | Guangzhou5 | 75% | 80% |
| | Guangzhou12 | 70% | 85% |
| | Guangzhou13 | 76% | 82% |
| | Guangzhou15 | 64% | 82% |
| | Guangzhou16 | 83% | 80% |
| | Guangzhou20 | 71% | |
| | Guangzhou21 | 81% | 91% |
| | Guangzhou22 | 83% | 90% |
| | Guangzhou23 | 79% | 87% |

TABLE A-continued

| | | Primary Screening (KD %, 60 ng/well, 48 h, 96 well) | |
|---|---|---|---|
| Target Gene Fragment | SiRNA# | 293T cells | A549 cells |
| | Guangzhou25 | 83% | 90% |
| | Guangzhou29 | 75% | 76% |
| | Guangzhou30 | 86% | 78% |
| | Guangzhou31 | 81% | 73% |
| | Guangzhou32 | 89% | 90% |
| ORF1ab gene fragment 1 | SCo1 | 76% | 80% |
| | SCo2 | 73% | 76% |
| ORF1ab gene fragment 4 | SCo8 | 52% | 65% |
| | Seq #3 | 89% | 89% |
| | Seq #4 | 76% | 76% |
| ORF1ab gene fragment 5 | Seq #5 | 85% | 84% |
| ORF3A & E & M | Seq #6 | 78% | 87% |
| | Seq #9 | 88% | 74% |
| N & ORF10 & 3'UTR | Seq #13 | 84% | |
| | Seq #14 | 79% | |
| | Seq #15 | 71% | |
| | Seq #19 | 76% | |
| | Seq #20 | 78% | |
| | Seq #21 | 79% | |
| | Seq #23 | 73% | |
| | Seq #24 | 86% | |

TABLE B

EC50 data summary of candidate siRNA sequences

| | EC50 (pg/ul) | | Target |
|---|---|---|---|
| siRNA# | 293T | A549 | Gene |
| SCo34 | 3732 | | Spike |
| SCo8 | 3186 | | Orf1ab |
| Guangzhou#16 | 20.4 | | Spike |
| Guangzhou#22 | 23.2 | | Spike |
| Guangzhou#31 | 44 | | Spike |
| Guangzhou#32 | 8 | | Spike |
| COV3 | 5.8 | 0.3 | Orf1ab |
| COV6 | 17.9 | 0.9 | Orf3a |
| COV13 | 3.1 | | N |
| COV24 | 2.4 | | 3'UTR |

TABLE C

| | | SEQ ID NO: | Primary Screening (KD %, 60 ng/well, 48 h, 96 well) | | EC50 (pg/ul, 48 h, 96 well) | |
|---|---|---|---|---|---|---|
| siRNA# | SS Sequence | | 293T | A549 | 293T | A549 |
| Guangzhou5 | CAAGUCAAACAAAUUUACAdTdT | 74 | 75% | 80% | | |
| Guangzhou12 | CUAAUCUUGCUGCUACUAAdTdT | 81 | 70% | 85% | | |
| Guangzhou13 | CUUGCUGCUACUAAAAUGUdTdT | 82 | 76% | 82% | | |
| Guangzhou16 | GGACAAUCAAAAAGAGUUGdTdT | 85 | 83% | 80% | 20.4 | |
| Guangzhou21 | CUGCUAAUCUUGCUGCUACUAAAAU | 90 | 81% | 91% | | |
| Guangzhou22 | GCUAAUCUUGCUGCUACUAAAAUGU | 91 | 83% | 90% | 23.2 | |
| Guangzhou23 | CUAAUCUUGCUGCUACUAAAAUGUC | 92 | 79% | 87% | | |
| Guangzhou25 | UGCUAAUCUUGCUGCUACUAAAAUG | 94 | 83% | 90% | | |
| Guangzhou30 | UUUGGUGGUUUUAAUUUUUCACAAA | 99 | 86% | 78% | | |
| Guangzhou31 | UUGGUGGUUUUAAUUUUUCACAAAU | 100 | 81% | 73% | 44 | |
| Guangzhou32 | UCUGCUAAUCUUGCUGCUACUAAAA | 101 | 89% | 90% | 8 | |
| COV3 | GGAAGGAAGTTCTGTTGAAdTdT | 408 | 89% | 89% | 5.8 | 0.3 |
| COV5 | CCTTTGAAAAAGGTGACTAdTdT | 409 | 85% | 84% | | |
| COV | CGACTACTAGVGTGCCTTTdTdT | 410 | 78% | 87% | 17.9 | 0.9 |
| COV9 | CGTTCGATTGTGTGCGTAdTdT | 411 | 88% | 74% | | |
| COV13 | CCAGAACAAACCCAAGGAAdTdT | 412 | 84% | | 3.1 | |
| COV24 | CCTAATGTGTAAAATTAAdTdT | 413 | 86% | | 2.4 | |

These data suggest that the sequences of siRNAs in Table D are the most potent sequences.

TABLE D

| | Target | EC50 293T cells pg/ul | EC50 A549 cells pg/ul |
|---|---|---|---|
| Guangzhou32 | Spike gene frag#2 | ~8 | ND |
| 25 seqs CoV#3 | ORF1ab gene frag #4 | 5.8 | 0.3 |
| 25 seqs CoV#6 | ORF3A | 17.9 | 0.9 |
| 25 seqs CoV#13 | N | 3.1 | ND |
| 25 seqs CoV#24 | 3' UTR | 2.4 | ND |

The identity of the siRNAs provided for testing, their location on the gene and their GC content is shown below in Table E:

TABLE E

| | Sense strand | Target | SEQ ID NO |
|---|---|---|---|
| CoV 1,, | GGTTCACCATCTGGTGTTT | ORF1AB | 414 |
| CoV 2,, | GGTGACATGGTACCACATA | ORF1AB | 415 |
| CoV 3,, | GGAAGGAAGTTCTGTTGAA,, | ORF1AB | 416 |
| CoV 4,, | GCCATTAGTGCAAAGAATA, | ORF1AB | 417 |
| CoV 5,, | CCTTTGAAAAAGGTGACTA, | ORF1AB | 418 |
| CoV 6,, | CGACTACTAGCGTGCCTTT, | ORF3A | 419 |
| CoV 7,, | CGTGCCTTTGTAAGCACAA,, | ORF3A | 420 |
| CoV 8,, | GGTACGTTAATAGTTAATA,, | E | 421 |
| CoV 9,, | CGCTTCGATTGTGTGCGTA,, | E | 422 |
| CoV 10,, | GCTACATCACGAACGCTTT, | M | 423 |
| CoV 11,, | CGCTTTCTTATTACAAATT,, | M | 424 |
| CoV 12,, | CGTGCTACAACTTCCTCAA, | N | 425 |
| CoV 13,, | CCAGAACAAACCCAAGGAA, | N | 426 |
| CoV 14,, | GGCCGCAAATTGCACAATT, | N | 427 |
| CoV 15,, | GCCGCAAATTGCACAATTT, | N | 428 |
| CoV 16,, | GGCATGGAAGTCACACCTT, | N | 429 |
| CoV 17,, | CCCACCAACAGAGCCTAAA, | N | 430 |
| CoV 18,, | CCACCAACAGAGCCTAAAA, | N | 431 |
| CoV 19,, | GCAGAATGAATTCTCGTAA, | ORF10 | 432 |
| CoV 20,, | CCTATATGGAAGAGCCCTA, | | 433 |
| CoV 21,, | GGAAGAGCCCTAATGTGTA, | | 434 |
| CoV 22,, | GCCCTAATGTGTAAAATTA, | | 435 |
| CoV 23,, | CCCTAATGTGTAAAATTAA, | | 436 |
| CoV 24,, | CCTAATGTGTAAAATTAAT, | | 437 |
| CoV 25,, | GCTATCCCCATGTGATTTT, | | 438 |

Sequences 3, 4, 14, and 18 had the best activity in a primary screen using live virus. The data obtained from these tests are shown below.

The analysis is shown as a 0% infection of total cells (left column), a 00 inhibition based on the mean infection rate seen in the non-silencing controls (next column to the right) and then the same for the next duplicate as well as the average of the duplicates. The 00 infection is calculated as the number of infected cells (expressing virus N protein, stained using a specific antibody) divided by the total number of cells counted as cell nuclei stained with Hoechst 33342 dye. A threshold of 50% was set (approximately 3 standard deviations of the non-silencing controls). The >70% inhibition seen with COV3 or COV4 was robust and shows promise for development.

| | Duplicate A % Infection | Duplicate A % Inhibition | Duplicate B % Infection | Duplicate B % Inhibition | Mean % infected | Mean % inhibition |
|---|---|---|---|---|---|---|
| COV3 | 3 | 84 | 6 | 79 | 5 | 81 |
| COV4 | 6 | 70 | 5 | 84 | 6 | 77 |
| COV18 | 9 | 59 | 7 | 76 | 8 | 68 |
| COV14 | 9 | 57 | 8 | 75 | 8 | 66 |
| COV15 | 10 | 54 | 13 | 57 | 11 | 56 |

Percent Inhibition was determined as compared to the mean of the non-silencing controls SiRNAs tested in the next round of testing (Concentration curves) are shown below; Primary hits shown in bold and underline 1. CoV3
2. CoV4
3. CoV5
4. CoV6
5. CoV9
6. CoV13
7. CoV14
8. CoV15
9. CoV18
10. CoV19
11. CoV20
12. CoV21
13. CoV23
14. CoV24
15. SCO1
16. SCO2
17. SCO8
18. SCO34
19. SCO36

The siRNAs were tested individually at varying concentrations for inhibition of the virus.

The data were plotted as shown in FIGS. 22A and 22B.

Nuclei loss was indicative of toxicity by the siRNAs in the cells and so these siRNAs were deprioritized for further testing.

Of the siRNA tested most performed consistently with the previous evaluation. For all siRNA it was not possible to calculate EC50 values as the performance of the siRNA was flat with siRNA not showing a relationship with the amount of siRNA used. Ranking the siRNA based on general inhibition of infection gave COV6, COV9 and SCO8 being the weakest while showing ~50% inhibition efficacy compared to the NS control. COV5, COV13, COV19 were the next most potent, blocking >70% of the control infection level.

The remaining siRNA showed a complete block of infection at the lowest concentration tested (3 nM). These were COV3, COV4, COV14, COV15, COV17, COV18, COV21, COV23, COV24, SCO1, SCO2, SCO34, SCO36.

With some siRNA treatments caused significant nuclei loss from wells. This is likely an indicator that the virus was killing cells (cytopathic effect) or that the siRNA was toxic when combined with virus infection. For the non-specific control siRNA treatment, cell loss was seen but at least one replicate set from two sets of controls was available to act as control. The impact of this on the data would be to underestimate the potency of the treatment. The treatments that caused cell loss in 2 or more of the replicates are indicated by the grading in the second graph for plate set 2 siRNA. Nuclei loss was seen in the set 1 data but at least 2 of the 3 replicates had >50% of the untreated control nuclei count and so the data are expected to be accurate. The infected but untreated control showed a 40% drop in cell numbers compared to cells that had not received virus but this is expected due to virus inhibiting cell growth, which for this assay was 1 cell division, accounting for the change in cell number.

In the next series of experiments the dose effect of the 4 of the most potent siRNAs were examined to determine the most potent sequences. We elected siRNAs #3, 4, 14 and 18 for evaluation.

Figure 23:
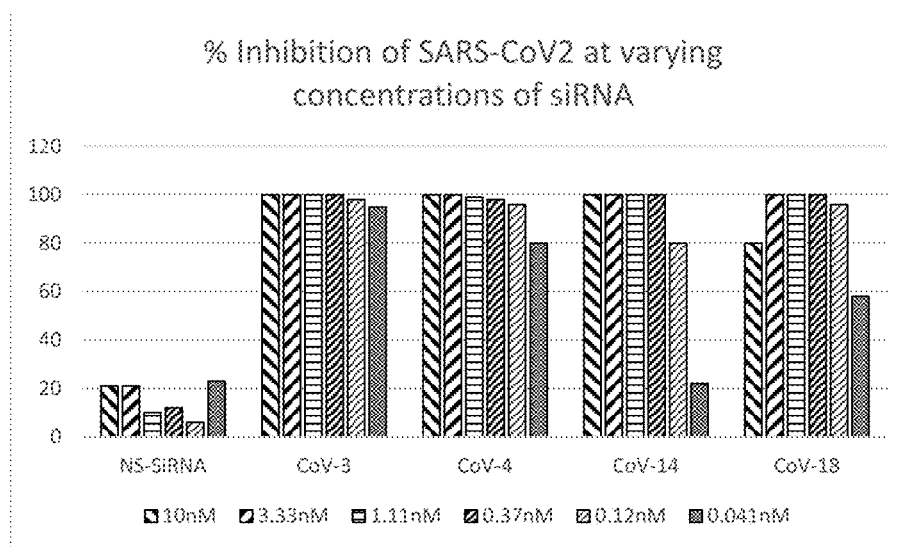
FIG. 23 shows he dose effect of 4 of the most potent siRNAs.

Each siRNA was evaluated in a dose response assay to determine potency against the virus. The data are shown in FIG. 23.

From the experimental results it would appear that the Cov3 and Cov4 sequences as well as the Cov18 sequence produce 100% inhibition of the virus at concentrations above 0.123 nM.

Figure 24:
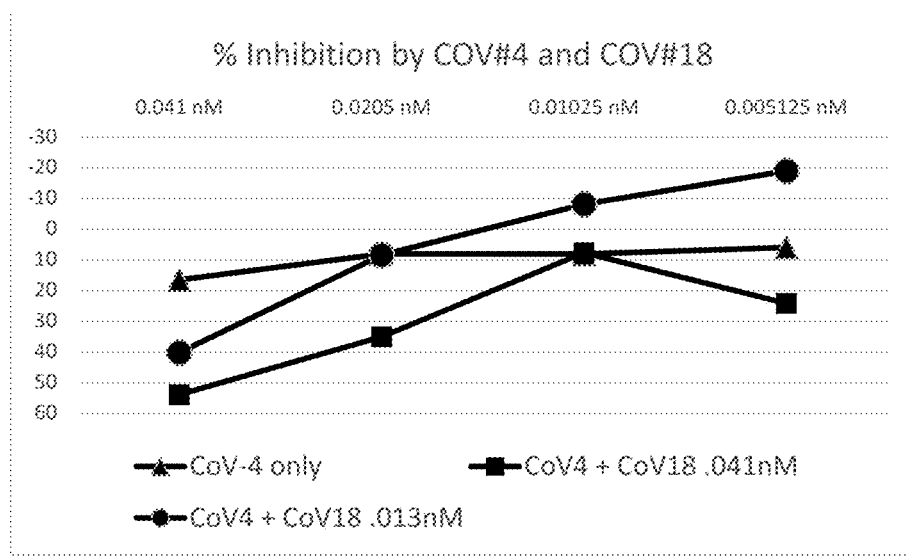
FIG. 24 shows a comparison of Cov #4 and Cov #18 and a mixture thereof on inhibition of virus

Since Cov #3 and Cov #4 are against the ORF1ab segment and Cov #18 was against the N-protein we decided to compare the combination of #3 and #18 as well as the combination of #4 and #18 to determine whether combining 2 siRNAs against different segments would affect the efficacy. FIG. 24 shows a comparison of Cov #4 and Cov #18 on inhibition of virus Cov #4 concentration was varied between 0.041 nM and 0.005 nM while Cov #18 was tested at 2 concentrations in combination with Cov #4 (0.041 nM and 0.013 nm).

Maximal inhibition was observed when the 2 siRNAs were combined at 0.041 nM Cov #4 and 0.041 nM Cov #18. Maximal inhibition for the combination at these concentrations was 55%.

Figure 25:
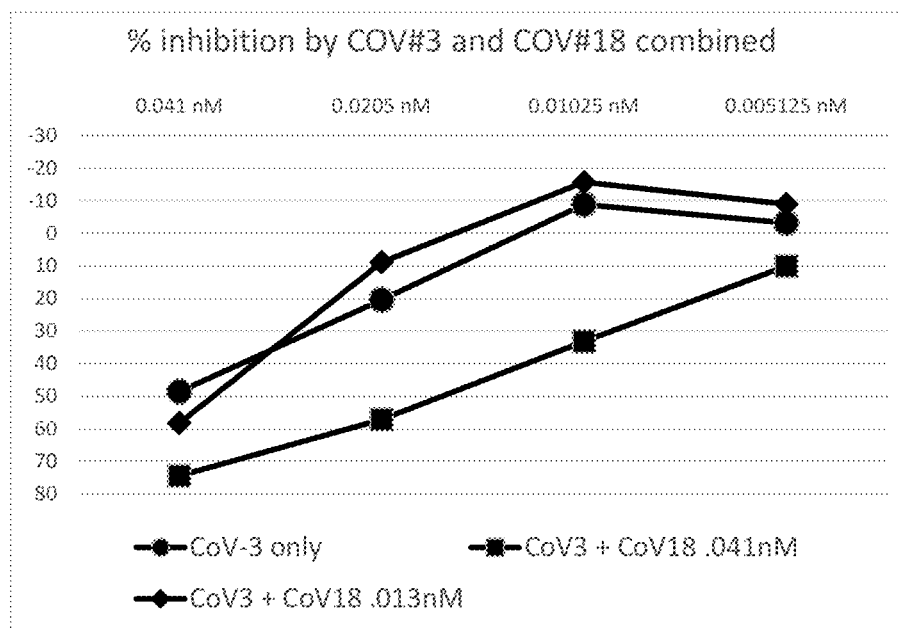
FIG. 25 shows a comparison of of Cov #3 and Cov #18 and a combination thereof on the virus.

We also compared the combination of Cov #3 and Cov #18 under similar conditions, as shown in FIG. 25.

Cov #3 concentration was varied between 0.041 nM and 0.005 nM while Cov #18 was tested at 2 concentrations in combination with Cov #3 (0.041 nM and 0.013 nm).

Maximal inhibition was observed when the 2 siRNAs were combined at 0.041 nM Cov #3 and 0.041 nM Cov #18. Maximal inhibition for the combination at these concentrations was 75%. Cov3 alone at this concentration gave only ~48% inhibition—suggesting some additivity when the 2 siRNAs were combined.

Combining Cov #3 with Cov #18 provides the benefit of avoiding the ability for the virus to escape therapeutic pressure unless it mutates in the regions of both the ORF1ab segment as well as the N-protein segment specifically targeted by the siRNA sequences.

CoV3: GGAAGGAAGTTCTGTTGAA (SEQ ID NO: 401)

CoV18: CCACCAACAGAGCCTAAAA (SEQ ID NO: 405)

25mer versions of CoV3 and CoV18 can also be prepared and used:

CoV3 25mer: GGAAGGAAGTTCTGTTGAATTAAAA (SEQ ID NO: 402)

CoV18 25mer: CCACCAACAGAGCCTAAAAAGGACA (SEQ ID NO: 406)

The 2 siRNAs can be delivered using a nanoparticle formulation to ensure that they both are delivered to the same cell at the same time.

NRP1 (neuropilin receptor) has been postulated as aiding uptake of SARS-COV2 into the endothelial cells of the lung (Cantuti-Castelvetri et al., Science 10.1126/science.abd2985 (2020)). IT has previously been shown that select formulations of the polypeptide nanoparticle consisting of Histidine and Lysine moieties in specific orientation can provide binding through the NRP1 receptor. Leng and Mixson, J Gene Med; 18: 134-144 (2016). allows peptide nanoparticle-mediated delivery of the siRNAs to the same cells that will take up SARS-Cov2. The siRNAs silence the genes required by the virus for viability and hence reduce the viral titer.

Delivery of the polypeptide nanoparticles containing two or more siRNAs, such as combinations of: CoV3 and Cov18; CoV3 and CoV14; CoV4 and CoV14; and CoV4 and CoV18 may be achieved via Intraperitoneal administration, IV administration or via direct inhalation of the material into the lungs. Nanoparticles of appropriate given sizes may be prepared using H2K alone or in combination with H3K, together the combinations of siRNAs described above. Formulation of various combinations of H2K and H3K4b (HKP) may be prepared using, for example, an HK: siRNA ratio of 3:1. Previous experiments have shown that H2K alone when mixed with siRNAs can form nanoparticles of ~124 nm in diameter. Above a ratio of H2K: HKP of 1:1 nanoparticles also form with siRNAs. Optimal sizes (<200 nm) are observed at ratios of 1:2 and 1:5. HKP alone forms nanoparticles of 121 nm.

In addition, the formation of nanoparticles has been tested using additional linear peptides such as H3K(+H)-C (containing a Cysteine at the C-terminus) or using the branched HKP (HKP(+H)). Ratios of H2K: H3K(+H)-C of 1:0.2 resulted in nanoparticles of 161 nm. H2K: HKP(+H) at 1:0.2 ratio gave a nanoparticle of 146 nm while HKP(+H) alone gave 129 nm particles and HKP alone gave 121 nm. These results show that using H2K alone or in combination with these other peptide sequences create nanoparticles that exhibit varying degrees of NRP1 targeting. Nanoparticles containing a higher degree of H2K may demonstrate improved binding to NRP1 than those with lower amounts.

What is claimed is:

1. A pharmaceutical composition comprising at least a first siRNA molecule that targets a conserved region of an ORF1AB gene of the Wuhan seafood market novel pneumonia 2019 Novel Coronavirus (2019-nCoV) genome, and at least a second siRNA that targets a conserved region of an N-protein gene of said 2019-nCoV genome, wherein said composition comprises a pharmaceutically acceptable carrier, wherein said carrier comprises a polymeric nanoparticle and/or a liposomal nanoparticle carrier, wherein said first siRNA molecule is selected from the group consisting of SEQ ID NO:401-403 and 414-418, and wherein said second siRNA molecule is selected from the group consisting of SEQ ID NO: 404-406 and 425-431.

2. The composition of claim 1 wherein the siRNA molecules inhibit non-structural (NS) RdRp, replicase or helicase virus gene expression.

3. The composition of claim 1, wherein the siRNA molecules comprises oligonucleotides having a length of 19-25 base pairs.

4. The composition of claim 1, wherein the siRNAs molecules are designed against the sense strand sequences of NS genes.

5. The composition according to claim 1, wherein the polymeric nanoparticle carrier comprises a Histidine-Lysine co-polymer (HKP).

6. The composition of claim 5, wherein said HKP and said siRNA molecules self-assemble into nanoparticles.

7. The composition of claim 5, wherein said SLiC and said siRNA molecules self-assemble into nanoparticles in a formulation comprising cholesterol.

8. The composition according to claim 1, wherein the liposomal nanoparticle carrier comprises a Spermine-Lipid Conjugates (SLiC) in formulation with cholesterol.

9. A pharmaceutical composition comprising at least a first siRNA molecule that targets a conserved region of an ORF1AB gene of the Wuhan seafood market novel pneumonia 2019 Novel Coronavirus (2019-nCoV) genome, and at least a second siRNA that targets a conserved region of an N-protein gene of said 2019-nCoV genome, wherein said composition comprises a pharmaceutically acceptable carrier, wherein said carrier comprises a polymeric nanoparticle and/or a liposomal nanoparticle carrier, wherein the composition further comprises a combination of two sense strands, one from each of said first and second siRNA molecules, and said combination is selected from the group consisting of:

CoV3 and CoV18
CoV3 and CoV14
CoV4 and CoV14 and
CoV4 and CoV18,
respectively, wherein CoV3 has the sequence GGAAGGAAGTTCTGTTGAA (SEQ ID NO: 401) or GGAAGGAAGTTCTGTTGAATTAAAA (SEQ ID NO: 402), CoV4 comprises the sequence GCCATTAGTGCAAAGAATA (SEQ ID NO: 403), CoV-14 has the sequence GGCCGCAAATTGCACAATT (SEQ ID NO: 404), and CoV18 has the sequence CCACCAACAGAGCCTAAAA (SEQ ID NO: 405) or CCACCAACAGAGCCTAAAAAGGACA (SEQ ID NO: 406).

10. The composition of claim 9, wherein the combination of sense strands comprises CoV3 and CoV18, and wherein the CoV3 sense strand has the sequence GGAAGGAAGTTCTGTTGAA (SEQ ID NO: 401) and the CoV18 sense strand has the sequence CCACCAACAGAGCCTAAAA (SEQ ID NO: 405).

11. The composition of claim 9, wherein the combination of sense strands comprises CoV3 and CoV18, and wherein the CoV3 sense strand has the sequence GGAAGGAAGTTCTGTTGAA (SEQ ID NO: 401) and the CoV18 sense strand has the sequence CCACCAACAGAGCCTAAAAAGGACA (SEQ ID NO: 406).

12. The composition of claim 9, wherein the combination of sense strands comprises CoV3 and CoV18, and wherein the CoV3 sense strand has the sequence GGAAGGAAGTTCTGTTGAATTAAAA (SEQ ID NO: 402) and the CoV18 sense strand has the sequence CCACCAACAGAGCCTAAAA (SEQ ID NO: 405).

13. The composition of claim 9, wherein the combination of sense strands comprises CoV3 and CoV14, and wherein the CoV3 sense strand has the sequence GGAAGGAAGTTCTGTTGAATTAAAA (SEQ ID NO: 402) and the CoV18 sense strand has the sequence CCACCAACAGAGCCTAAAAAGGACA (SEQ ID NO: 406).

14. The composition of claim 9, wherein the combination of sense strands comprises CoV4 and CoV14, and wherein the CoV4 sense strand has the sequence GCCATTAGTGCAAAGAATA (SEQ ID NO: 403), and the CoV14 sense strand has the sequence GGCCGCAAATTGCACAATT (SEQ ID NO: 404).

15. The composition of claim 9, wherein the combination of sense strands comprises CoV4 and CoV18, and wherein the CoV4 sense strand has the sequence GCCATTAGTGCAAAGAATA (SEQ ID NO: 403), and the CoV18 sense strand has the sequence CCACCAACAGAGCCTAAAA (SEQ ID NO: 405).

16. The composition of claim 9, wherein the combination of sense strands comprises CoV4 and CoV18 and wherein the CoV4 sense strand has the sequence GCCATTAGTGCAAAGAATA (SEQ ID NO: 403), and the CoV18 sense strand has the sequence CCACCAACAGAGCCTAAAAAGGACA (SEQ ID NO: 406).

\* \* \* \* \*